(12) United States Patent  
Snell

(10) Patent No.: US 7,520,387 B2  
(45) Date of Patent: Apr. 21, 2009

(54) POCKET-SIZED VACUUM PACKED DIAPER KIT

(75) Inventor: Alan Kay Snell, Idaho Falls, NC (US)

(73) Assignee: Diaperoos, LLC, Charlotte, NC (US)

( * ) Notice: Subject to any disclaimer, the term of this patent is extended or adjusted under 35 U.S.C. 154(b) by 58 days.

(21) Appl. No.: 11/930,285

(22) Filed: Oct. 31, 2007

(65) Prior Publication Data

US 2008/0142404 A1    Jun. 19, 2008

Related U.S. Application Data

(63) Continuation-in-part of application No. 10/907,389, filed on Mar. 31, 2005, and a continuation of application No. 10/907,333, filed on Mar. 29, 2005, now abandoned, which is a continuation-in-part of application No. 10/665,169, filed on Sep. 18, 2003, now abandoned, said application No. 10/907,333.

(60) Provisional application No. 60/660,792, filed on Mar. 11, 2005, provisional application No. 60/451,433, filed on Mar. 4, 2003, provisional application No. 60/660,792, filed on Mar. 11, 2005.

(51) Int. Cl.  
*B65D 71/00* (2006.01)

(52) U.S. Cl. .............. 206/581; 206/440; 206/494; 206/524.8

(58) Field of Classification Search .............. 206/38, 206/225, 229, 233, 581, 440, 441, 494, 524.8, 206/812; 604/385, 385.02–385.06, 385.13, 604/385.19  
See application file for complete search history.

(56) References Cited

U.S. PATENT DOCUMENTS

| 4,564,108 | A | | 1/1986 | Widlund et al. | |
|---|---|---|---|---|---|
| 4,702,378 | A | * | 10/1987 | Finkel et al. | 206/581 |
| 5,443,161 | A | * | 8/1995 | Jonese | 206/581 |
| 6,004,307 | A | * | 12/1999 | Colon et al. | 206/581 |
| 6,540,084 | B2 | * | 4/2003 | Silvers | 206/581 |
| 6,723,080 | B1 | * | 4/2004 | Habib et al. | 604/385.06 |
| 2002/0179478 | A1 | * | 12/2002 | Silvers | 206/494 |

FOREIGN PATENT DOCUMENTS

JP    10-95481    *    4/1998

* cited by examiner

*Primary Examiner*—Luan K Bui  
(74) *Attorney, Agent, or Firm*—Tillman Wright, PLLC; Chad D. Tillman; James D. Wright

(57) ABSTRACT

Vacuum packed absorbent articles including diapers, kits thereof, and retail packages including vacuum packed and non vacuum packed absorbent articles are disclosed.

20 Claims, 94 Drawing Sheets

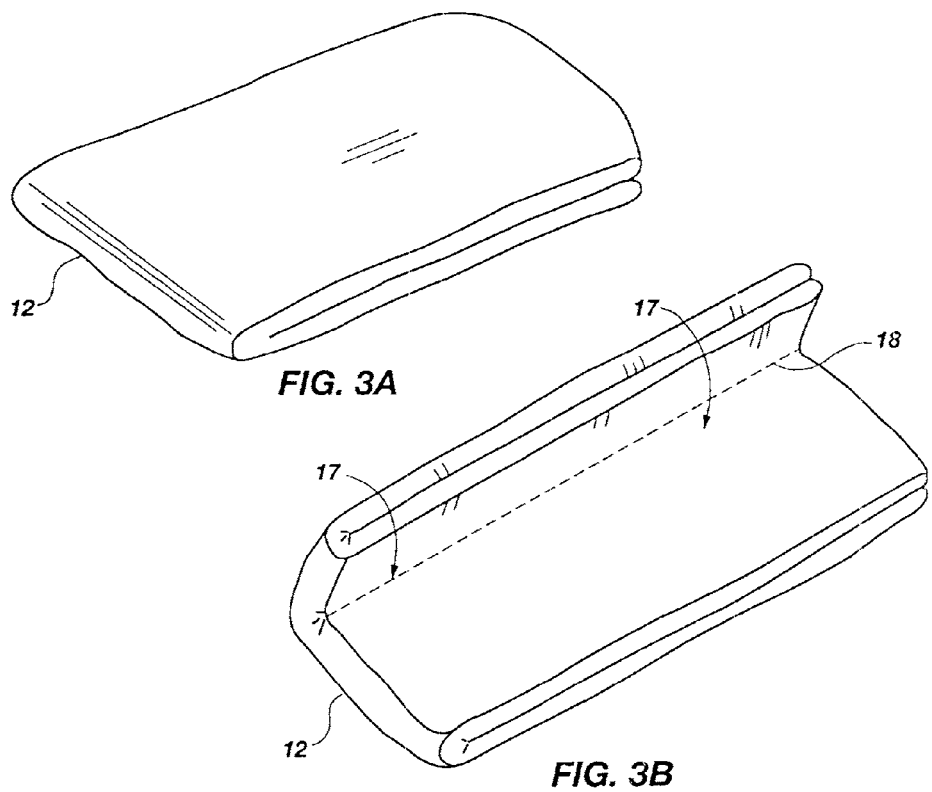
FIG. 3A
FIG. 3B
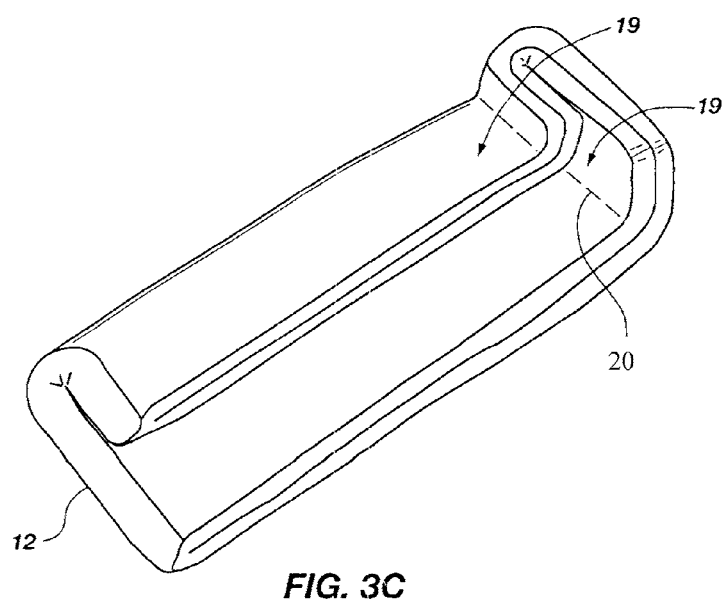
FIG. 3C

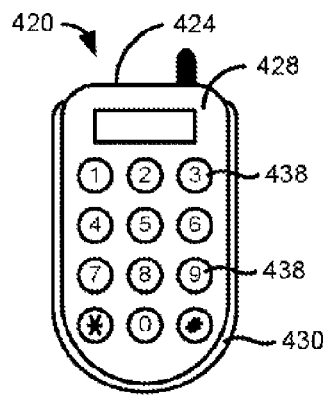
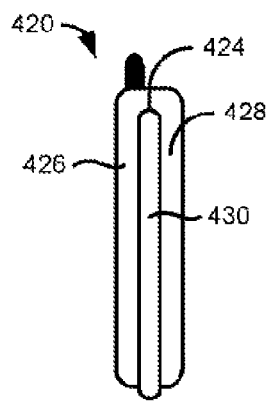
FIG. 45  FIG. 46
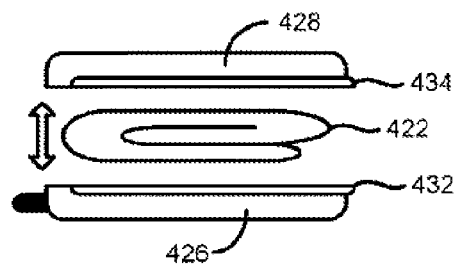
FIG. 47
FIG. 48
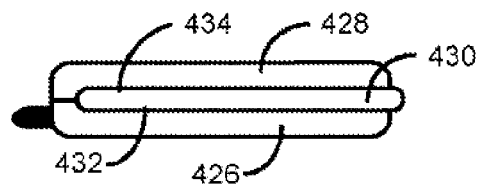
FIG. 49

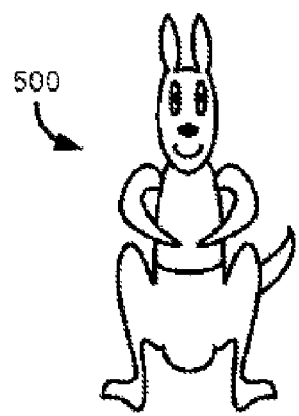
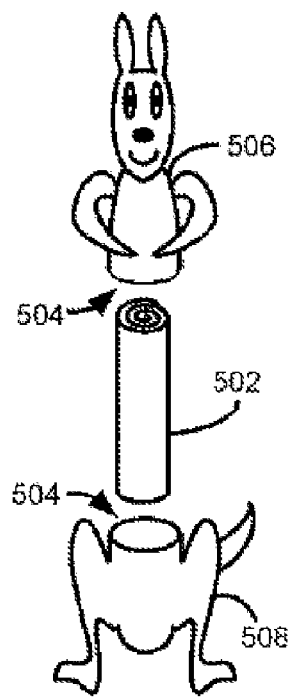
FIG. 53　　　　　　FIG. 54
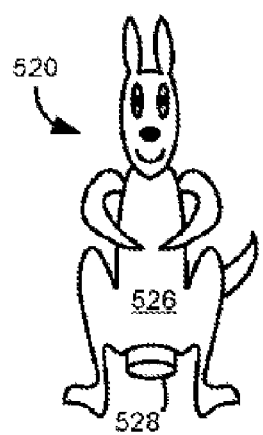
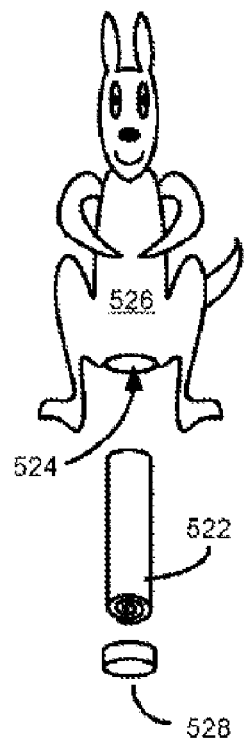
FIG. 55　　　　　　FIG. 56

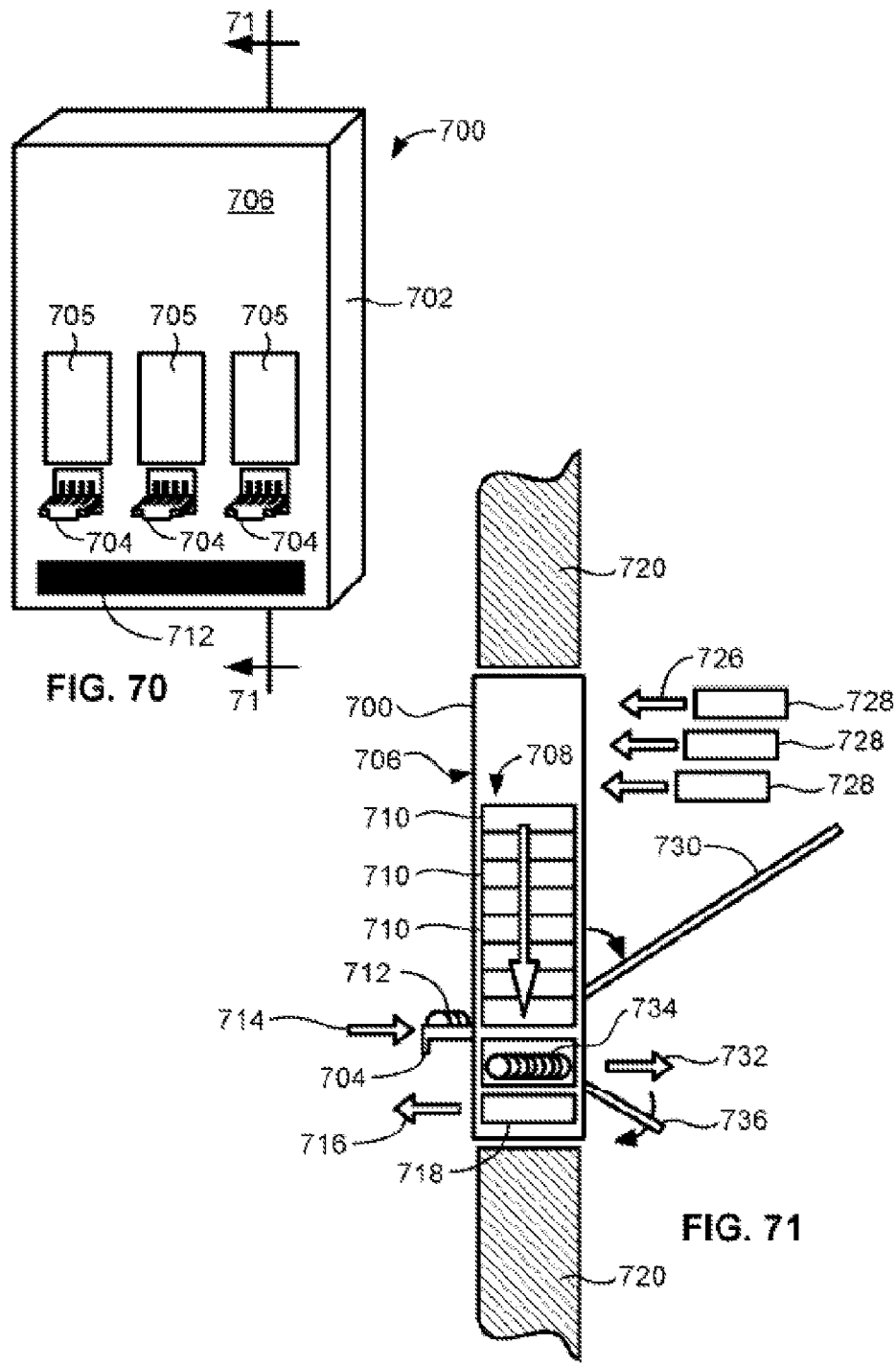

POCKET-SIZED VACUUM PACKED DIAPER KIT

I. CROSS-REFERENCE TO RELATED APPLICATIONS

This application is a continuation-in-part patent application of, and claims priority to, U.S. patent application Ser. No. 10/907,389, filed Mar. 31, 2005, which '389 application republished as U.S. patent application publication no. U.S. 2005/0155898, which '389 application is a nonprovisional of and claims priority to U.S. patent application Ser. No. 60/660,792, filed on Mar. 11, 2005, and which '389 application is a continuation of U.S. patent application Ser. No. 10/907,333, filed Mar. 29, 2005, abandoned, which '333 application itself is: (1) a continuation-in-part of and claims priority to U.S. patent application Ser. No. 10/665,169, filed Sep. 18, 2003, abandoned, which '169 application published on Sep. 9, 2004, as U.S. patent application publication no. U.S. 2004/0176735 A1, and which '169 application is a nonprovisional of and claims priority to U.S. provisional patent application Ser. No. 60/451,433, filed Mar. 4, 2003; and (2) a nonprovisional application of and claims priority to U.S. patent application Ser. No. 60/660,792, filed on Mar. 11, 2005.

Each of the disclosures of these patent applications and published patent applications are hereby incorporated herein by reference. Additionally, the present application furthermore hereby incorporates by reference herein U.S. patent application publication no. US 2004/0167489 A1.

II. BACKGROUND

The present application relates generally to disposable packaged diapers and related infant and incontinent adult care accessories. More particularly, the present application relates to a reduced size packaged diaper, and related infant and incontinent adult care accessories and kits. The present application also relates to a combination package for retail sale (hereinafter "COMBO PACK") that includes reduced and non-reduced articles and, in particular, reduced diapers and non-reduced diapers.

Diapers are generally a necessity for very young children and incontinent adults. Individuals incapable of controlling the release of bodily waste in a manner sufficiently reliable to enable the use of restroom facilities, and those caring for such individuals, typically need to carry extra disposable diapers and changing accessories. This is typically because it is difficult to predict when a diaper worn by an individual may need to be changed. Caretakers of babies and others requiring diapers often carry spare, clean diapers for this reason.

Many of the following discussions and examples are directed to use of diapers in infant care. However, it will be apparent that many of the same considerations apply to use of diapers for non-infant, incontinent persons.

Storage and carriage of clean diapers is often inconvenient. For instance, disposable diapers are generally rather bulky items not given to easy storage or carriage in a purse, pocket, or otherwise about the person. In addition, the problem can be acerbated in that diapers can be subject to expansion from the typically somewhat compressed state in which they are normally provided to consumers, especially in circumstances where the diapers are subject to contact with other items within a storage bag. For example, many disposable diapers are provided in a bi-fold configuration meant to minimize the space taken in storing the diaper. However, after being removed from their original packaging, bi-fold diapers often unfold or otherwise expand to consume an even larger storage space. Thus, disposable diapers can become more bulky and difficult to carry than when in their nominal, packaged condition.

In addition, it is often the case that it is not sufficient to simply change a soiled diaper and replace it with a clean diaper. For instance, cleaning of the individual who wore the diaper may need to be performed with diaper accessories, such as moist wipes. Also, it may be necessary to apply ointment or powder to the individual wearing the diaper to treat or prevent incidents of diaper rash or other skin conditions. Due to these considerations, caretakers of individuals requiring diapers often carry clean diapers and diaper changing accessories in a dedicated container, is often referred to as a "diaper bag." By doing so, when it becomes necessary to change a diaper, all of the materials needed by the caretaker are available in one location.

While a conventional diaper bag provides a dedicated container in which diapers and diaper accessories can be stored and carried, the requirement of carriage of a diaper bag often adds to the difficulty of a caretaker's responsibility. For example, parents of young children often must carry a purse or briefcase for the parent's own needs. In addition to this, the parent may need to carry the young child; and, of course, the child's diaper bag. This can leave the parent with no free hands for other tasks.

While conventional clean diapers and diaper changing accessories can be stored and carried in other carrying containers such as purses, backpacks, briefcases, etc., the bulky nature of conventional disposable diapers results in the diapers occupying a relatively large space within the carrying container. In addition, diaper changing accessories such as moist wipes, ointment, powder, etc., add to the space consumed by conventional clean diapers and can be difficult to locate among other items stored in the backpack, purse, case, or the like.

Where the diapers being carried by the caretaker are for bottle feeding infants, the problems discussed above are further exacerbated by the need to carry materials for feeding the baby. In addition to the accoutrement necessary to attending to changing the baby's diaper, things such as bottles, nipples, containers of formula or milk, etc., generally must also be carried.

III. SUMMARY OF THE INVENTION OF THE PRESENT APPLICATION

It has been recognized that it would be advantageous to develop a packaged diaper that requires a relatively small amount of storage space. In addition, it has been recognized that it would be advantageous to develop a diaper and related accessory kit that consumes a relatively small amount of space while providing substantially all of the materials necessary to change an individual's diaper. It has also been recognized that it would be advantageous to develop an infant care kit that consumes a relatively small amount of space while providing substantially all of the materials necessary to feed the infant and change the infant's diaper.

The invention of the present application provides a packaged diaper, including a diaper, having a first, nominal size, and a second, reduced size, the reduced size of the diaper being convenient for carriage and storage of the diaper. An encasement can also be provided, in which the diaper can be disposed in the second, reduced size. The encasement can confine the diaper so that the diaper is retained in its reduced size by the encasement and so that the diaper is returned to its nominal size upon opening of the encasement.

In accordance with another aspect of the invention of the present application, a packaged diaper is provided, including a diaper, having a first, nominal configuration characterized by a nominal length, width and height, and a second, reduced configuration characterized by a second, reduced length, width and height. The reduced length can be between about 2 inches to about 4 inches, the reduced width can be between about 1.0 inch to about 2.5 inches, and the reduced thickness can be between about 0.5 inches to about 1.5 inches. An encasement can also be provided, in which the diaper can be disposed and retained in the second, reduced configuration.

In accordance with another aspect of the invention of the present application, a packaged diaper is provided, including a diaper, having a first, nominal size and shape, and a reduced, substantially cylindrical size and shape. The reduced, substantially cylindrical shape can have a diameter between about 0.5 inches to about 1.5 inches and a length between about 2 inches to about 4 inches. An encasement can also be provided, in which the diaper can be disposed and retained in the reduced, substantially cylindrical shape.

In accordance with another aspect of the invention of the present application, a packaged diaper is provided, including a diaper having a first, nominal volumetric configuration characterized by a nominal length and width of the diaper, and a second, reduced volumetric configuration characterized by a reduced length and width of the diaper. An encasement can also be provided, the encasement formed of a substantially air impermeable material. The diaper can be disposed in the encasement in the second, reduced volumetric configuration and the encasement can be at least partially evacuated of air so as to contain the diaper in at least a partial vacuum state. Differential pressure within and without the encasement can maintain the second, reduced volumetric configuration of the diaper and the encasement can be sealed to confine the diaper so that the diaper is returned to its nominal volumetric configuration upon opening of the encasement.

In accordance with another aspect of the invention of the present application, a method of packaging a diaper is provided and includes the steps of: a) folding the diaper at least once along both a lengthwise and a crosswise aspect of the diaper; b) disposing the folded diaper within an encasement comprised of a substantially air impermeable material; c) evacuating air from the encasement and the folded diaper; and d) sealing the encasement to maintain a vacuum created within the encasement and the folded diaper.

In accordance with another aspect of the invention of the present application, a method of packaging a diaper is provided and includes the steps of: a) volumetrically reducing a size of the diaper to a size convenient for carriage and storage of the diaper; b) disposing the volumetrically reduced diaper within an encasement; and c) maintaining the volumetrically reduced size of the diaper with the encasement.

In a more detailed aspect, the encasement can facilitate this by virtue of its hoop strength and/or by means of a pressure differential acting upon the encasement.

In accordance with another aspect of the invention of the present application, a diaper changing kit is provided and includes a packaged diaper in accordance with one or more previously set forth aspects of the invention of the present application, at least one diaper accessory, and a container in which the packaged diaper and the diaper accessory can be disposed. In a more detailed aspect, the accessory can be one or more of: a) a moistened wipe; b) baby powder; c) a medicament; d) a swab; e) a lotion; and, a disposal bag for a dirty diaper. In another more detailed aspect the container can be configured to have a first, oversized size and shape and a second smaller size and shape, and to also function as a disposal container for a dirty diaper.

In accordance with another aspect of the invention of the present application, an infant care kit is provided and includes a diaper, a diaper accessory, a portion of infant food and an infant feeding assembly. The infant feeding assembly can have a hollow body and a nipple portion couplable thereto. The diaper, diaper accessory, and portion of infant food can each be disposed in the infant feeding assembly. The infant feeding assembly can be configured to: i) contain each of the diaper, at least one diaper accessory and at least one portion of infant food; and ii) upon removal of the diaper and diaper accessory, receive the portion of infant food within the hollow body and deliver the infant food to an infant with the food delivery device. In a more detailed aspect a warming pack can also be provided for warming the infant food.

In accordance with another aspect of the invention of the present application, a packaged diaper is provided and includes a diaper, having a first, nominal size, and a second, reduced size, the reduced size of the diaper being convenient for carriage and storage of the diaper. A restraint can also be provided, in which the diaper can be disposed in the second, reduced size. The restraint can confine the diaper so that the diaper is retained in its reduced size by the restraint and so that the diaper is returned to its nominal size upon opening of the restraint.

In accordance with another aspect of the invention of the present application, a packaged diaper is provided and includes a densified diaper volumetrically reduced to a second reduced volume and increased density from a first greater volume and lesser nominal density. The reduction of the diaper can entail reduction in one or more dimensions. An encasement can also be provided in which the diaper can be disposed in the second reduced volume. The encasement can confine the diaper so that the diaper is retained in the reduced volume by the encasement.

In accordance with another aspect of the invention of the present application, an expandable diaper is provided and includes a diaper being reduced to a second, reduced size from a first, nominal size, the reduced size of the diaper being reduced in at least two dimensional directions relative to the nominal size. An encasement can also be provided in which the diaper can be disposed in the second, reduced size. The encasement can confine the diaper so that the diaper is retained in the reduced size by virtue of the encasement.

In accordance with another aspect of the invention of the present application, a packaged diaper is provided and includes a diaper, having a first, nominal size, and a second, reduced size, the reduced size of the diaper being convenient for carriage and storage of the diaper. A restraint can also be provided in which the diaper can be disposed in the second, reduced size. The restraint can confine the diaper so that the diaper is retained in its reduced size by the restraint and so that the diaper is returned to its nominal size upon opening of the restraint.

In addition to the foregoing, one or more other aspects of the invention relates to a method for miniaturizing a diaper. In this respect, a preferred such method comprises: folding a diaper within a jig; transferring the folded compressed diaper from the jig using a clamping apparatus; inserting the folded compressed diaper into a pliable bag; and vacuum sealing the bag thereby further miniaturizing the diaper within the bag. The miniaturized finished product preferably fits into a conveniently sized box for eliminating the bulky nature of carrying bulky diapers within a purse or other carrying case. Furthermore, the finished product is condensed down to a firm and hard exterior surface, and may be disguised in appearance, for example, to look like a candy bar instead of a baby diaper or an adult diaper. The miniaturization process can be readily adapted to mechanical application for automatic manufacturing assembly line runs.

Still yet, other inventive aspects and features of the invention are set forth in U.S. patent application Ser. No. 11/927,232, and its corresponding publication U.S. patent application publication no. 2008/0128295, both of which are incorporated herein by reference.

Additional aspects and features, and advantages thereof, will be apparent from the detailed description which follows, taken in conjunction with the accompanying drawings, which together illustrate, by way of example, features of the invention of the present application. In addition to the aforementioned aspects and features of the present invention, it should be noted that the present invention further encompasses the various possible combinations of such aspects and features.

IV. BRIEF DESCRIPTION OF THE DRAWINGS

FIG. 3A is a perspective view of a diaper;

FIG. 3B is a perspective view of the diaper of FIG. 3A in the process of folding the diaper along a lengthwise aspect of the diaper;

FIG. 3C is a perspective view of the diaper of FIG. 3B in the process of folding the diaper along a crosswise aspect of the diaper;

Figure 36A:
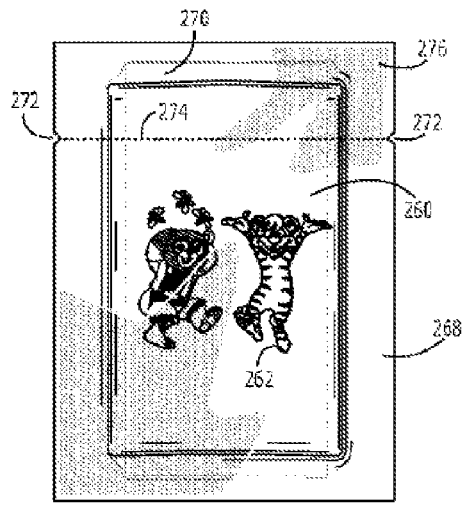
Figure 36B:
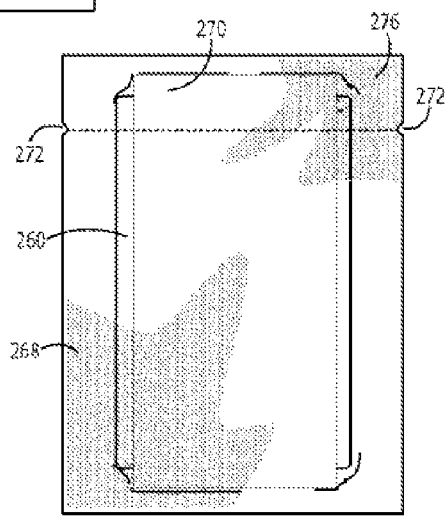
Figure 37:
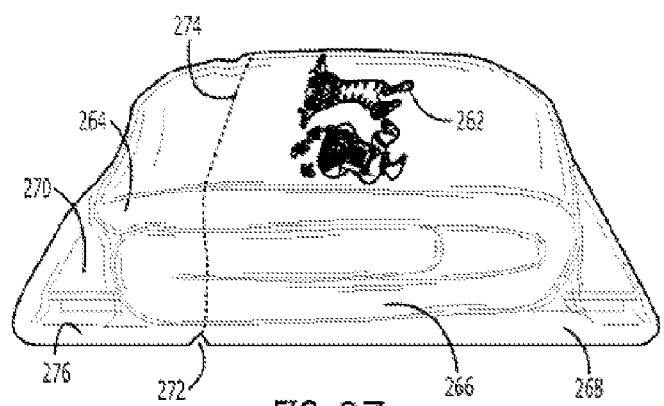

FIG. 36A, FIG. 36B, and FIG. 37 are views of a kit having a vacuum-packed diaper and diaper accessories, wherein indicia of the diaper is visible through the encasement in which the diaper is vacuum-sealed.

Figure 6:
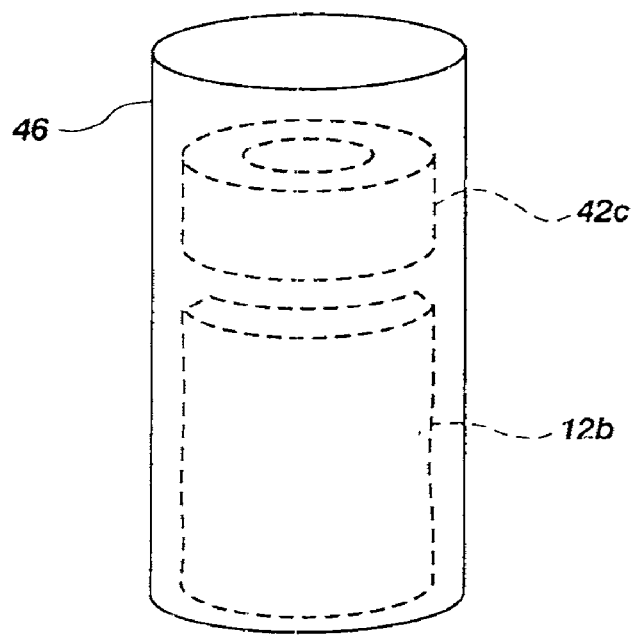
FIG. 6 is a perspective view of another diaper kit.
Figure 38:
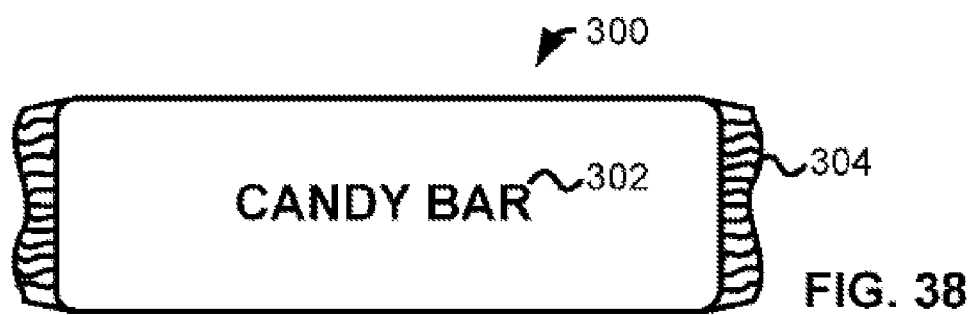
Figure 39:
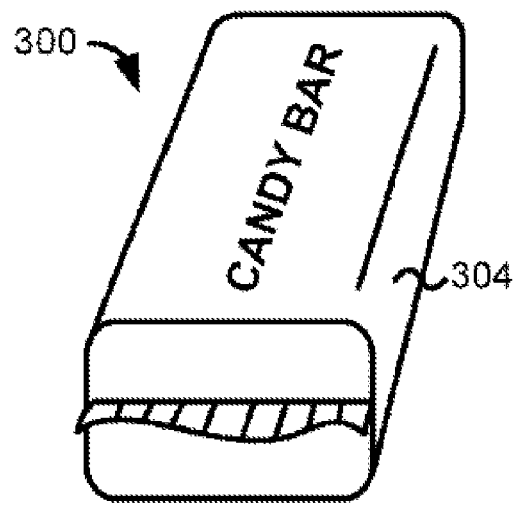
Figure 40:
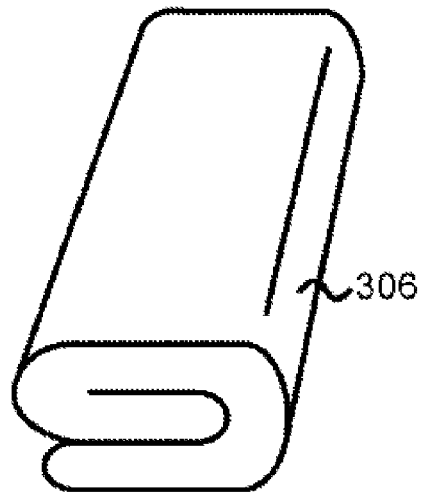
Figures 41, 42:
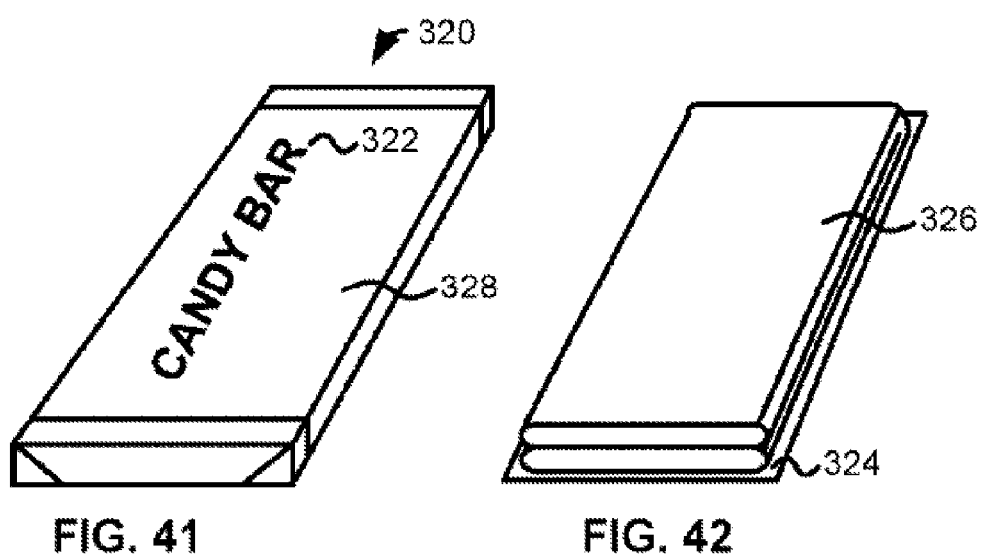
Figure 43:
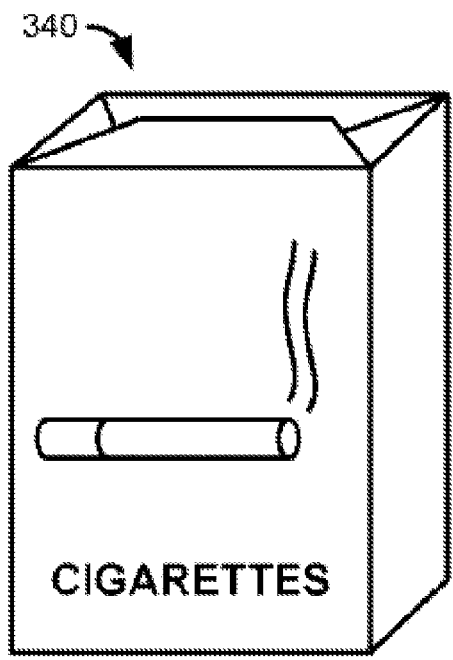
Figure 44:
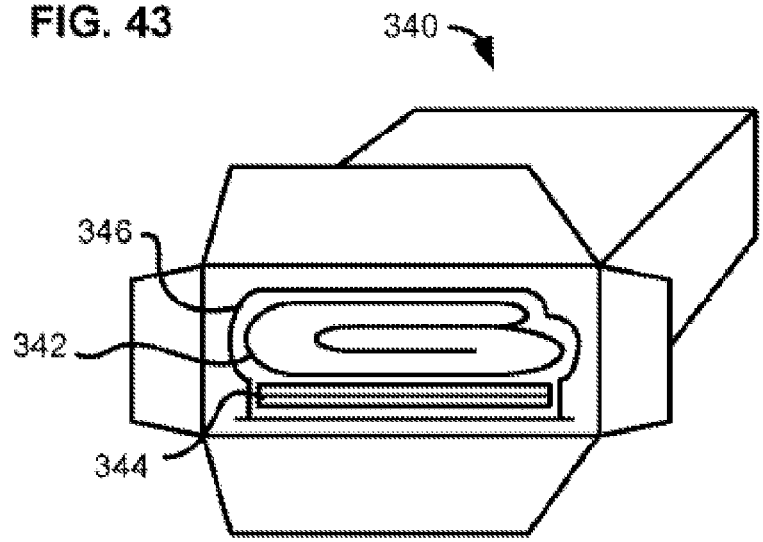
Figure 50:
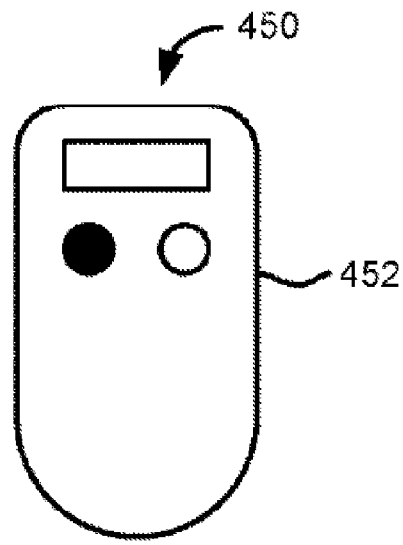
Figure 51:
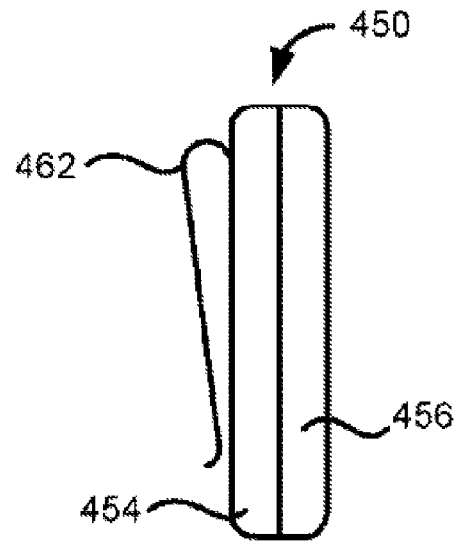
Figure 52:
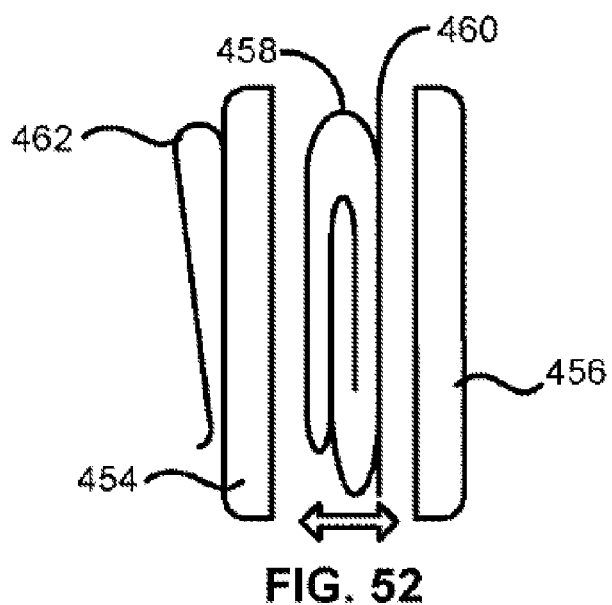
Figure 57:
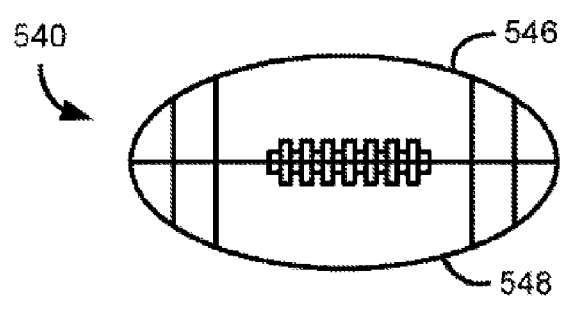
Figure 58:
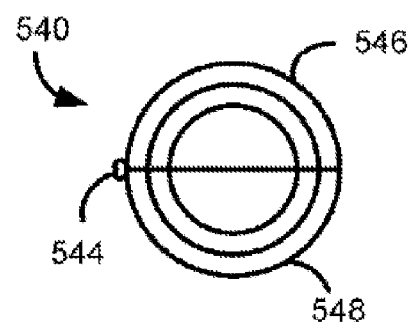
Figure 59:
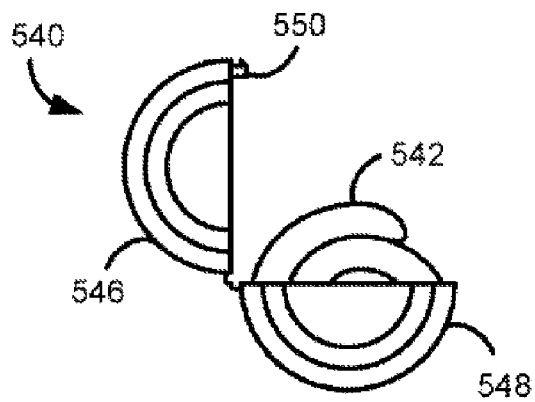
Figure 60:
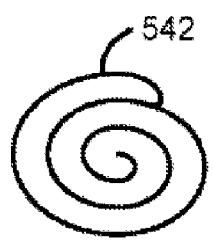
Figure 61:
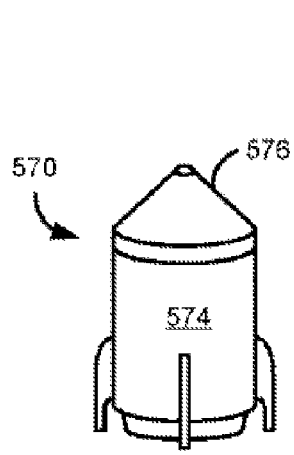
Figure 62:
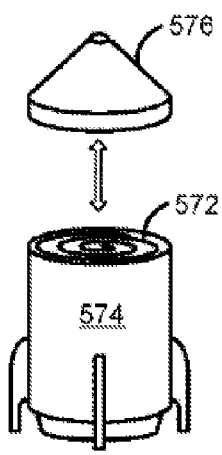
Figure 63:
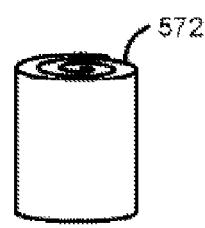
Figure 64:
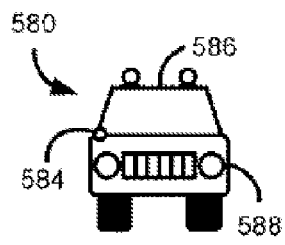
Figure 65:
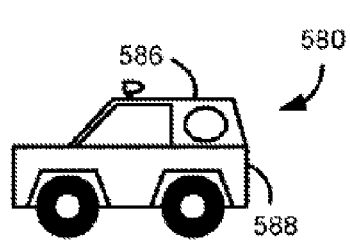
Figure 66:
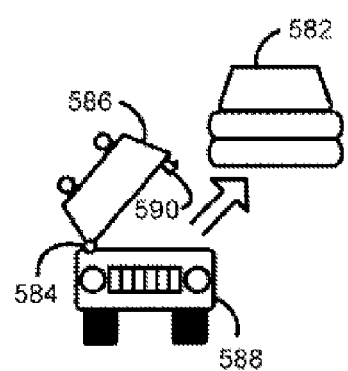
Figure 67:
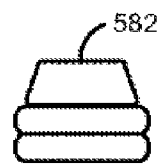
Figure 68:
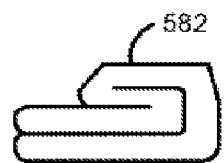
Figure 69:
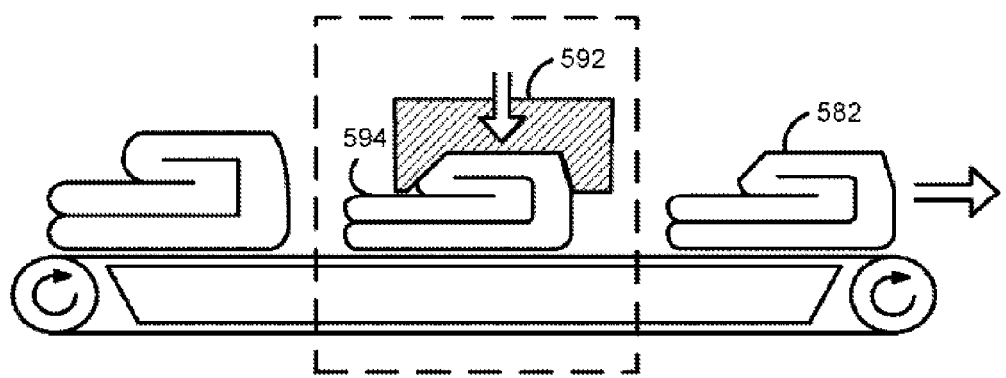
Figure 72:
Figure 73:
Figure 74:
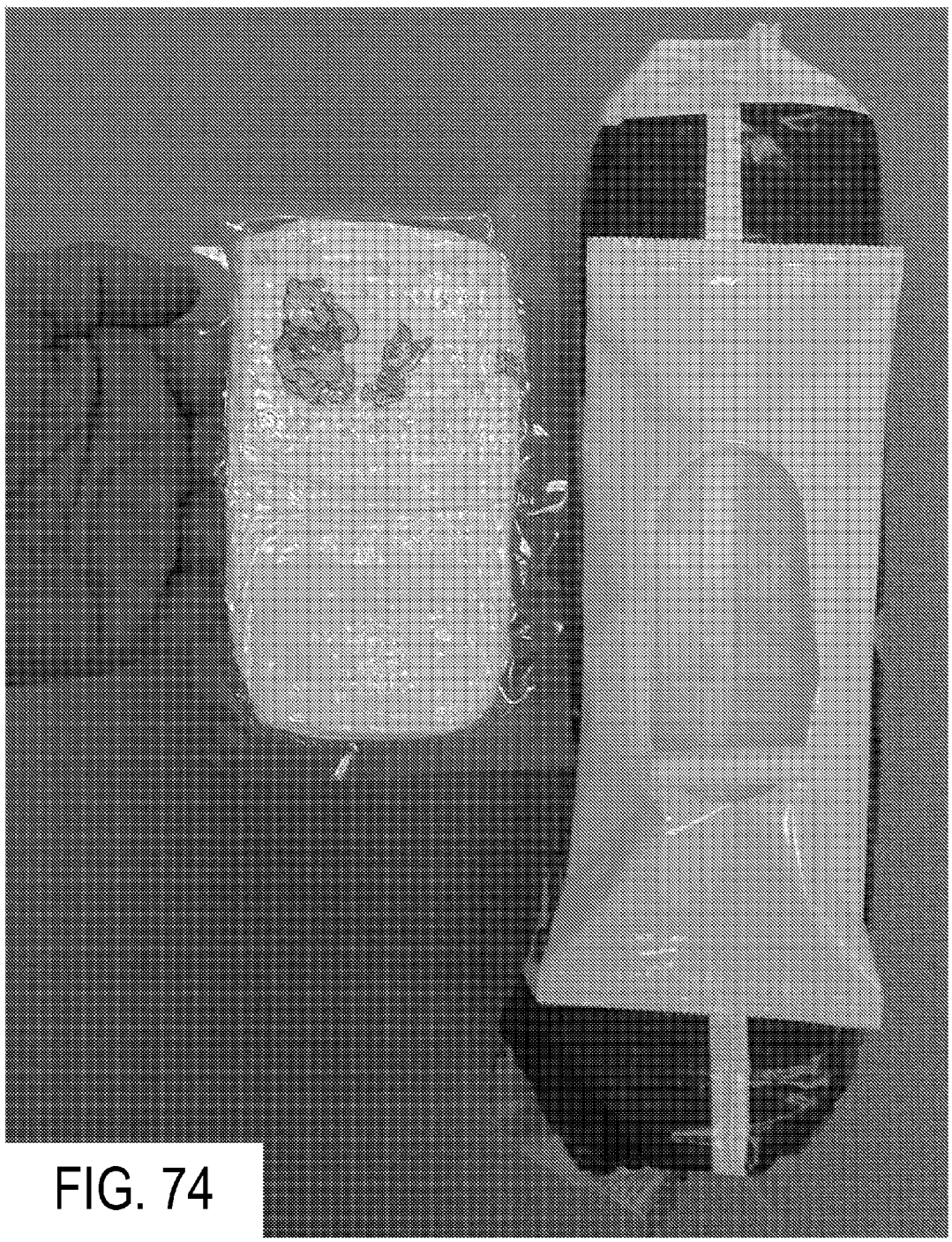
Figure 75:
Figure 76:
Figure 77:
Figure 78:
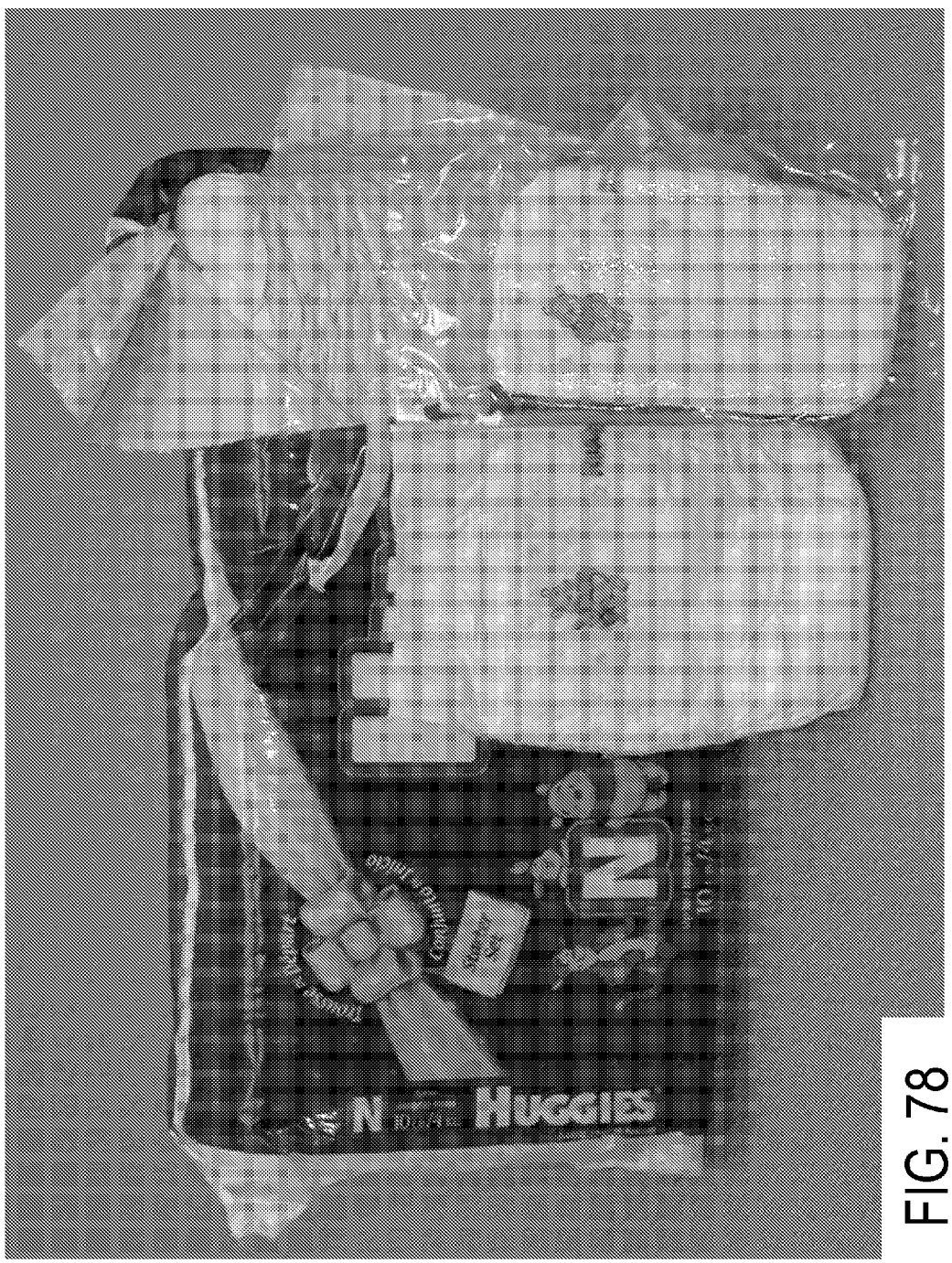

FIGS. 38-39 illustrate a disguisedly packaged absorbent article wherein the package resembles a candy bar;

FIG. 40 illustrates the configuration of the absorbent article disposed within the package of FIGS. 74-75;

FIG. 41 illustrates another disguisedly packaged absorbent article wherein the package resembles a candy bar;

FIG. 42 illustrates the configuration of the absorbent article disposed within the package of FIG. 41;

FIG. 43 illustrates another disguisedly packaged absorbent article wherein the package resembles a pack of cigarettes;

FIG. 44 illustrates the absorbent article and accessories contained within the package of FIG. 43;

FIGS. 45-46 illustrate another disguisedly packaged absorbent article wherein the package resembles a mobile phone;

FIG. 47 illustrates separation of the encasement of FIGS. 45-46 resembling the mobile phone for accessing of the absorbent article contained therein;

FIG. 48 illustrates the attachment of the clamping band to the shells of the encasement of FIGS. 45-46 resembling the mobile phone;

FIG. 49 further illustrates the package of FIGS. 45-46 following attachment of the clamping band as shown in FIG. 48;

FIGS. 50-51 illustrate another disguisedly packaged absorbent article wherein the package resembles a pager;

FIG. 52 illustrates separation of the pager of FIGS. 50-51 for accessing of the absorbent article contained therein;

FIG. 53 is an illustration of a toy container;

FIG. 54 is an exploded view of the toy container of FIG. 53;

FIG. 55 is an illustration of another toy container;

FIG. 56 is an exploded view of the toy container of FIG. 55;

FIGS. 57-59 are illustrations of a toy container;

FIG. 60 is an illustration of a volumetrically reduced diaper that is disposed within the toy container of FIGS. 57-59;

FIGS. 61-62 are illustrations of another toy container;

FIG. 63 is an illustration of a volumetrically reduced diaper that is disposed within the toy container of FIGS. 61-62;

FIGS. 64-66 are illustrations of still yet another toy container;

FIGS. 67-68 are illustrations of a volumetrically reduced diaper that is disposed within the toy container of FIGS. 64-6;

FIG. 69 is an illustration of a method of making the volumetrically reduced diaper of FIGS. 67-68;

FIG. 70 is an illustration of a vending machine;

FIG. 71 is cross-sectional illustration of the vending machine of FIG. 70 taken along the line 71-71 in FIG. 70;

FIG. 72 is an illustration of a COMBO PACK having a first package and a second package;

FIG. 73 shows a vacuum-packed diaper within the second package of FIG. 72;

FIG. 74 shows the vacuum-packed diaper removed from the second package of FIG. 73;

FIG. 75 is an illustration of a COMBO PACK having a first package and a transparent encasement that contains a vacuum-packed diaper;

FIG. 76 is an illustration image of a COMBO PACK that includes a vacuum-packed diaper and a number of non vacuum-packed diapers all contained within a first package;

FIG. 77 is another view of the COMBO PACK of FIG. 76;

FIG. 78 illustrates a vacuum-packed diaper and a non vacuum-packed diaper of FIG. 76 after having been removed from the first package.

Figure 79:
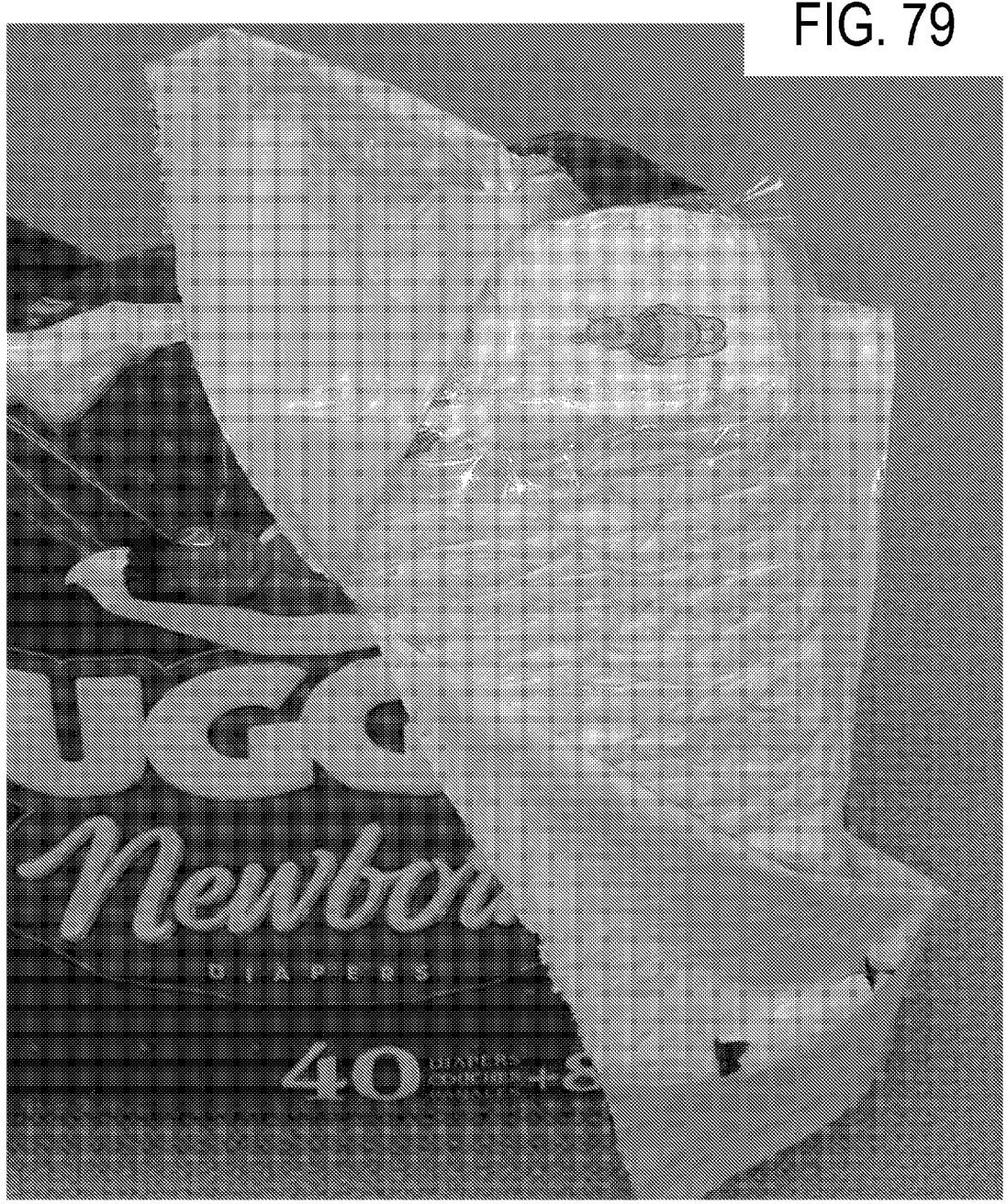
Figure 80:
Figure 81:
Figure 82:
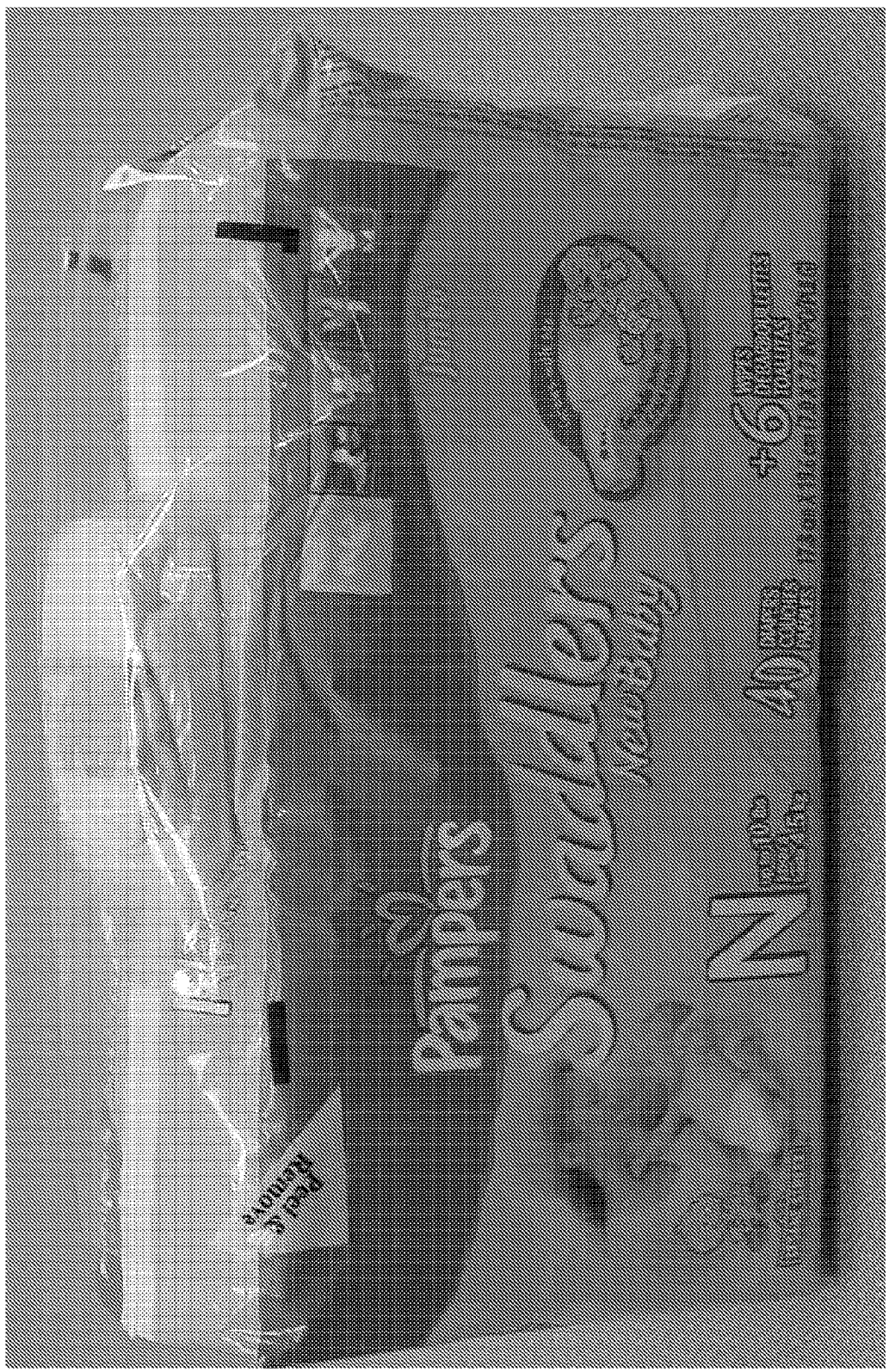
Figure 83:
Figure 84:
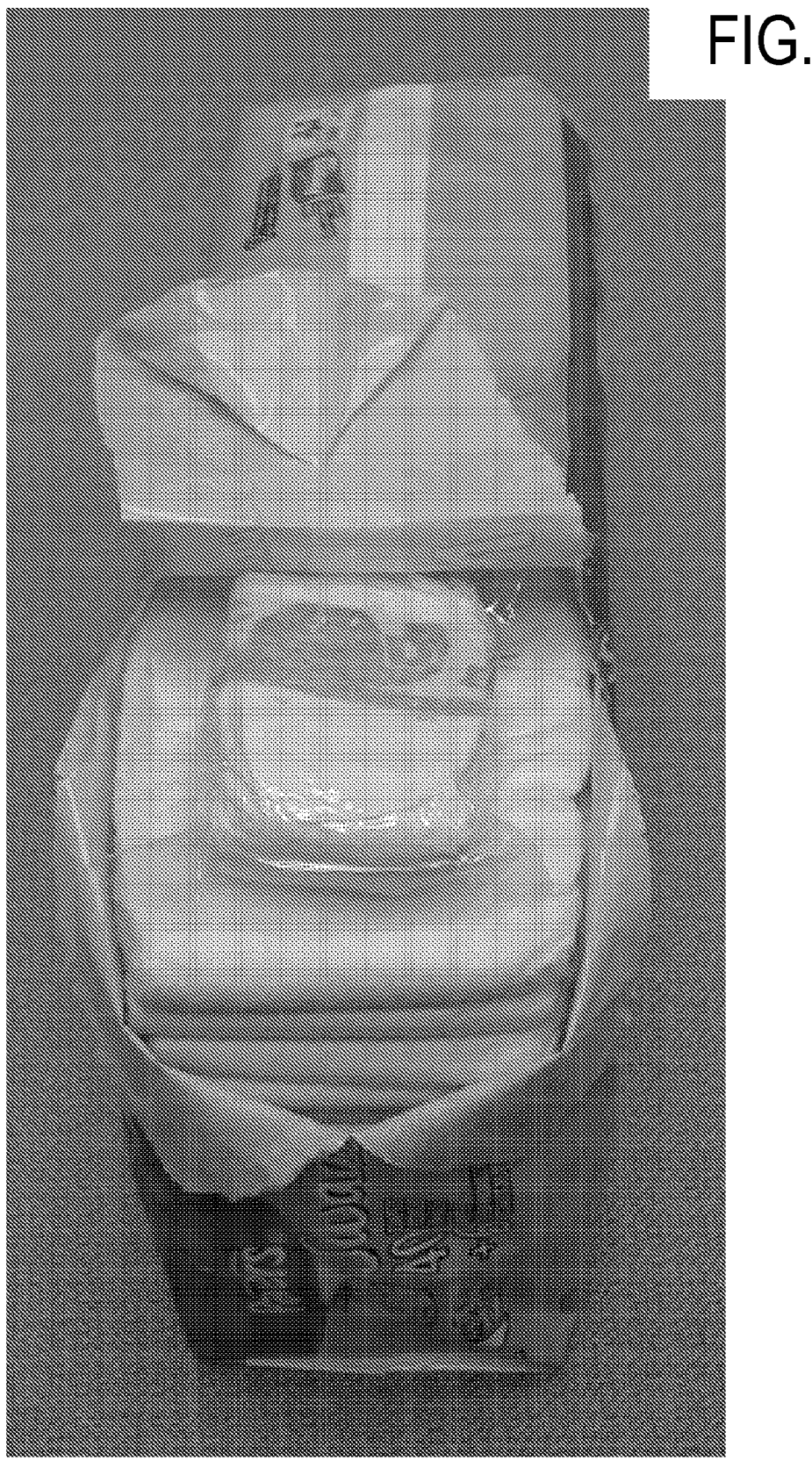
Figure 85:
Figure 86:
Figure 87:
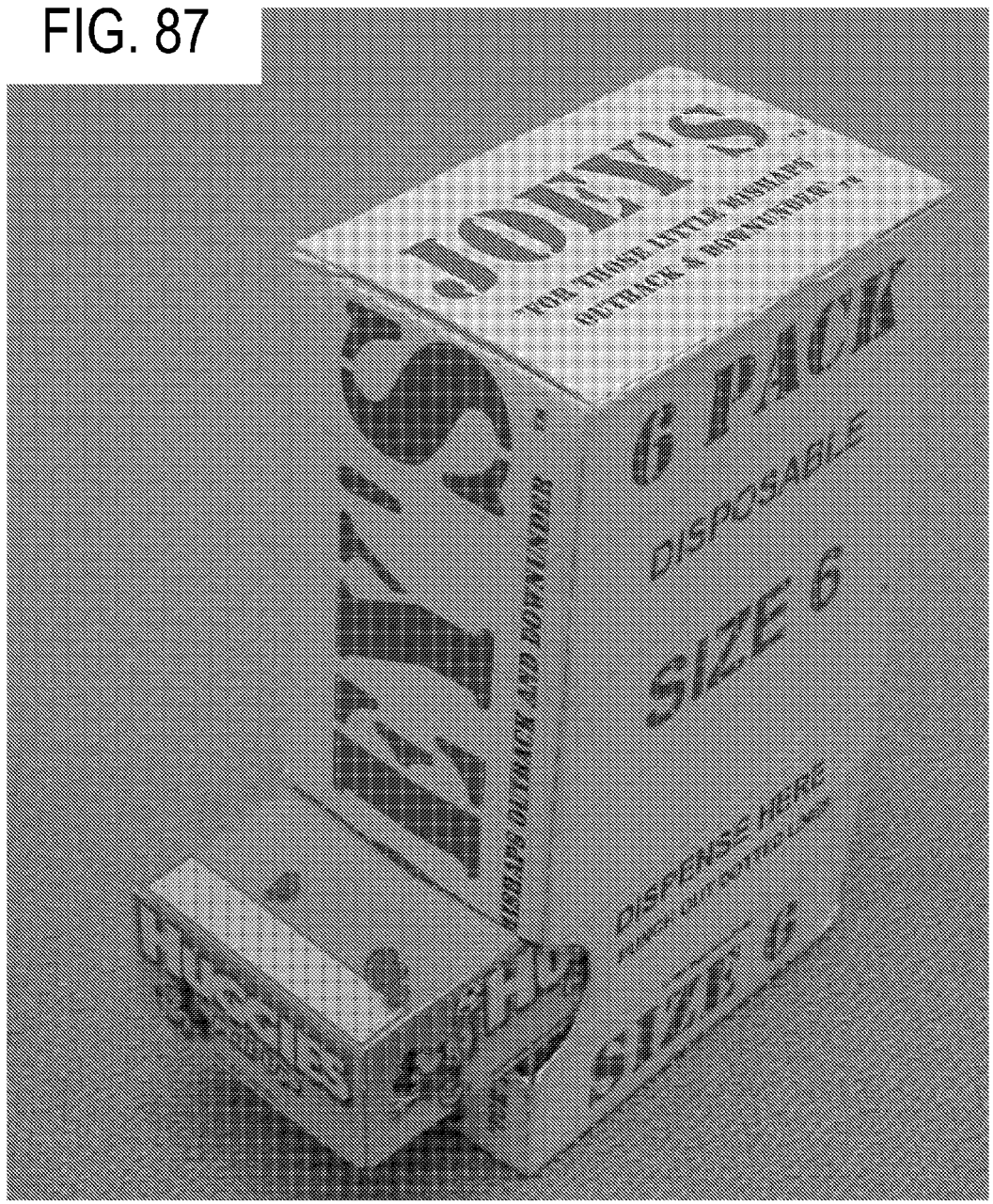
Figure 88:
Figure 89:
Figure 90:
Figure 91:
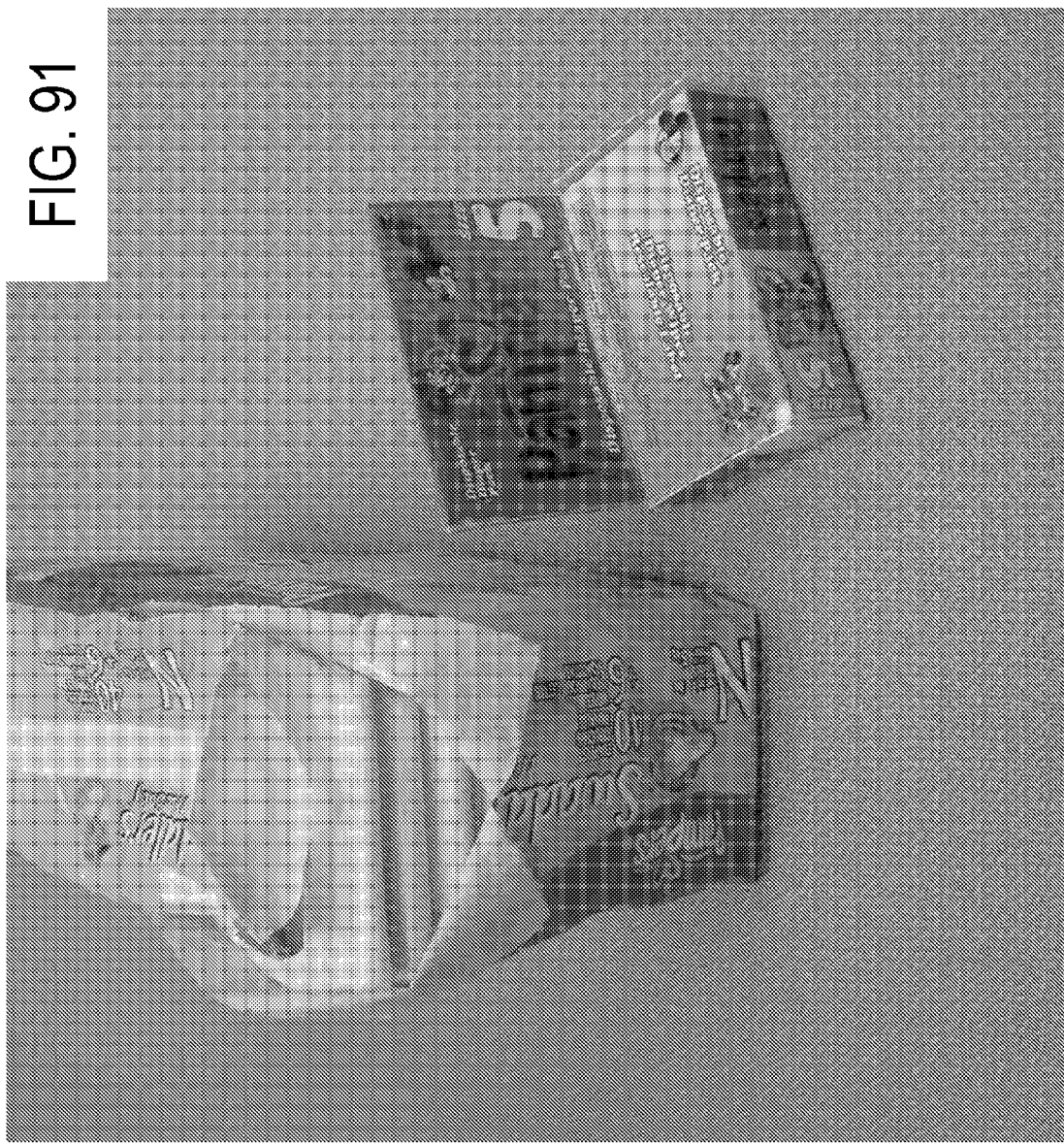
Figure 92:
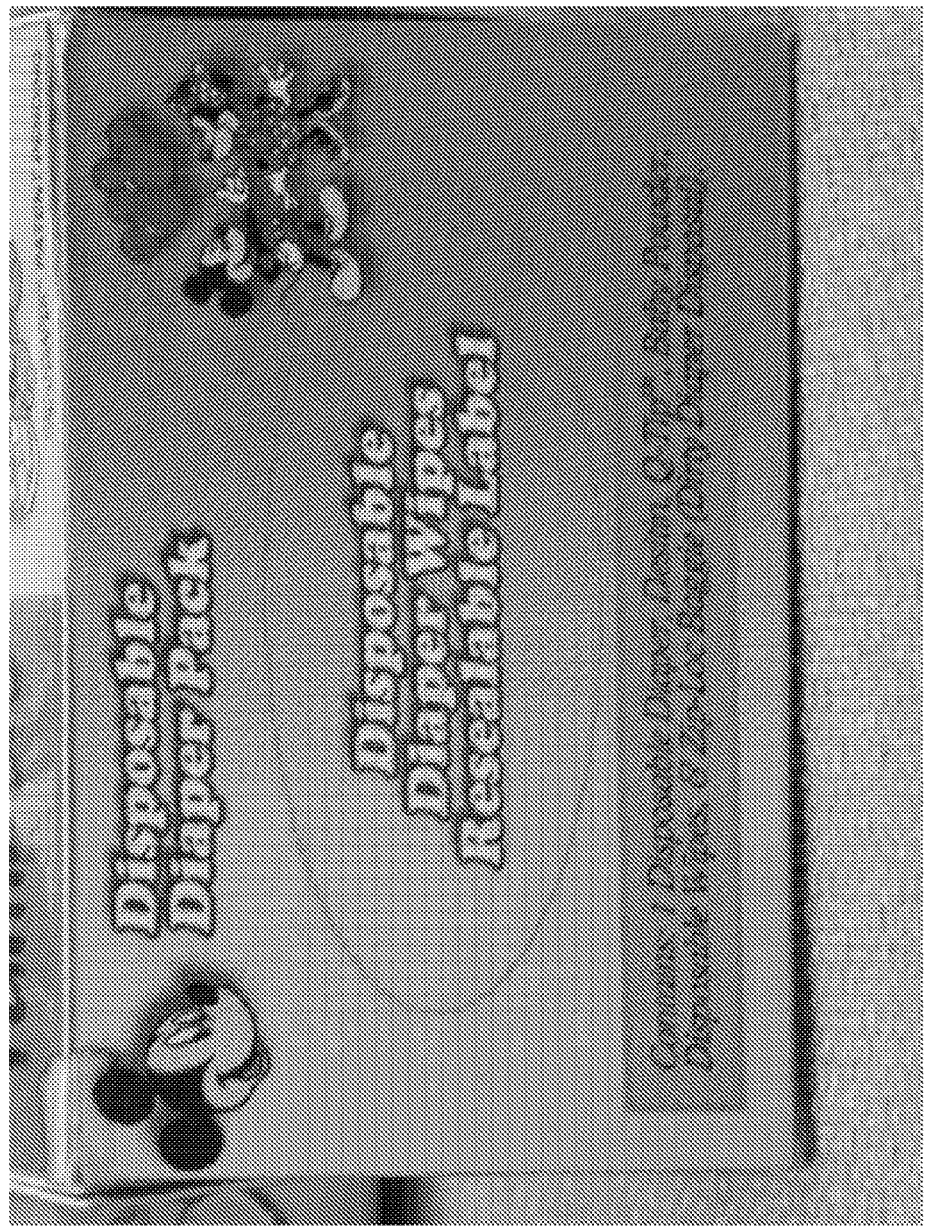
Figure 93:
Figure 94:
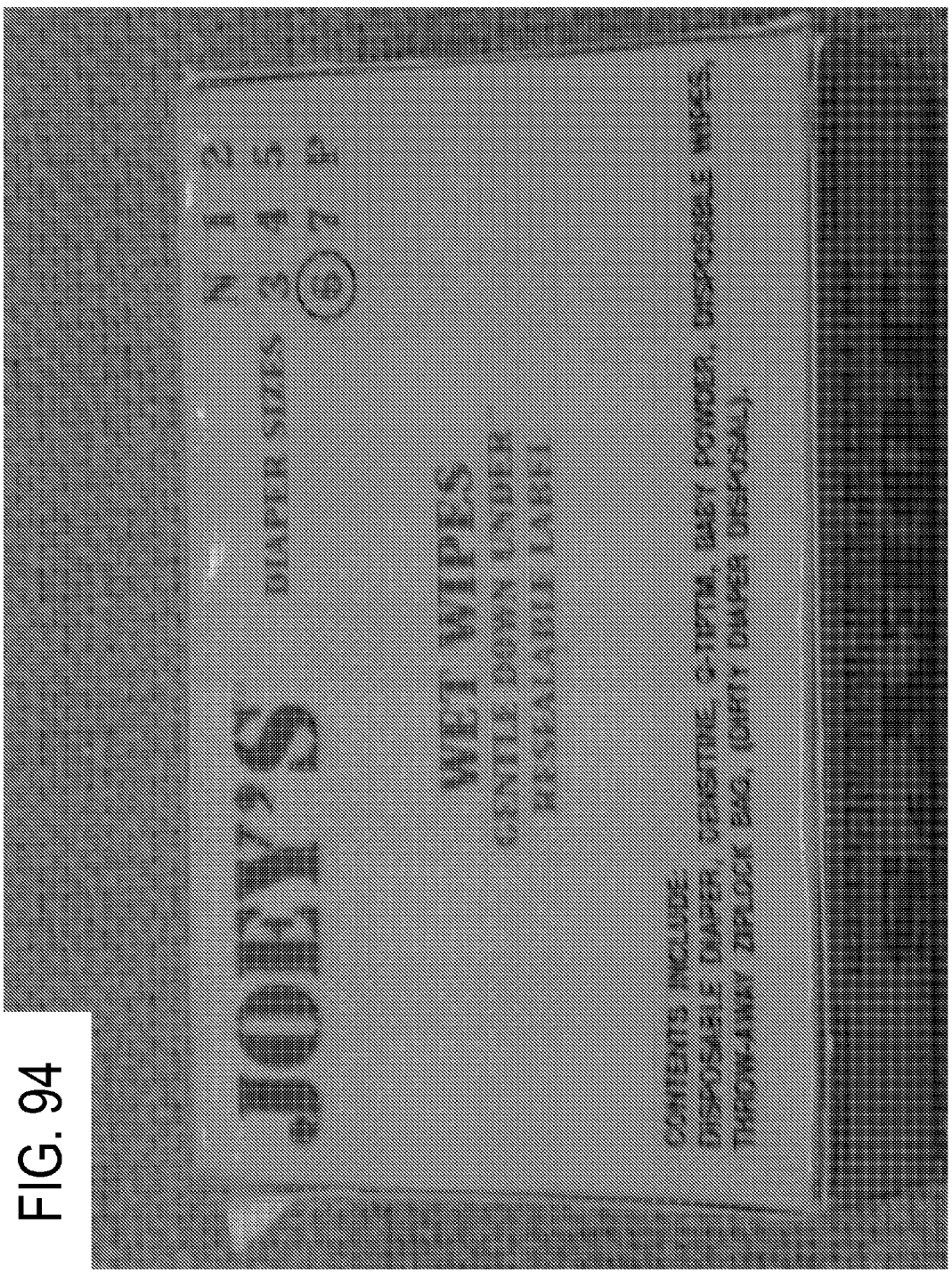
Figure 95:
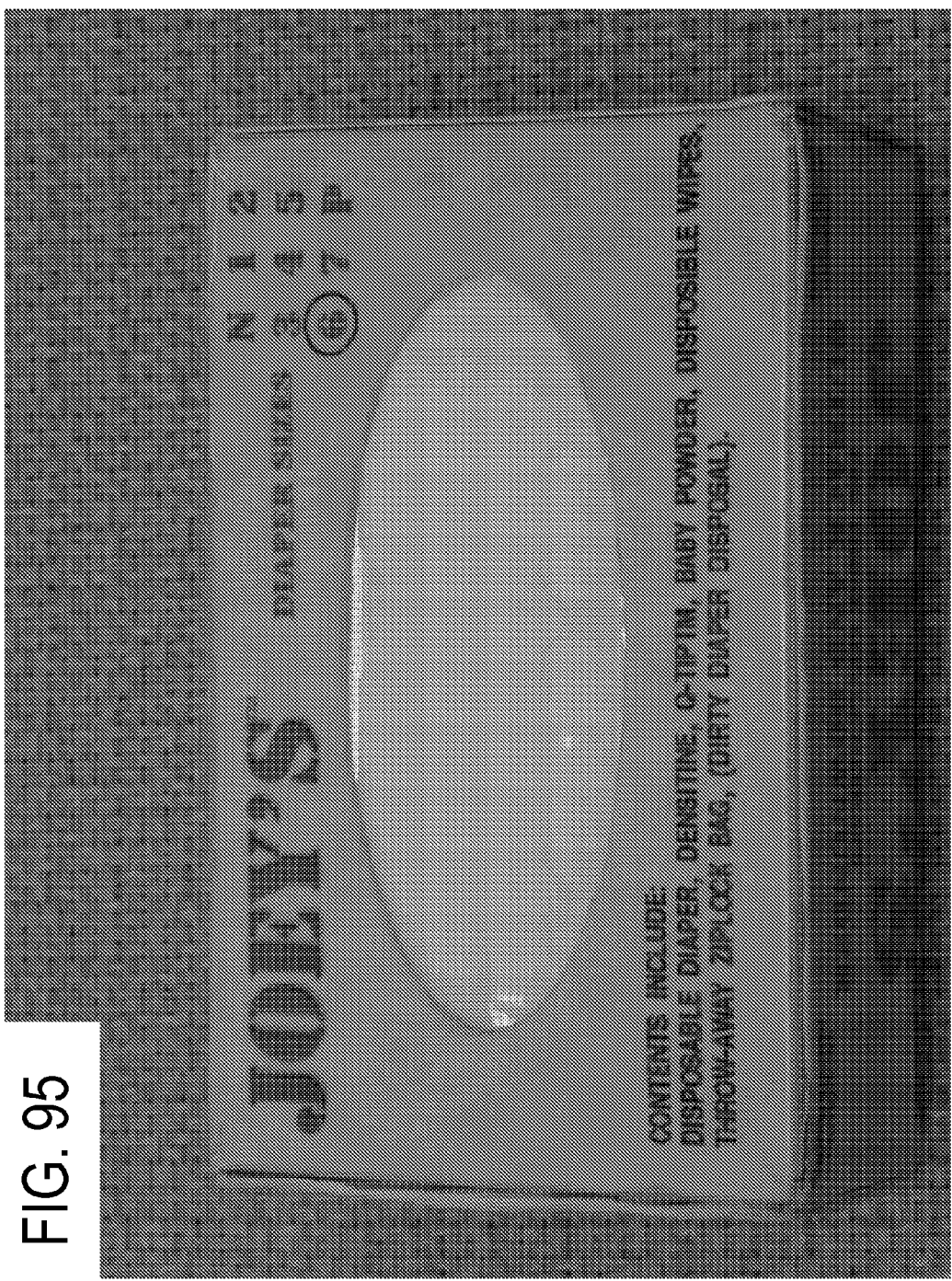
Figure 96:
Figure 97:
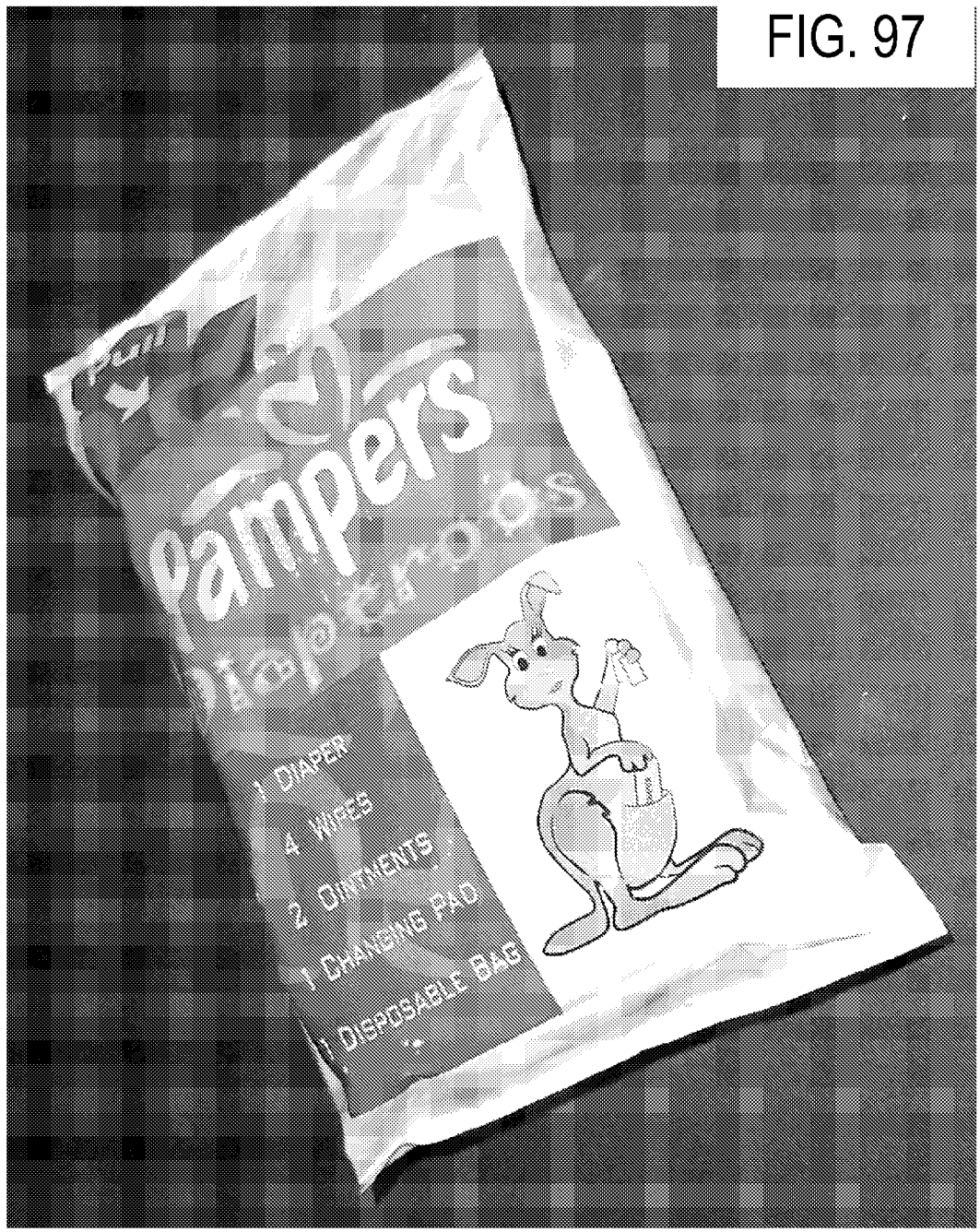
Figure 98:
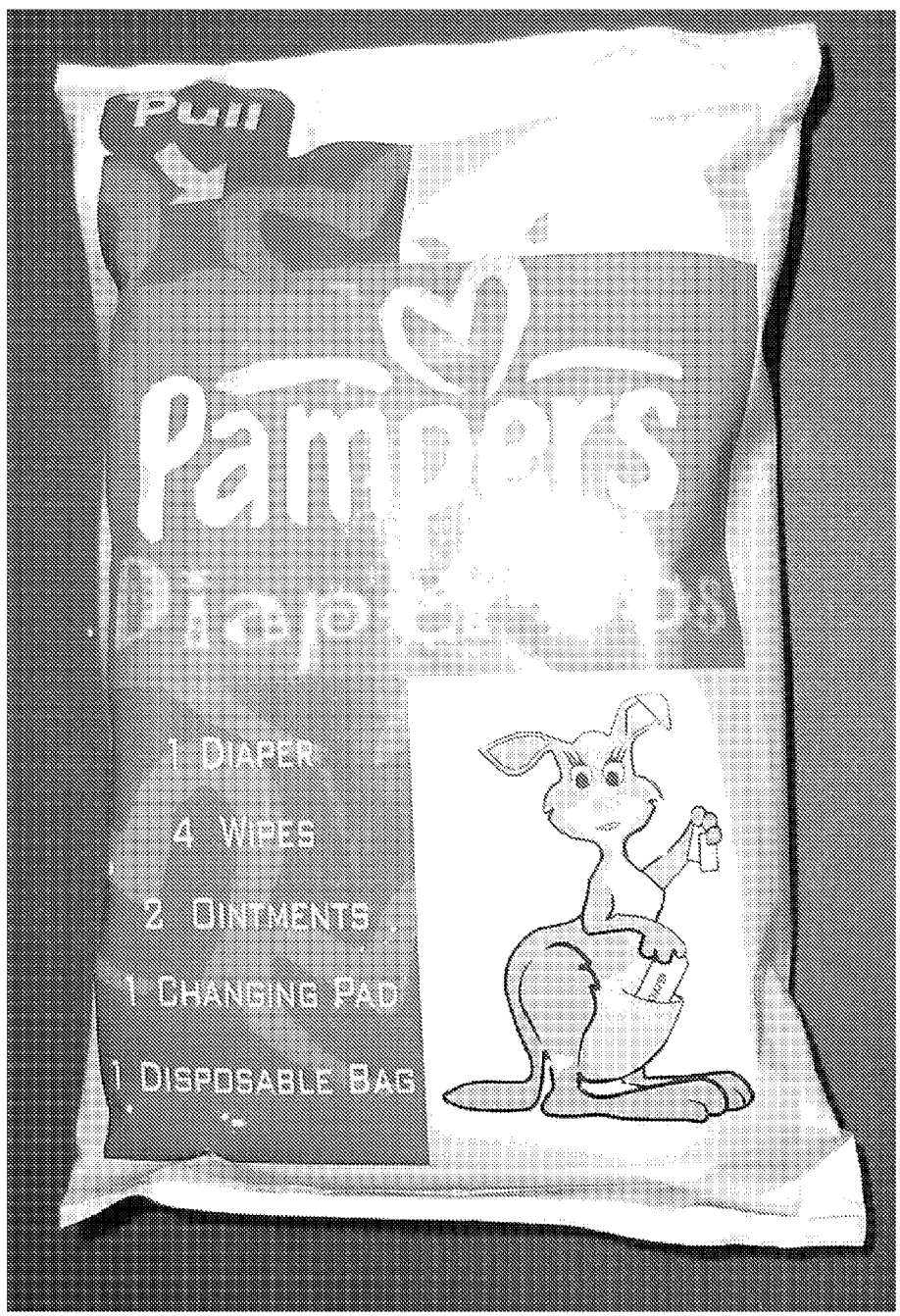
Figure 99:
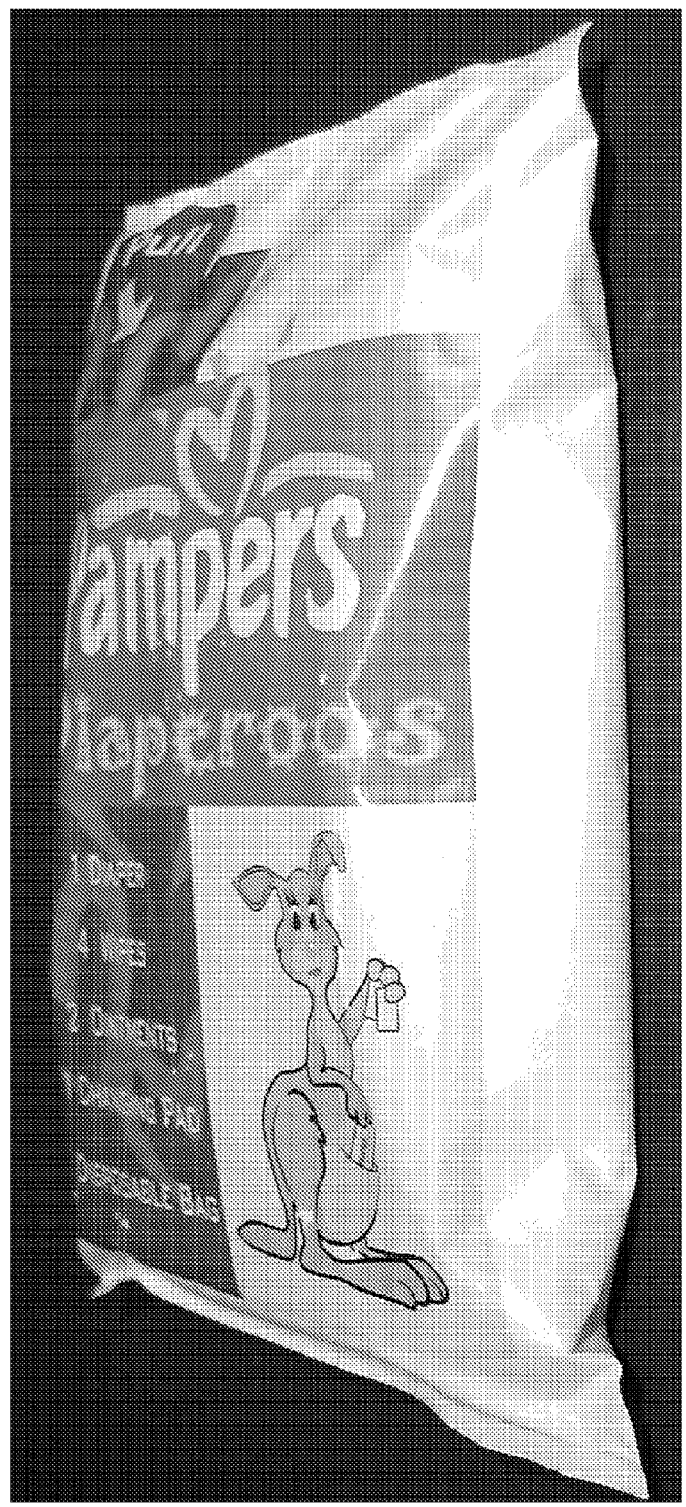
Figure 100:
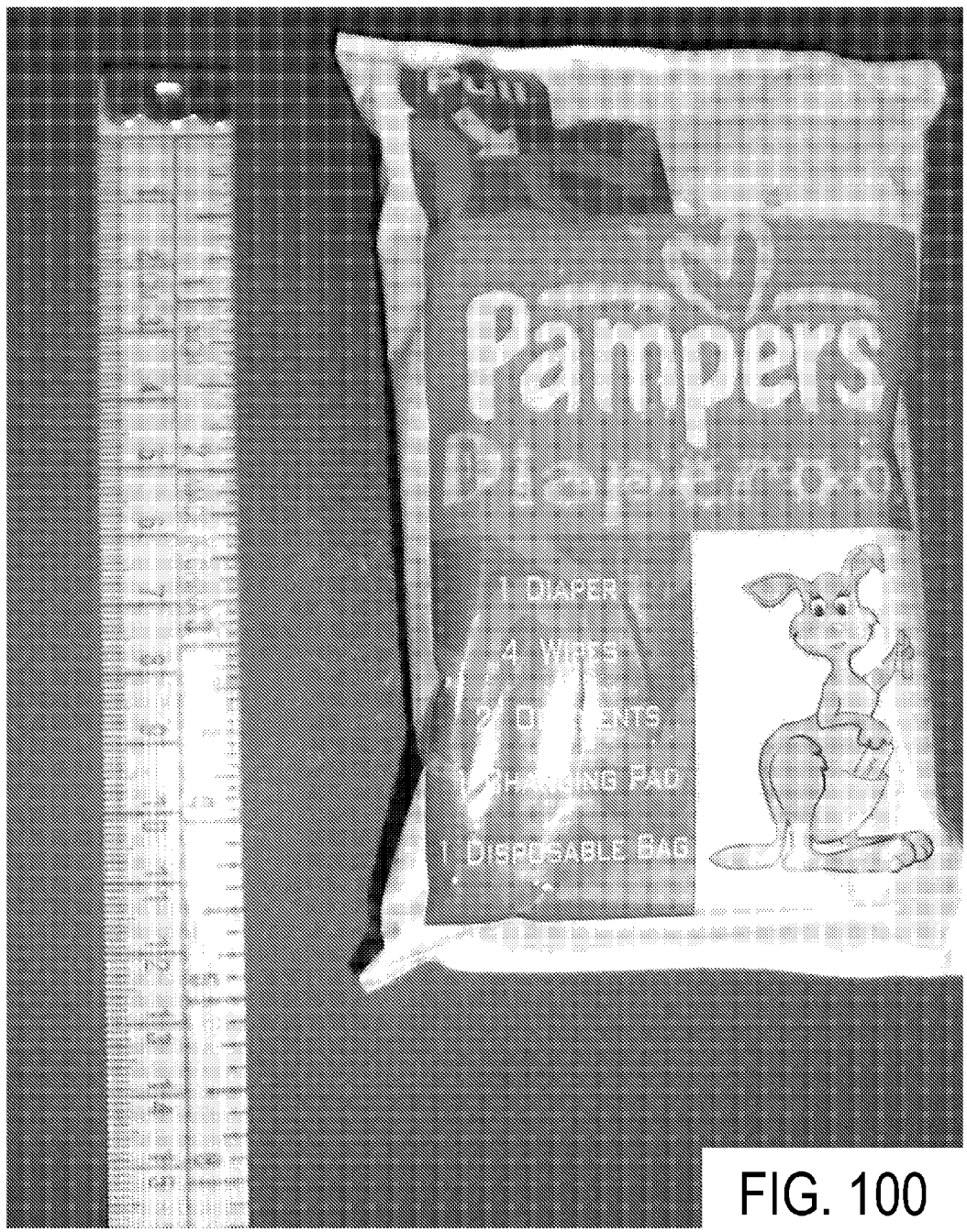
Figure 101:
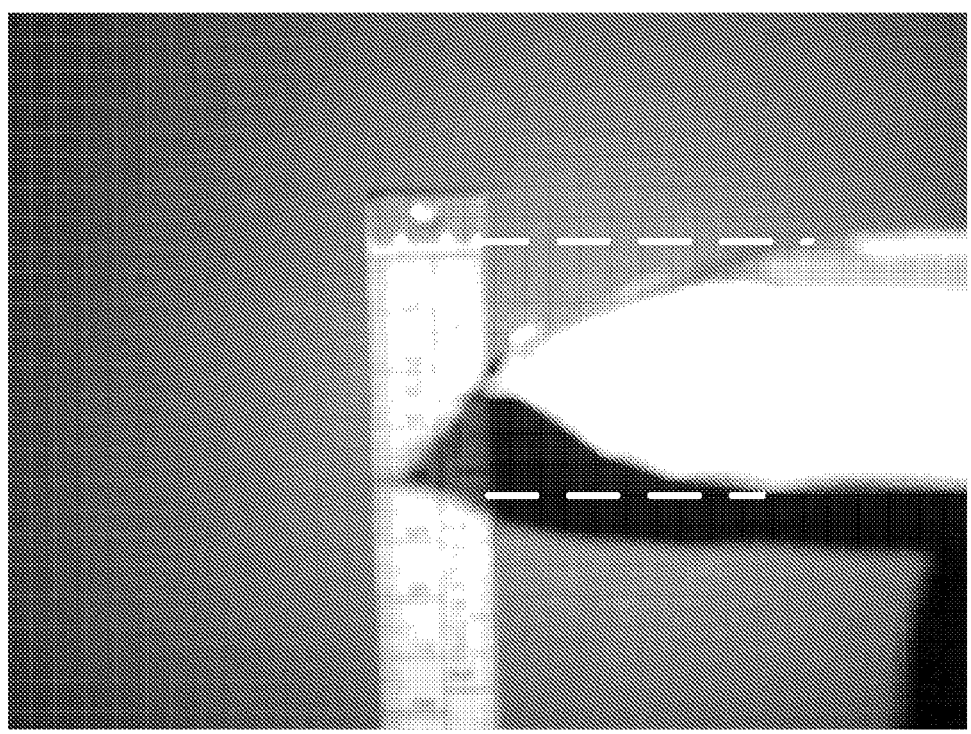
Figure 102:
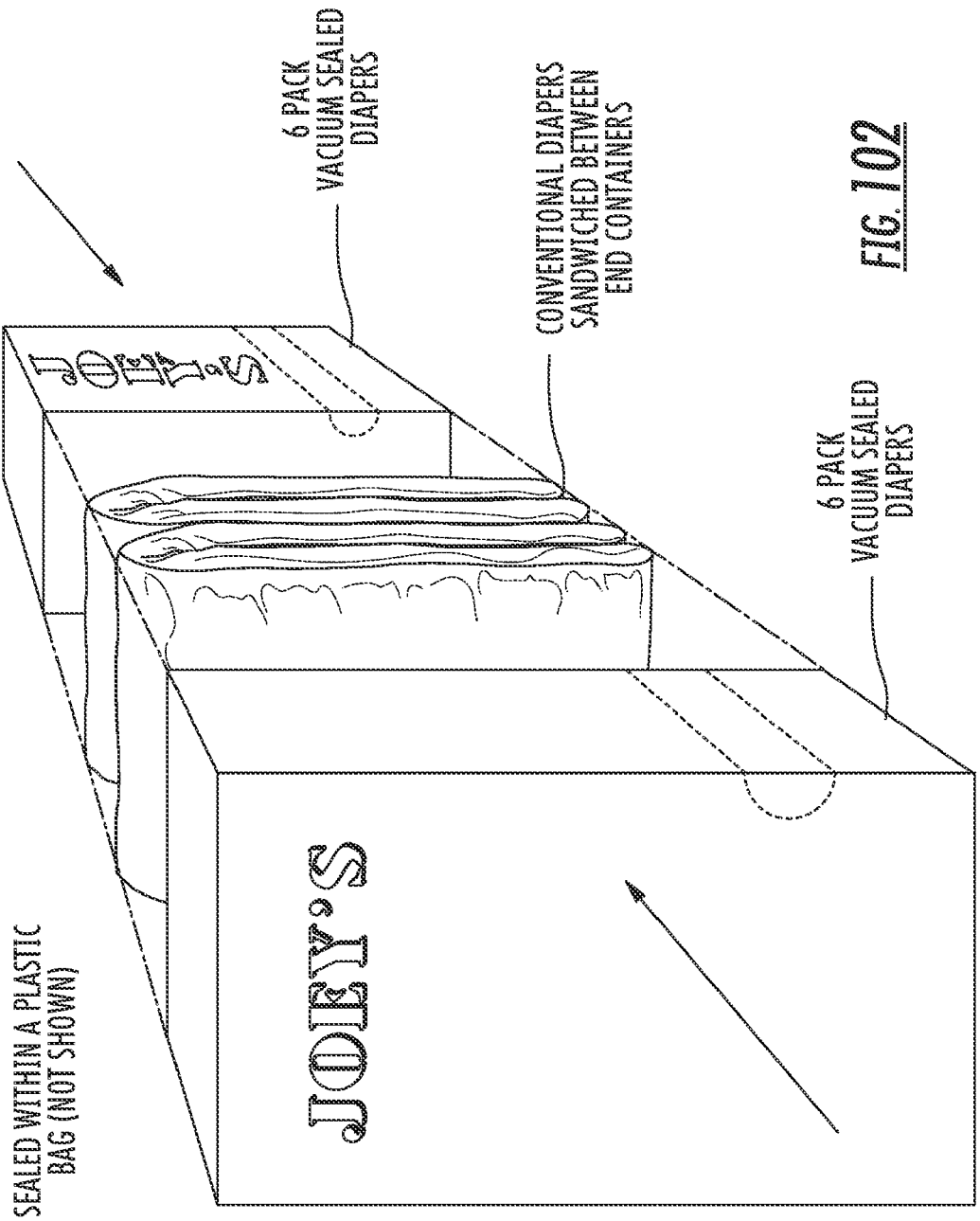
Figure 103:
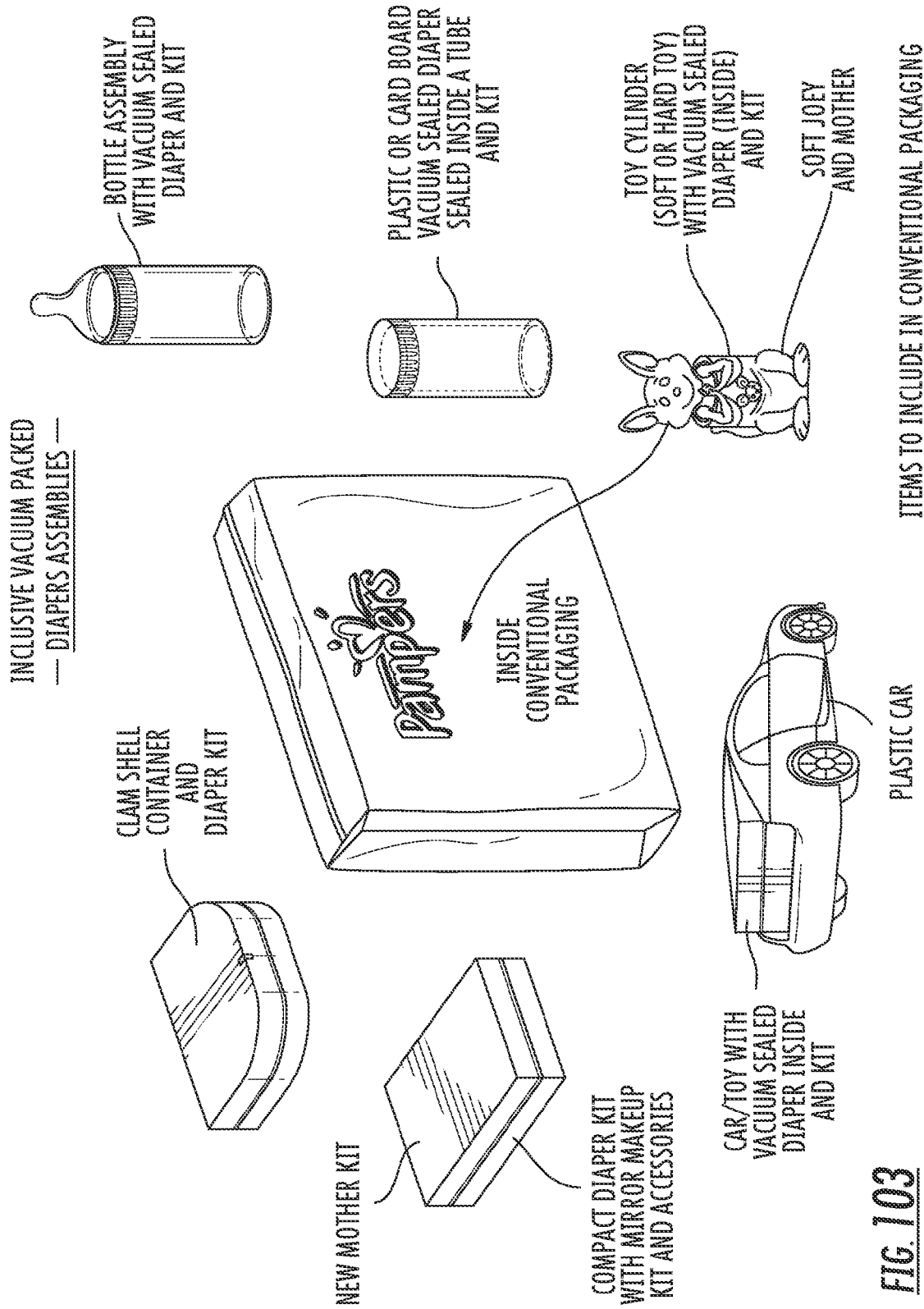
Figure 104:
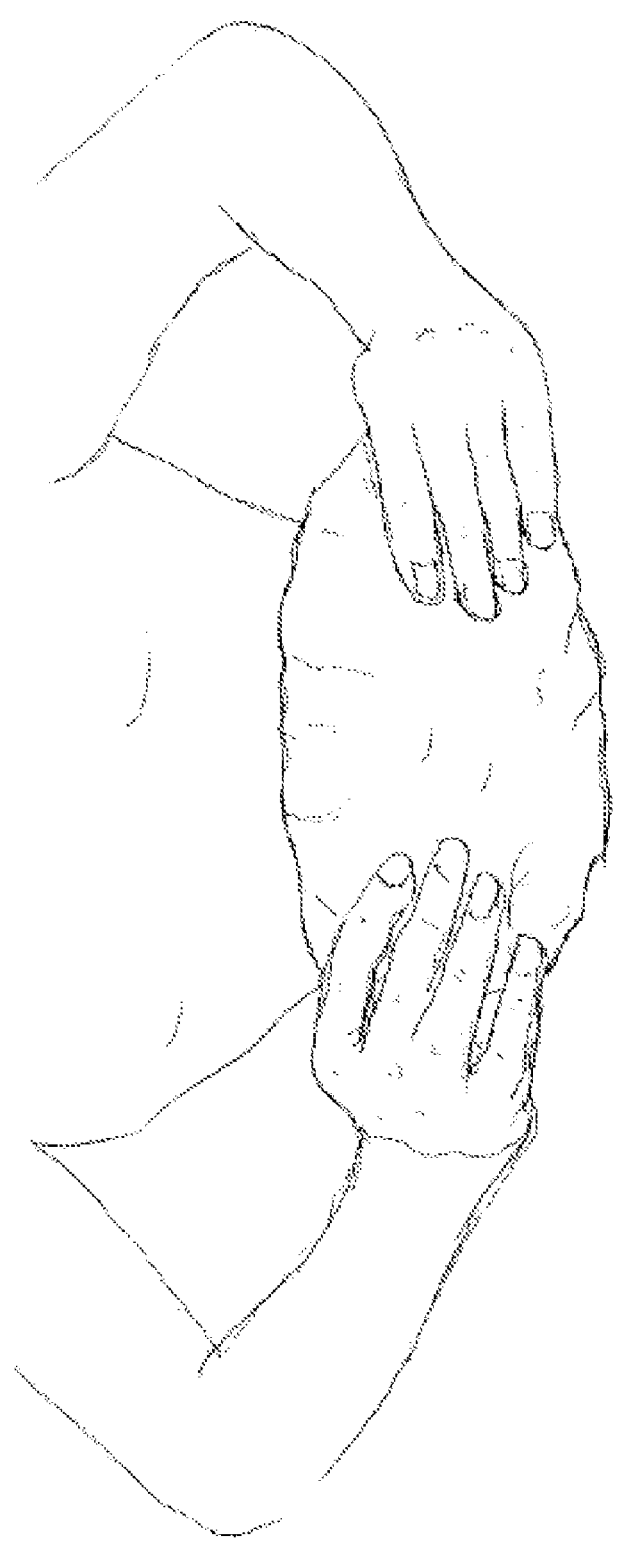
Figure 105:
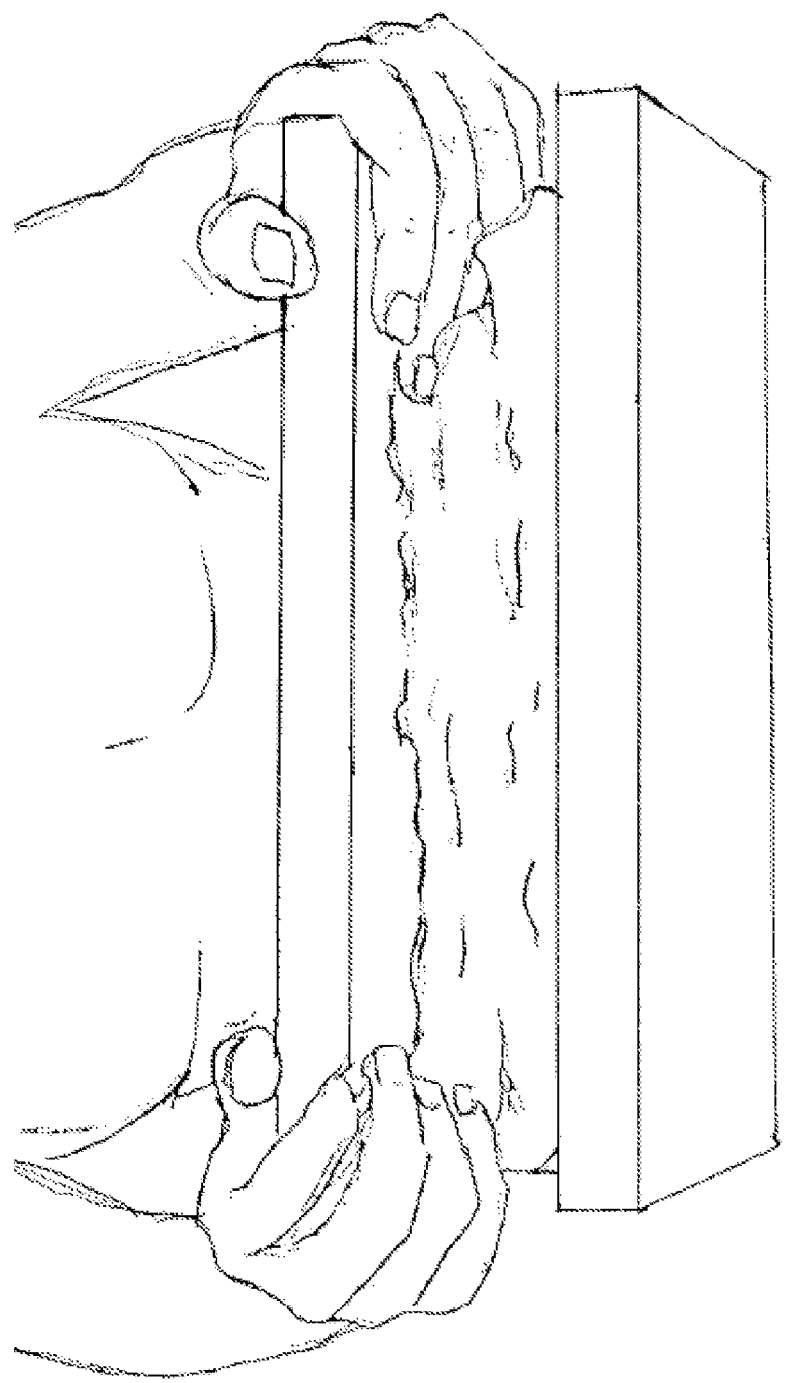
Figure 106:
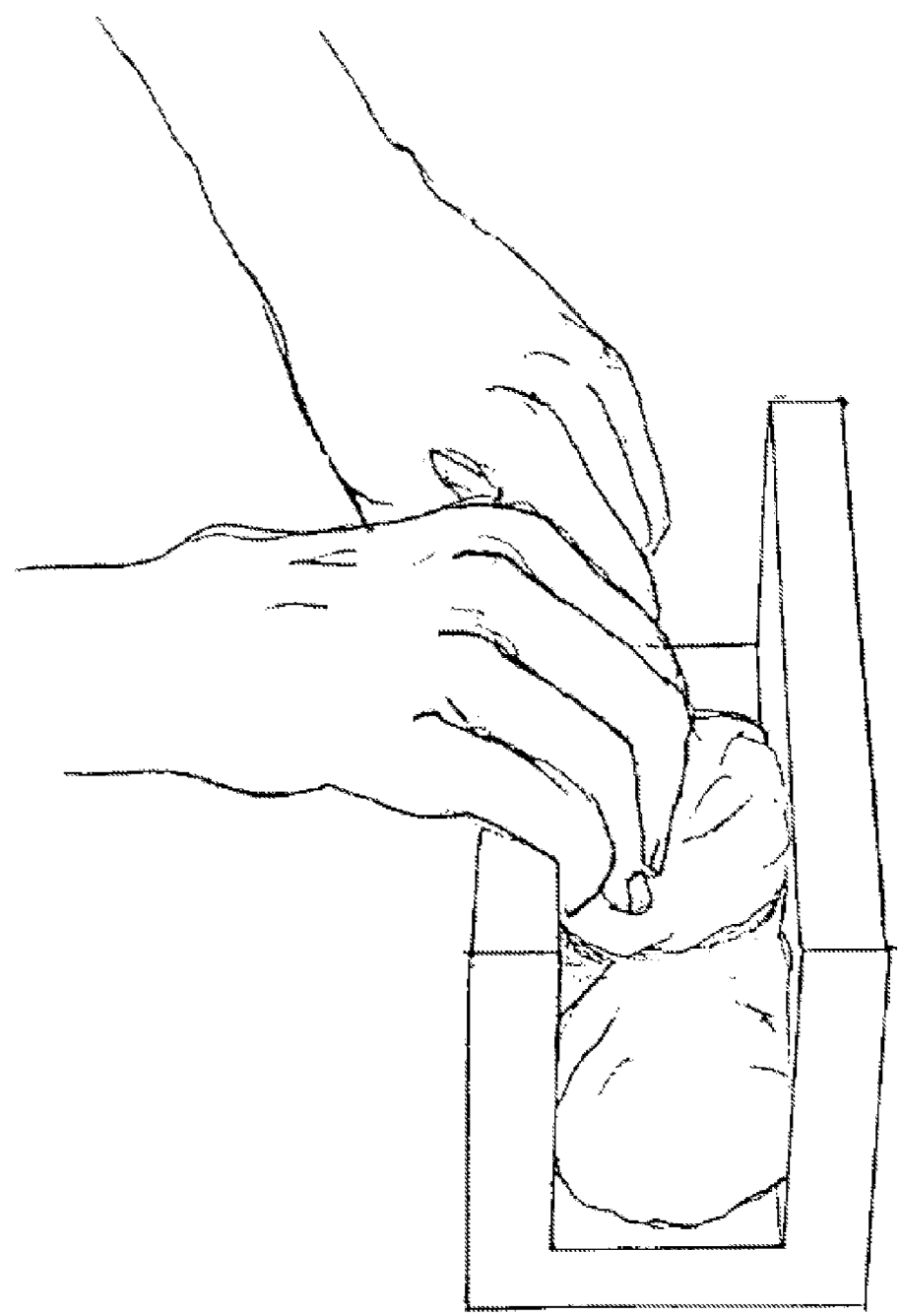
Figure 107:
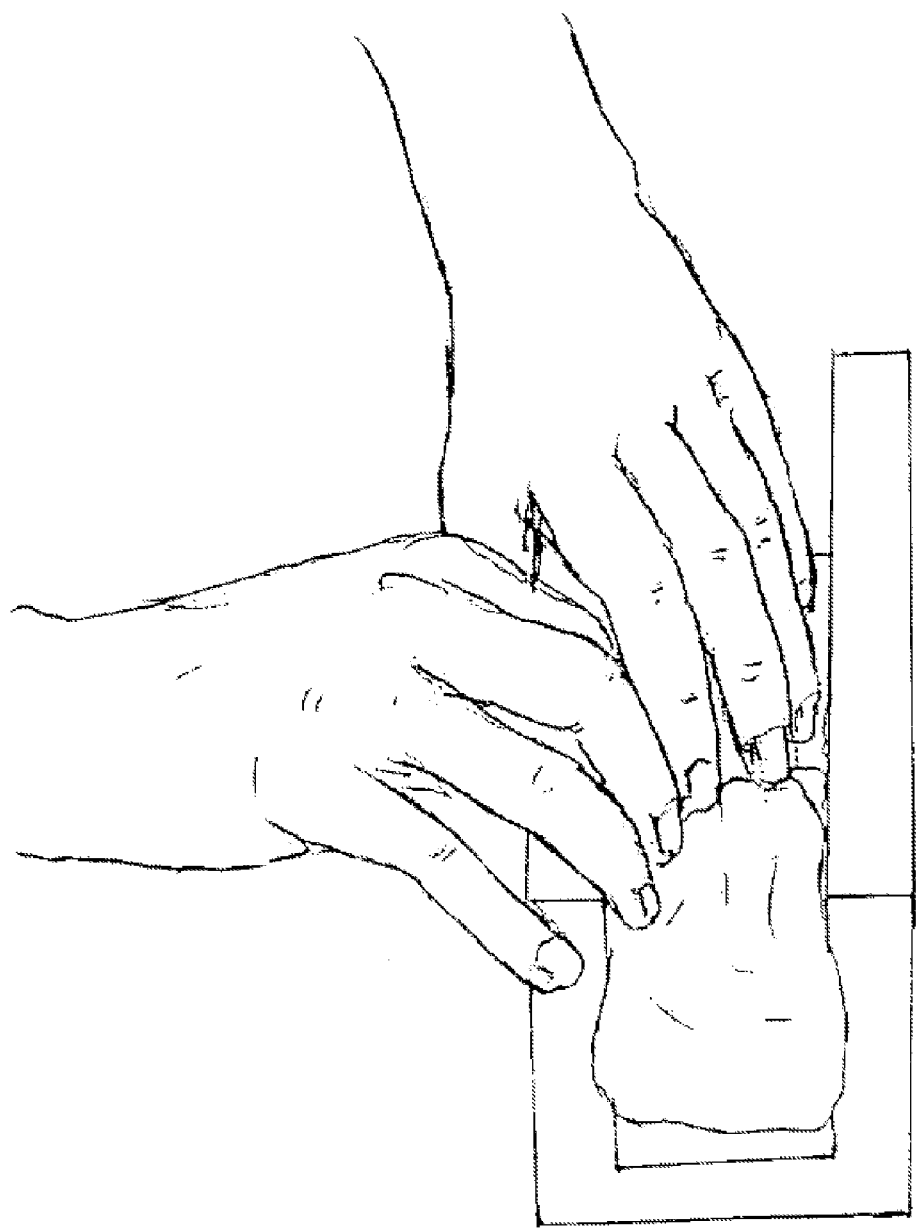
Figure 108:
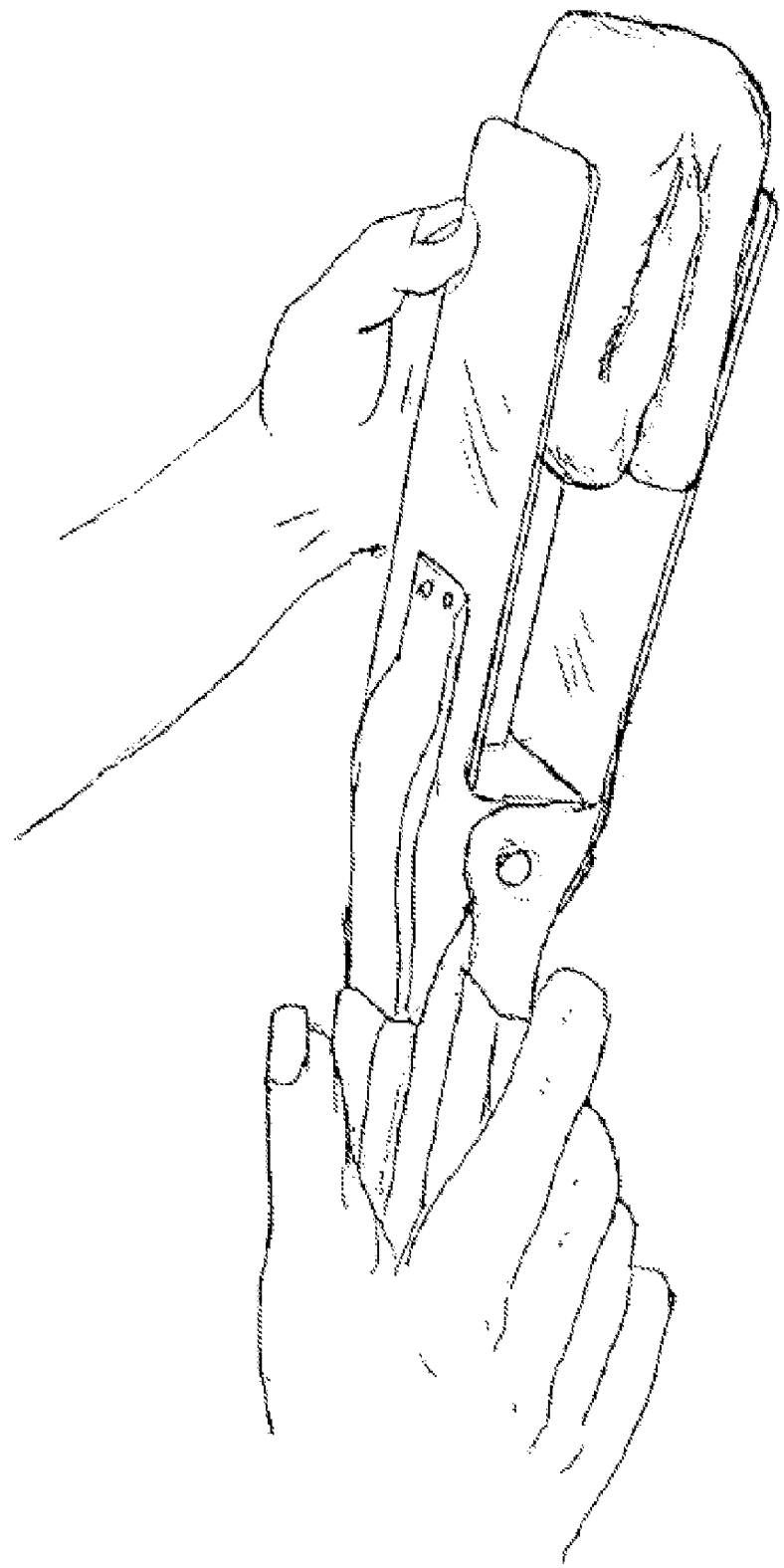
Figure 109:
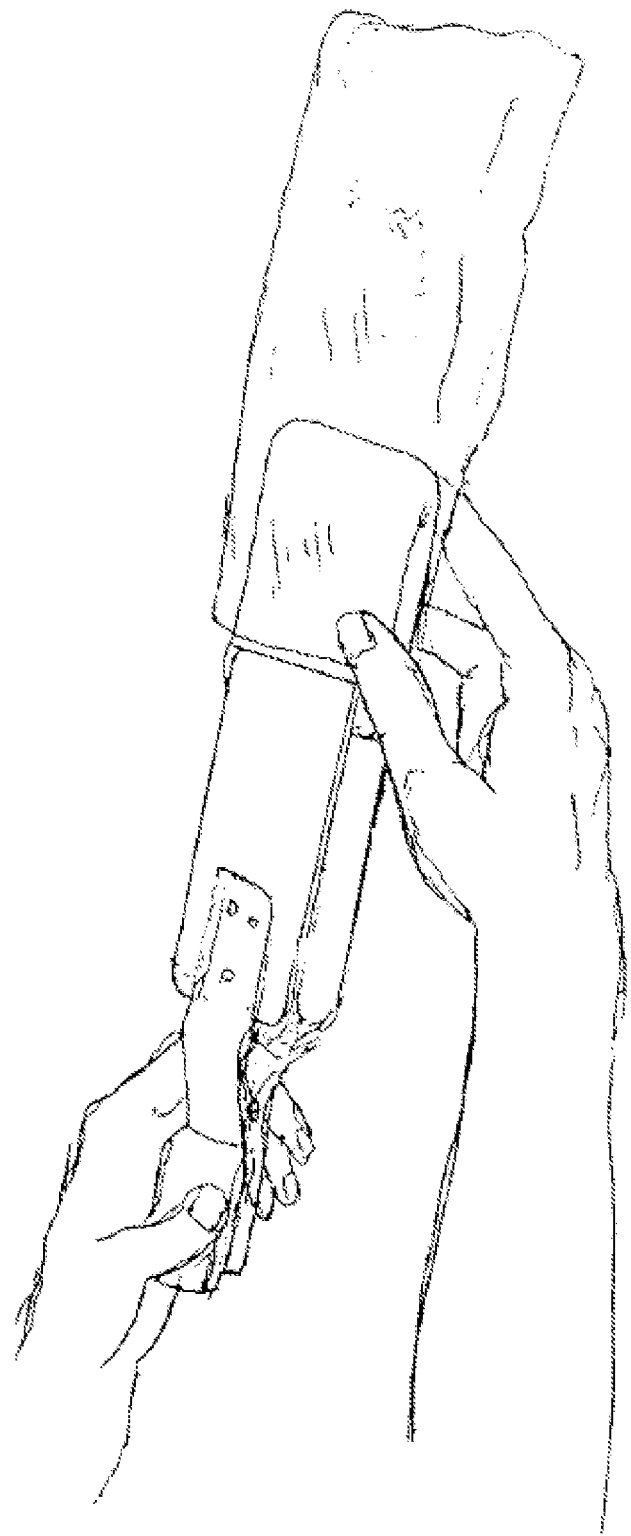
Figure 110:
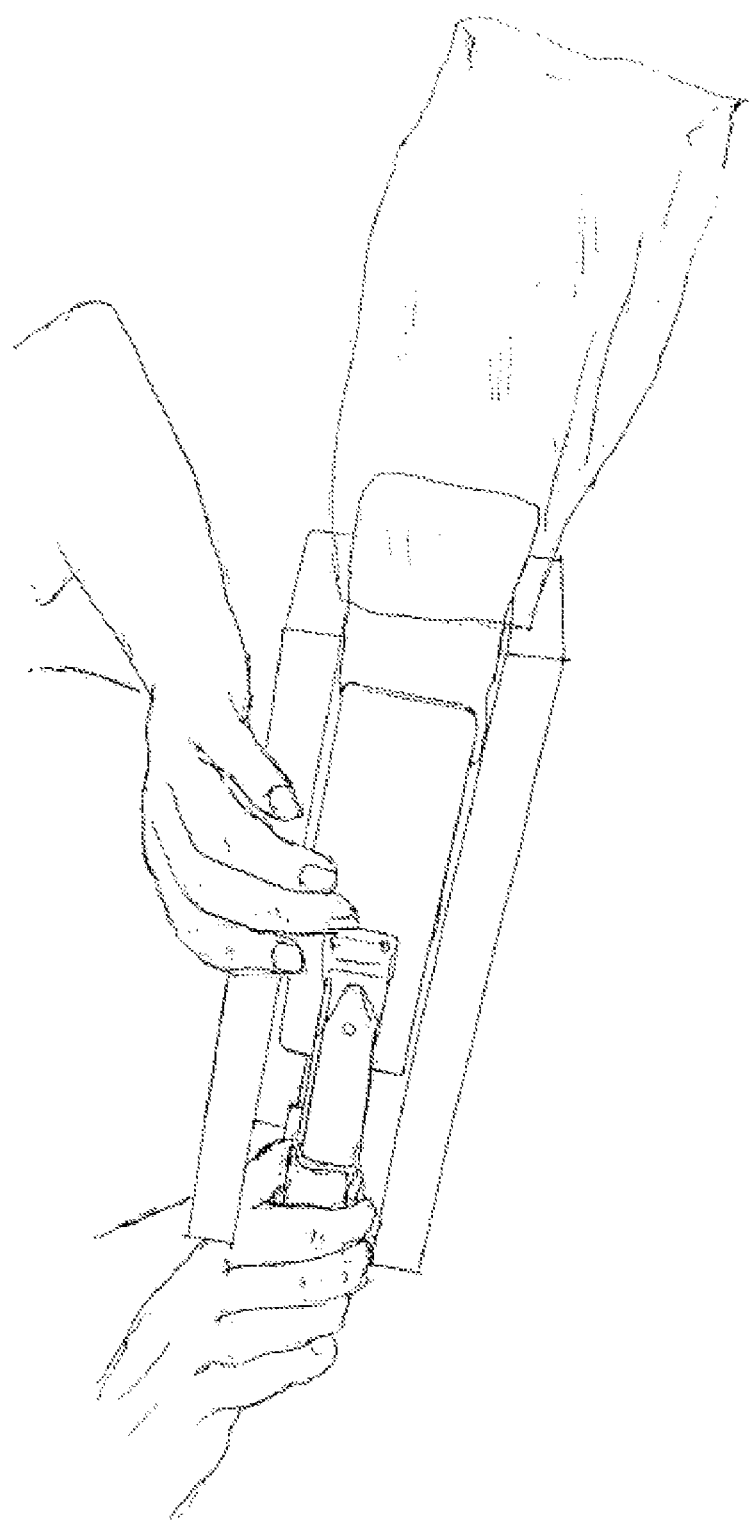
Figure 111:
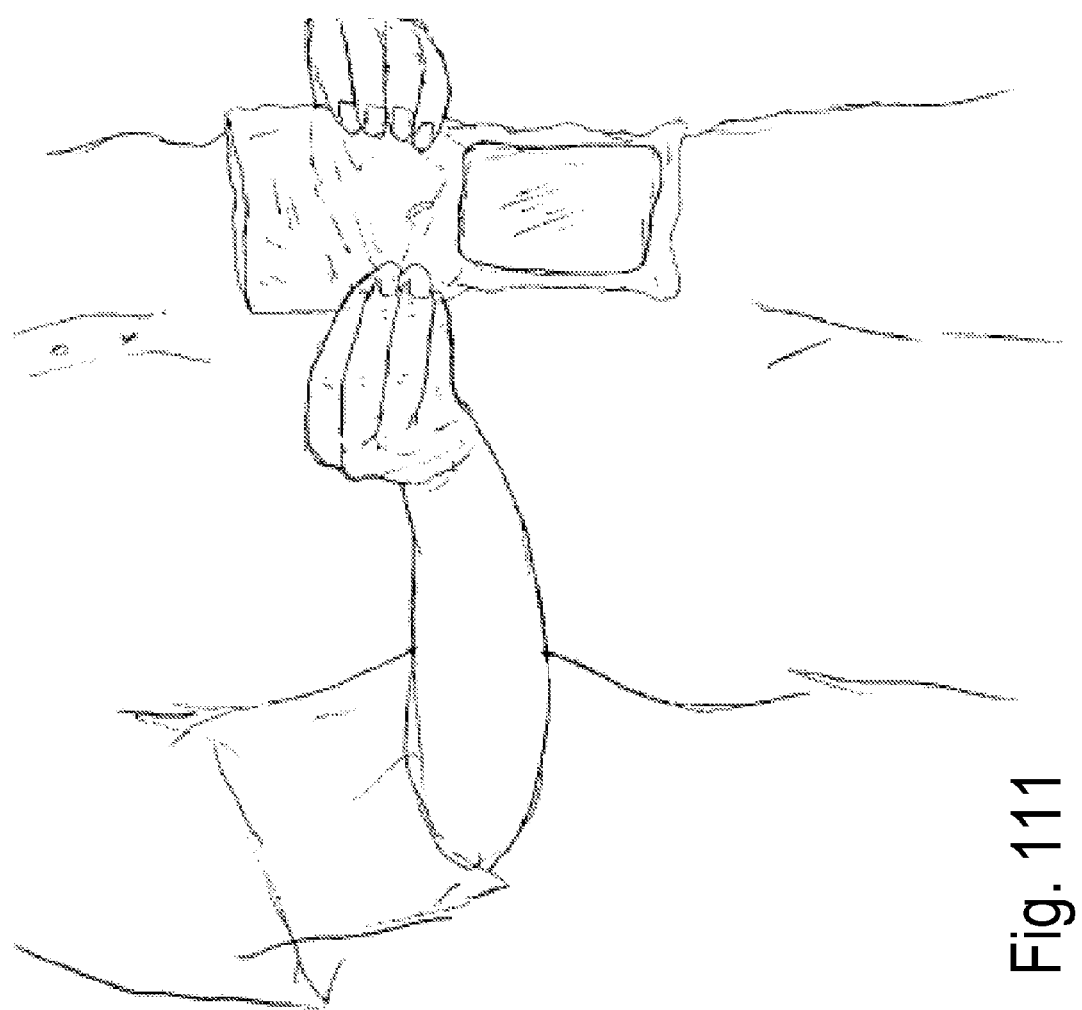
Figure 112:
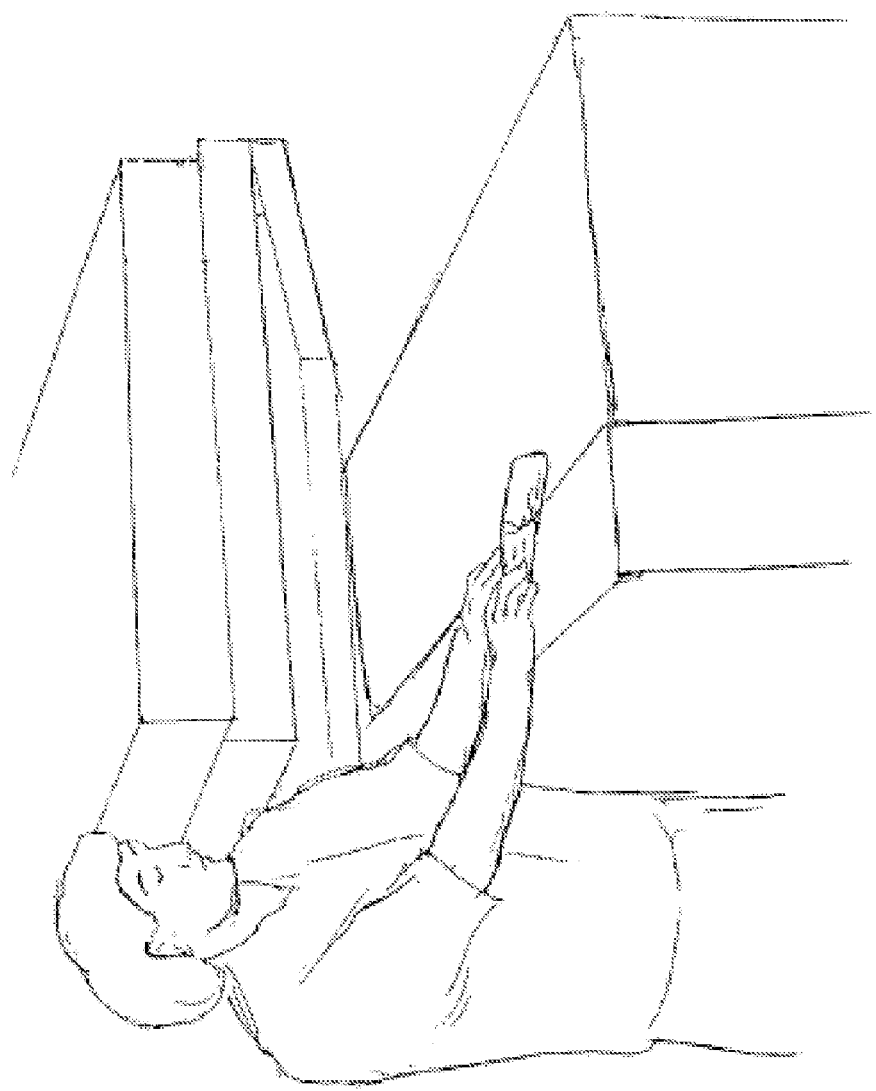
Figure 113:
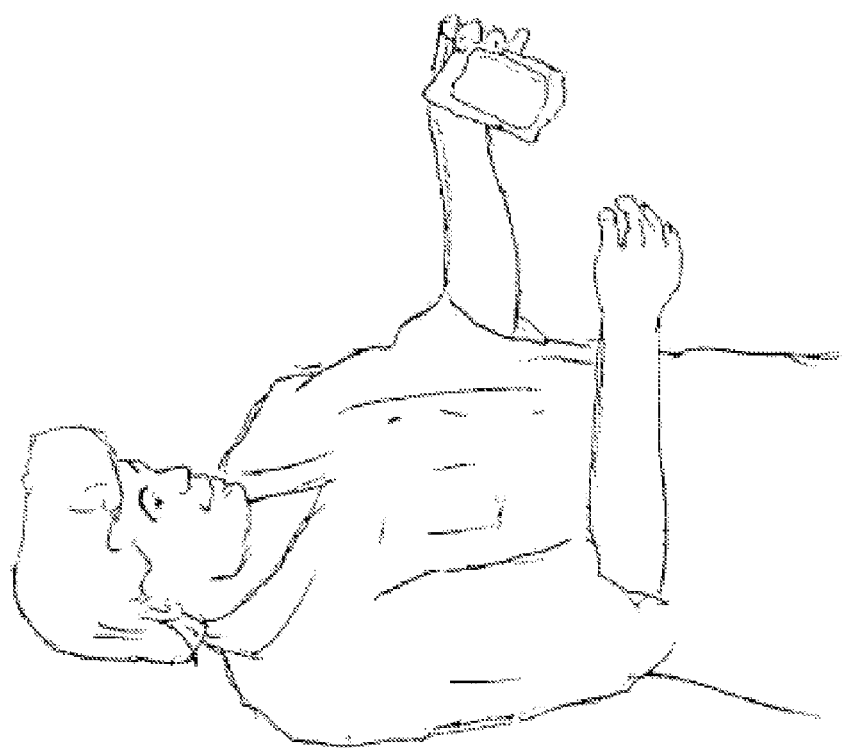
Figure 114:
Figure 115:
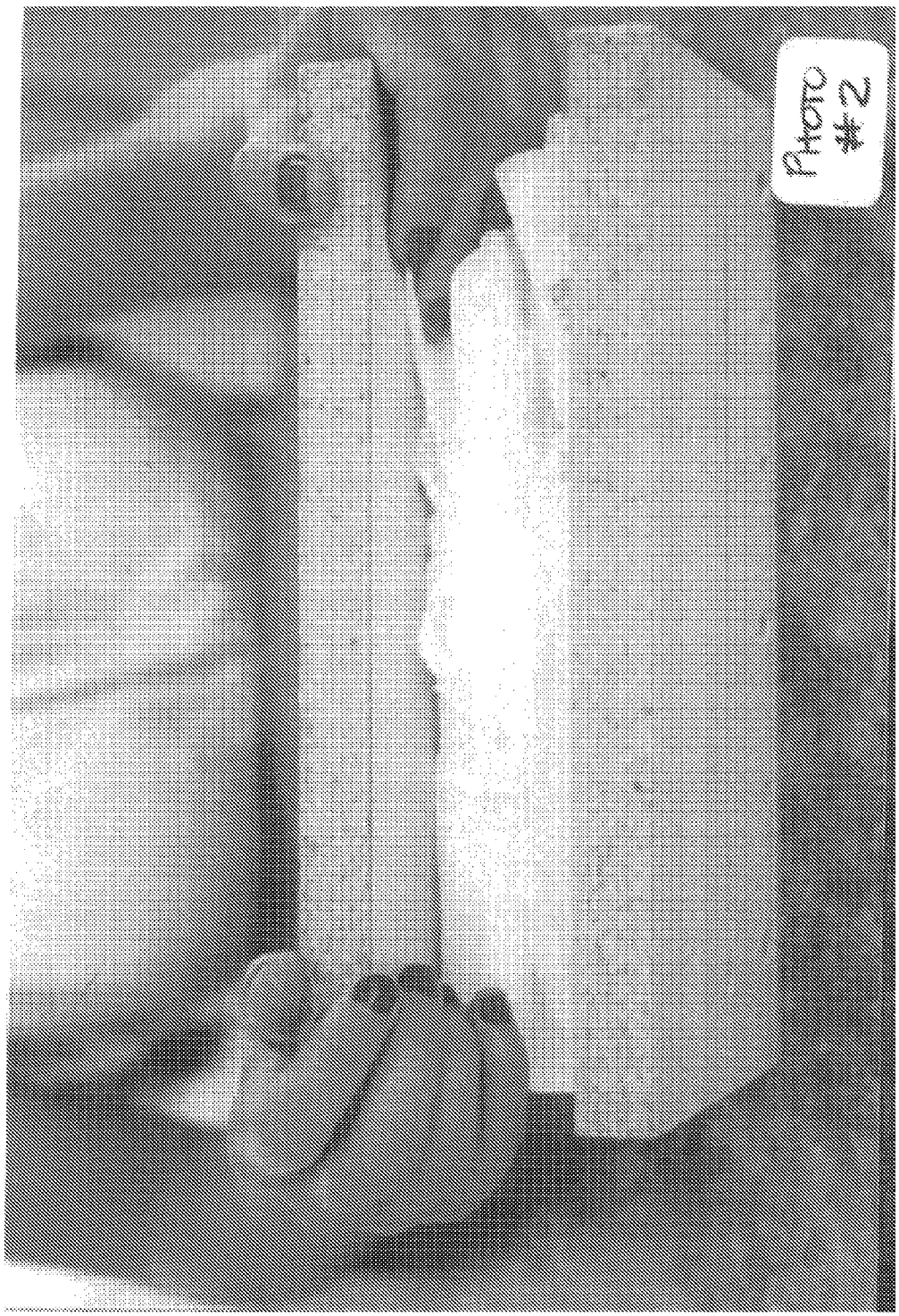
Figure 116:
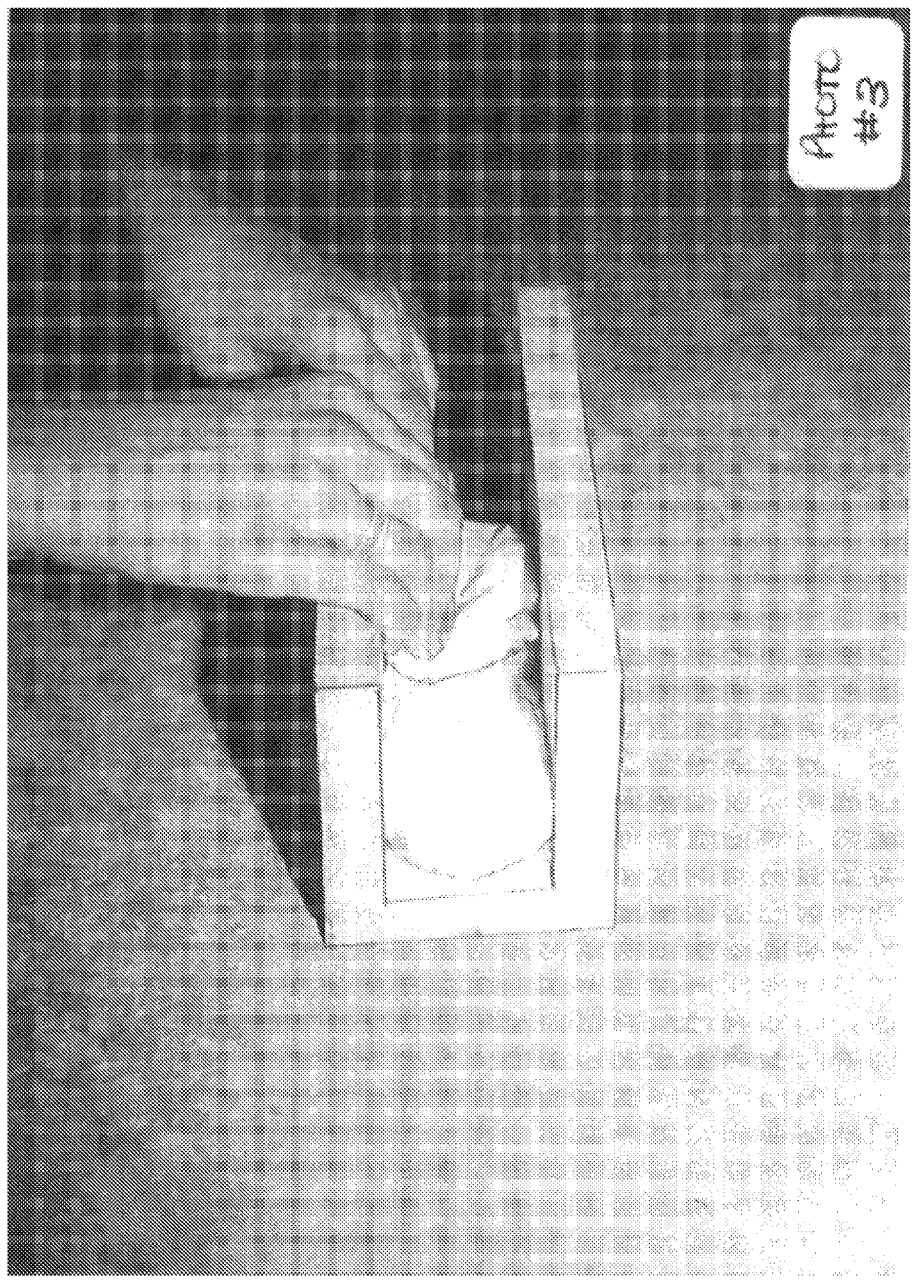
Figure 117:
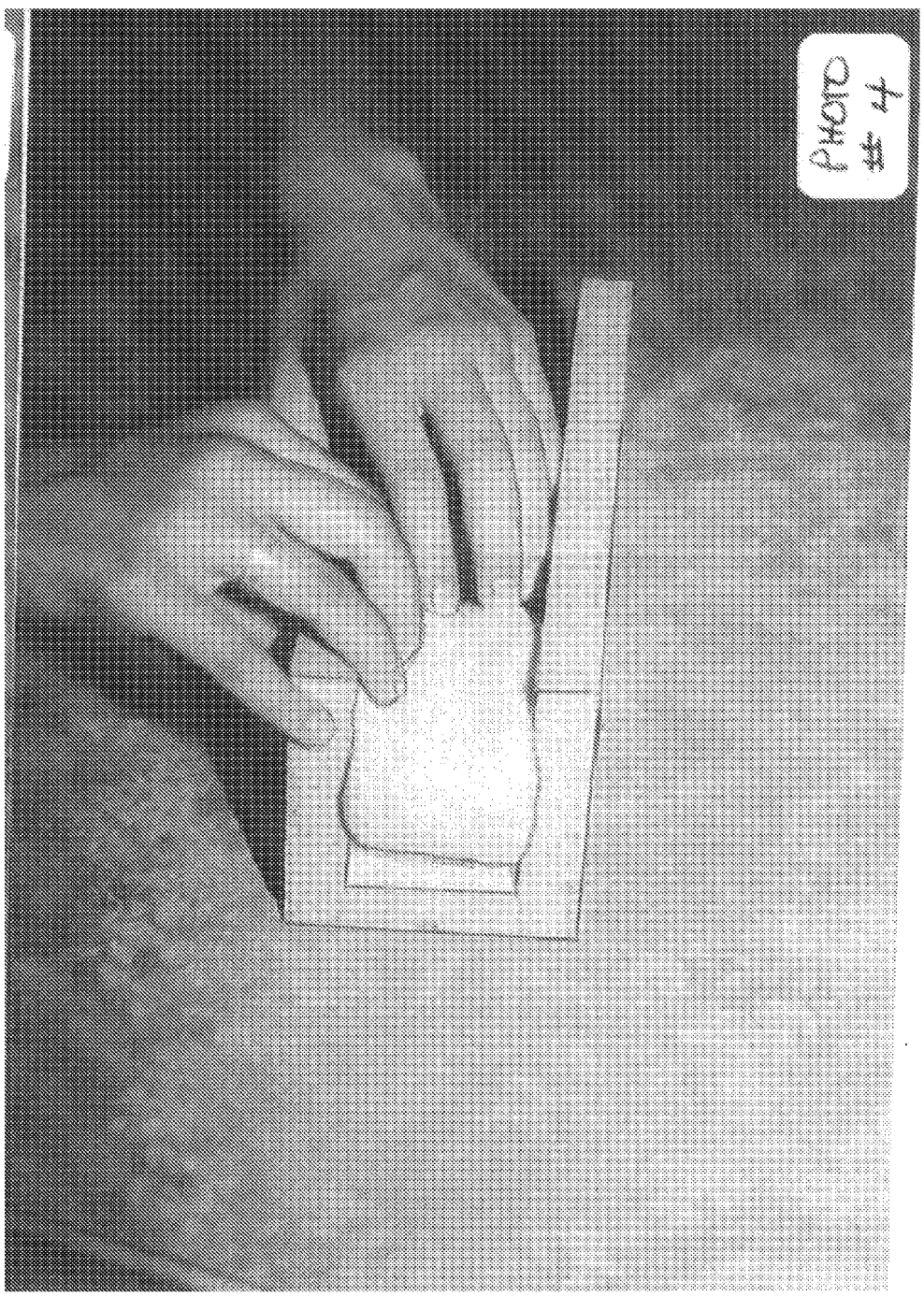
Figure 118:
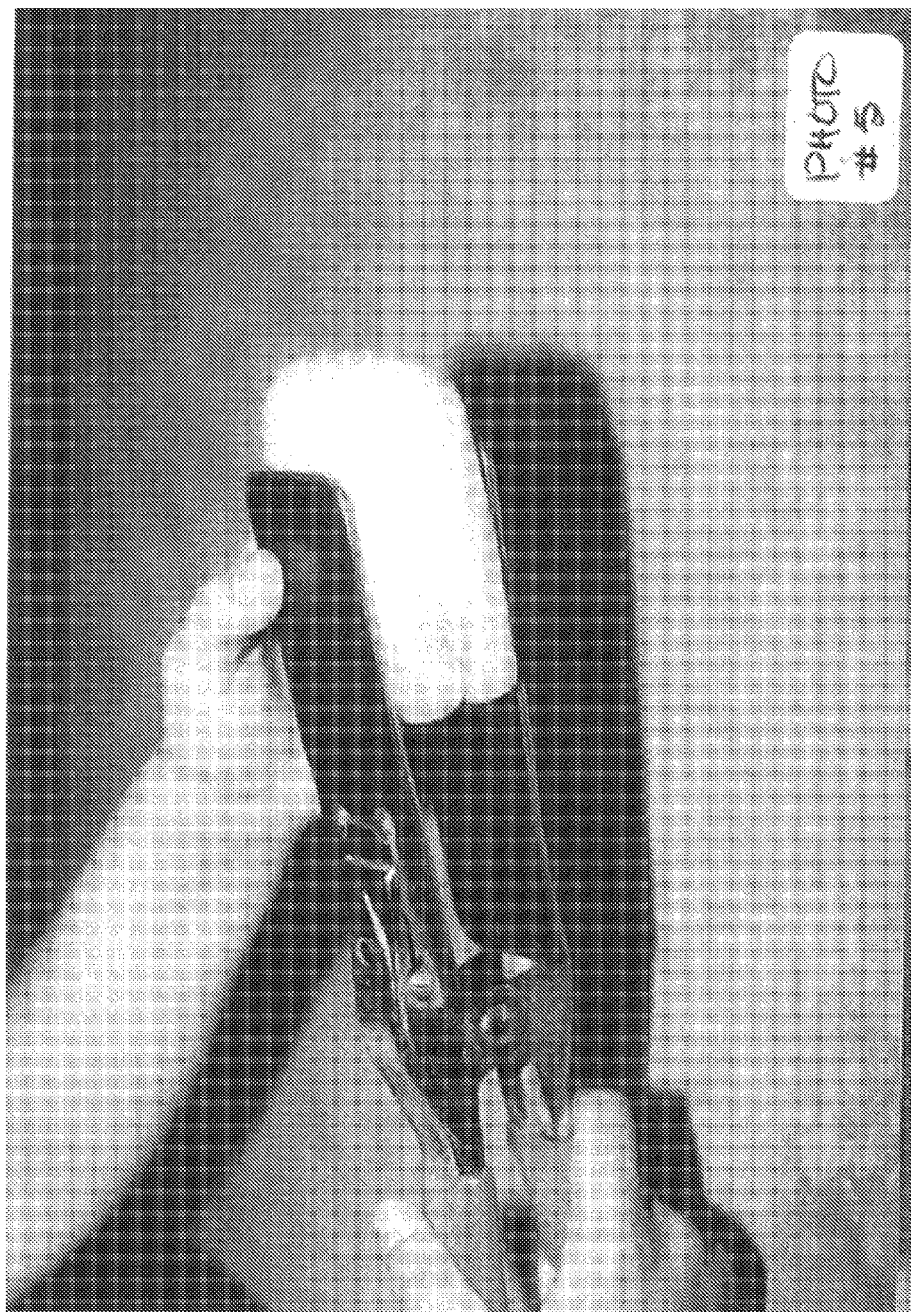
Figure 119:
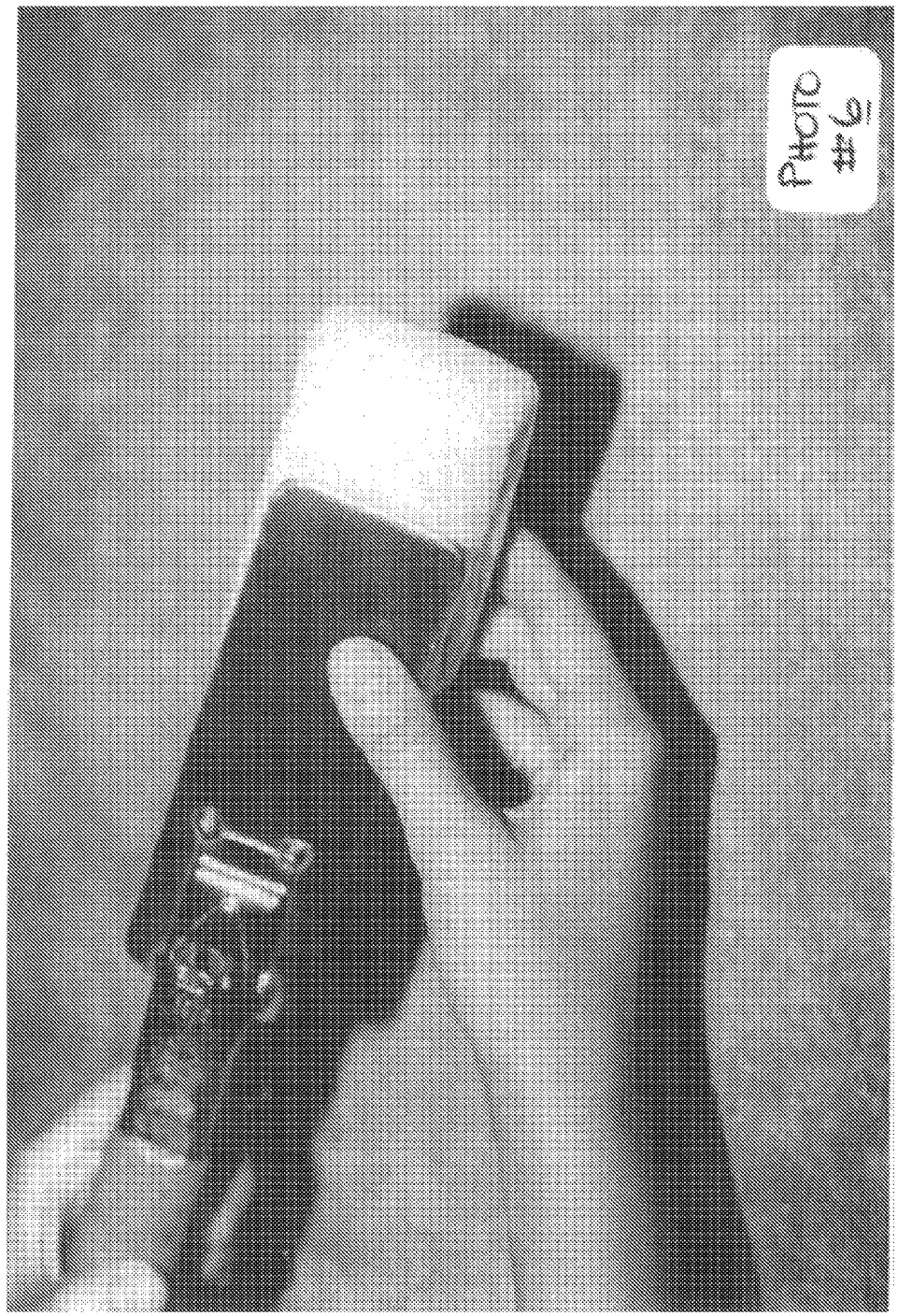
Figure 120:
Figure 121:
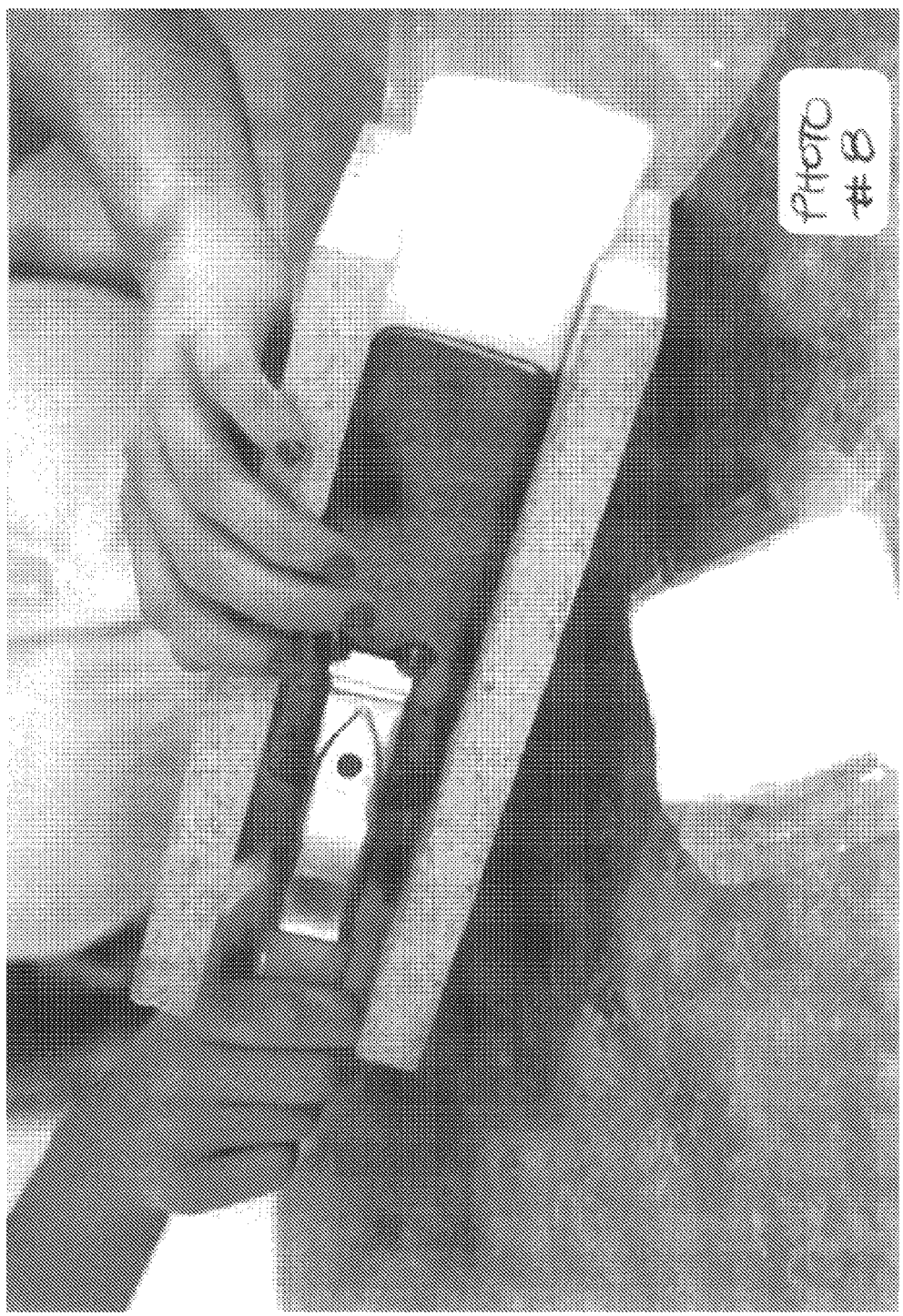
Figure 122:
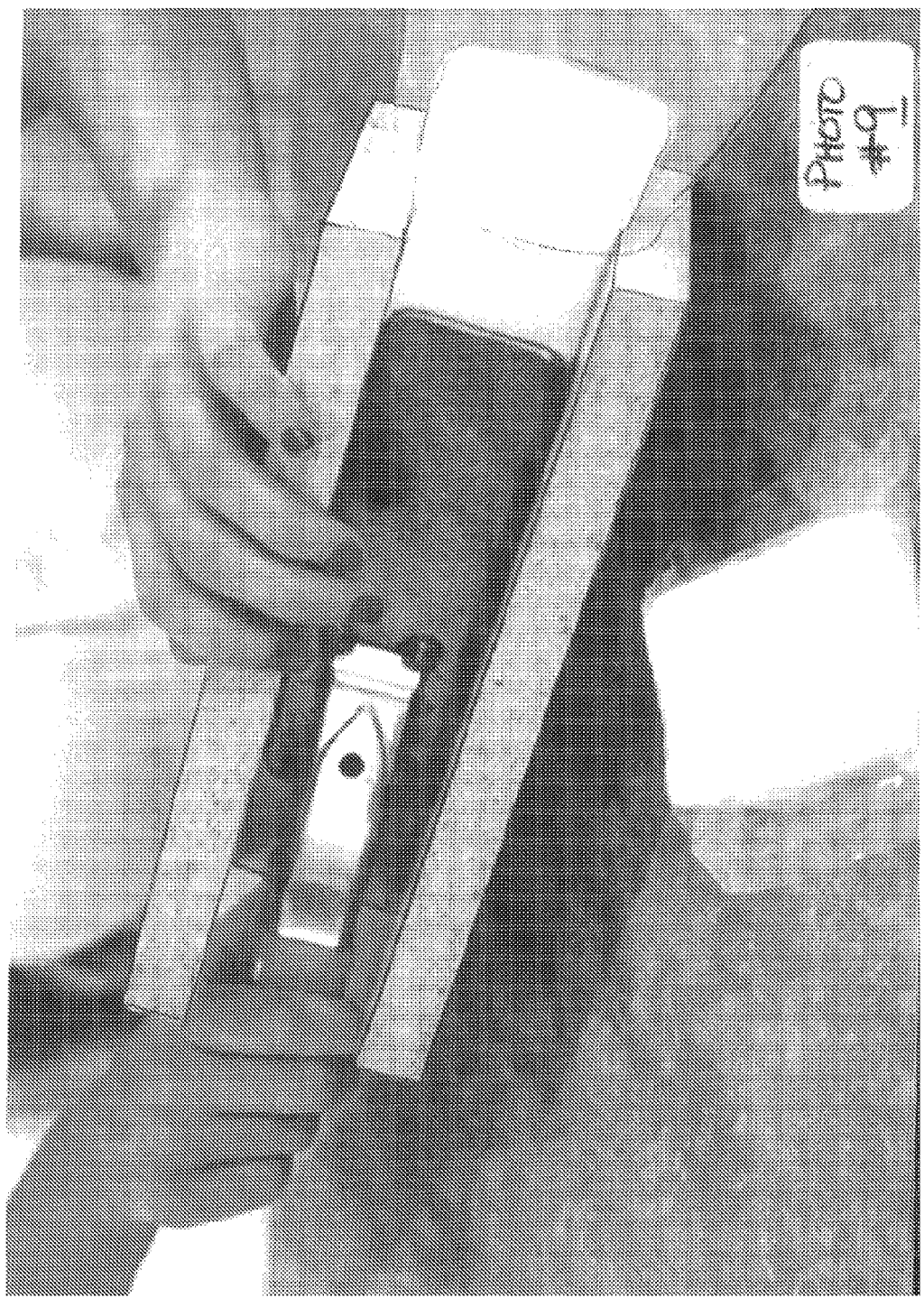
Figure 123:
Figure 124:
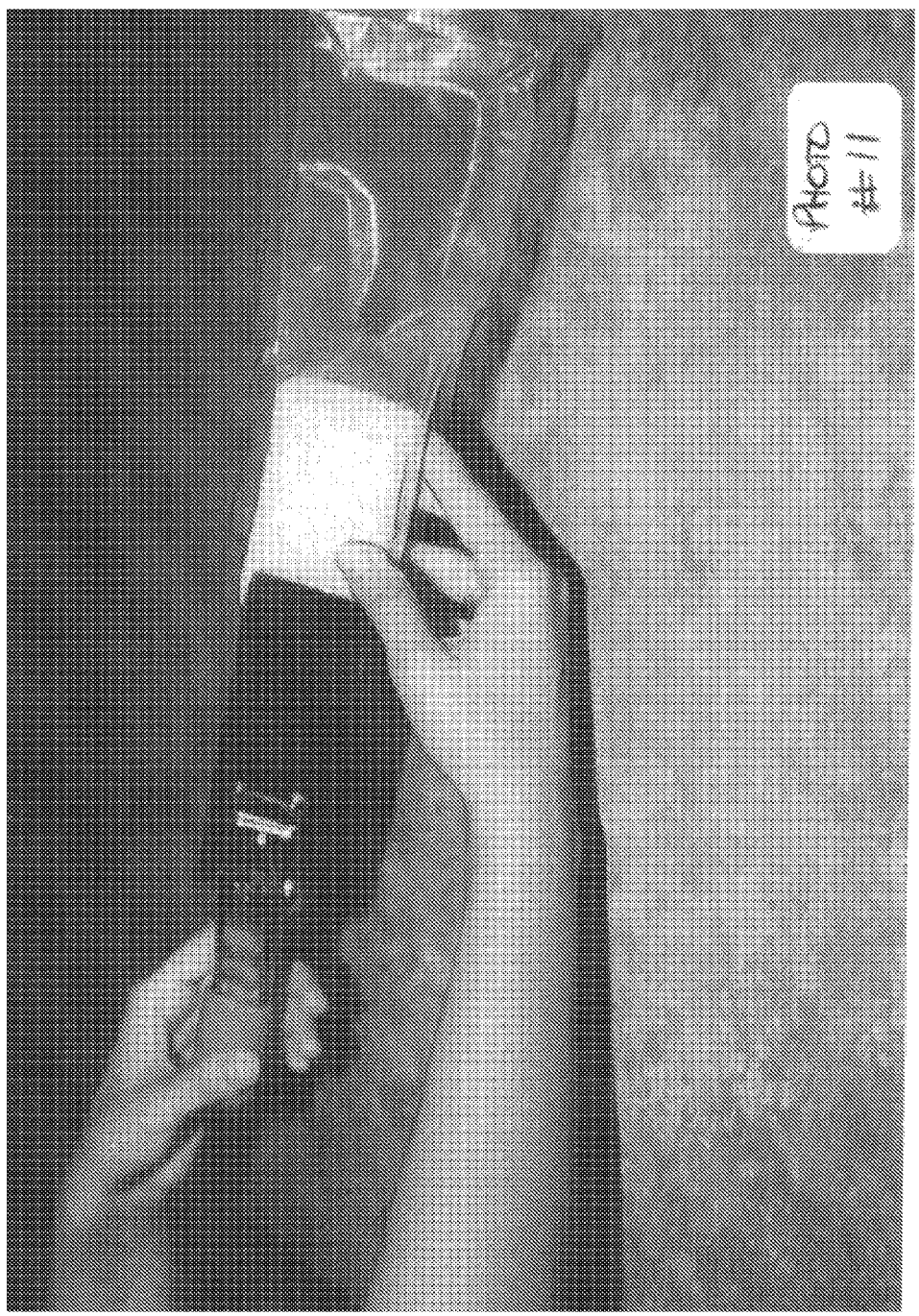
Figure 125:
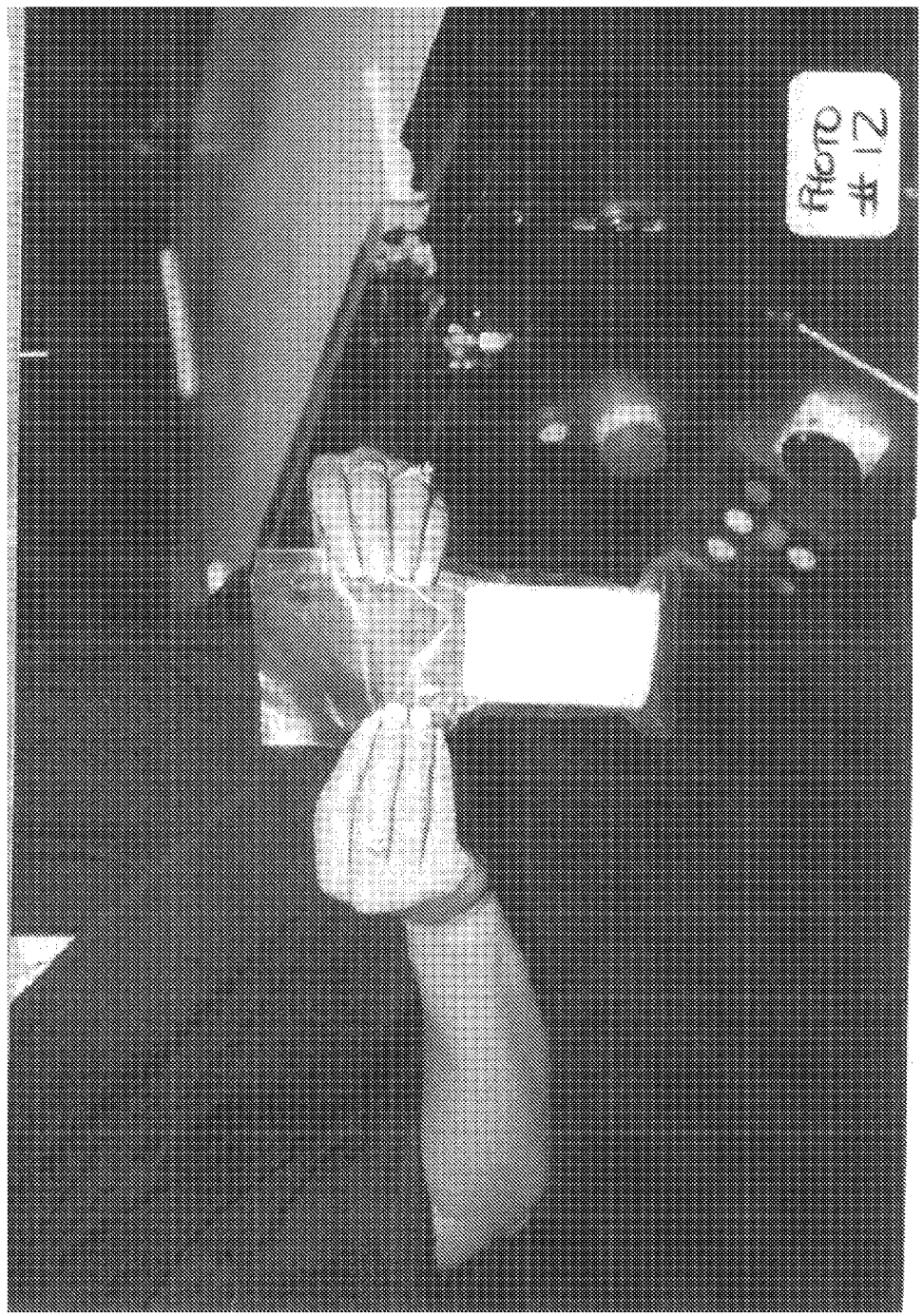
Figure 126:
Figure 127:
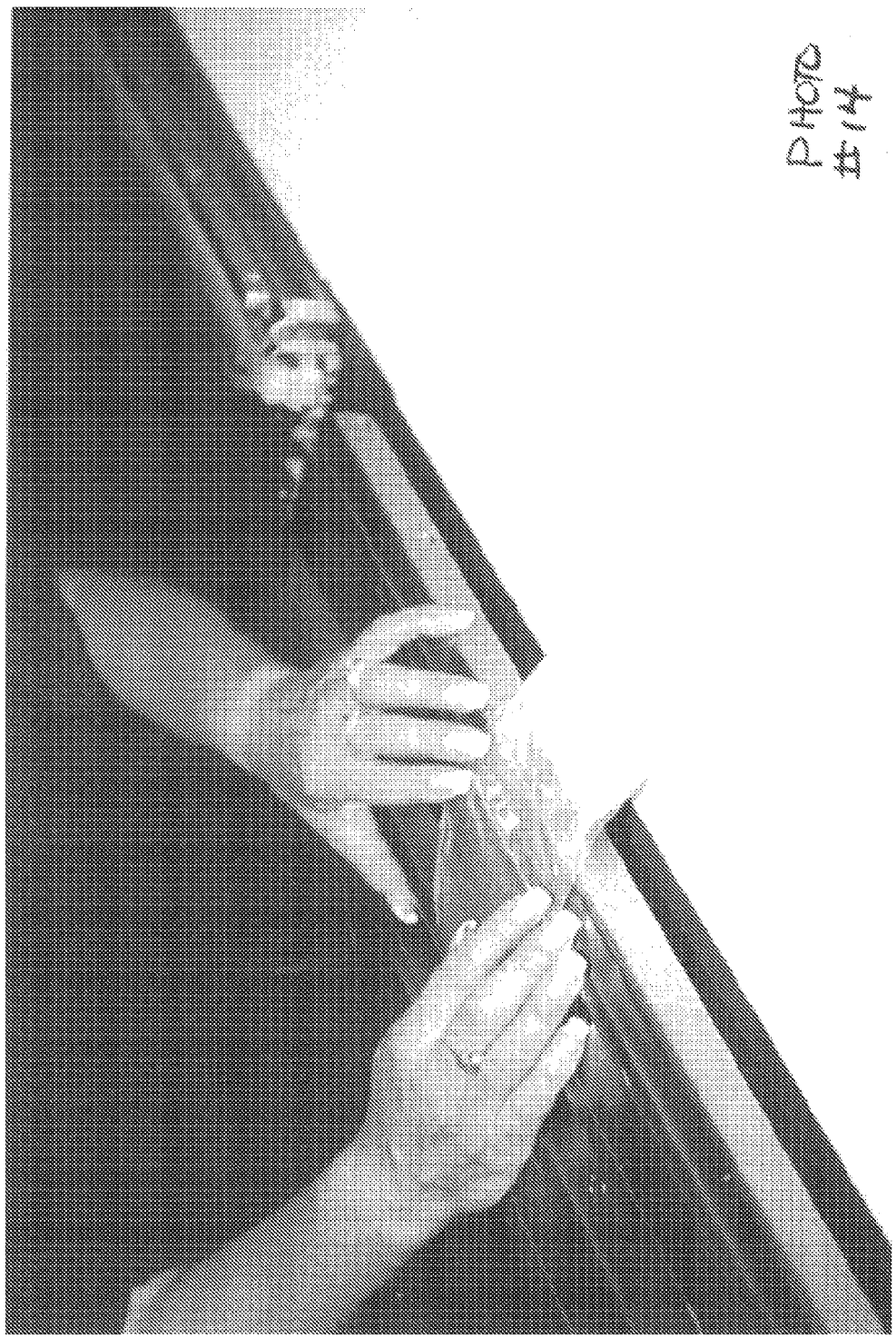
Figure 128:
Figure 129:
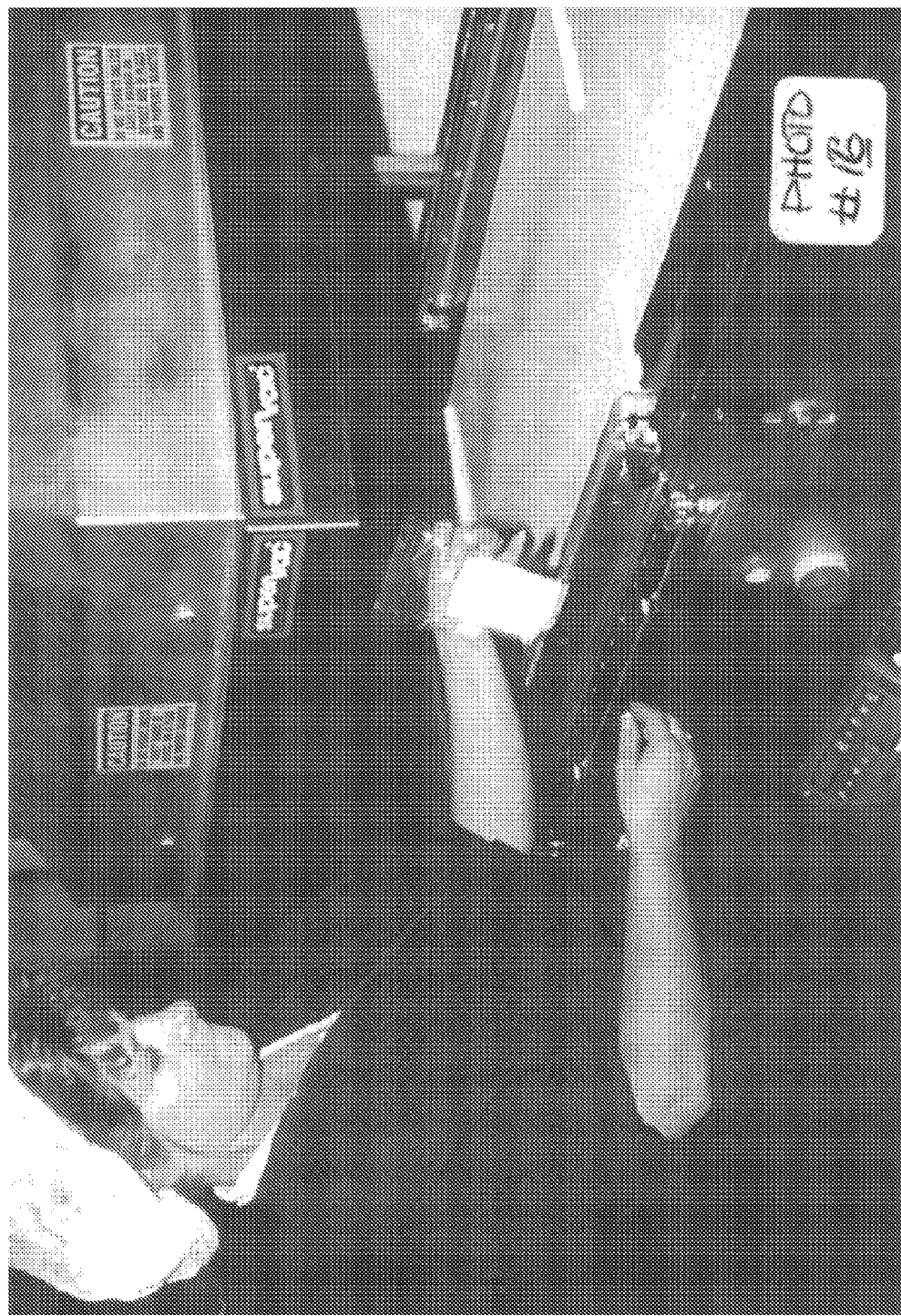

FIG. 79 is an illustration of a COMBO PACK having a first package that includes a number of non vacuum-packed diapers and two diapers that have been vacuum-packed together and that are contained within the same transparent encasement;

FIG. 80 illustrates three examples of vacuum-packed diapers that may be combined with non-vacuum packed diapers of the first packaged, including a "C" folded vacuum-packed diaper, a "twin" pack of "C" folded vacuum-packed diapers, and a flat vacuum-packed diaper;

FIG. 81 is an illustration of a COMBO PACK that includes a vacuum-packed diaper within a second package, wherein the second package is disposed within a first package that itself contains a number of non vacuum-packed diapers;

FIG. 82 is an illustration of a COMBO PACK that includes a first package of non vacuum-packed diapers and a vacuum-packed diaper removably attached to the first package;

FIG. 83 is another view of the COMBO PACK of FIG. 82 illustrating, in part, the elephant cartoon character that is prominently printed on the diaper through the transparent encasement containing the vacuum-packed diaper;

FIG. 84 is an illustration of a COMBO PACK that includes a vacuum-packed diaper and a number of non vacuum-packed diapers;

FIG. 85 is an illustration of an embodiment of a COMBO PACK that includes within a first package not only the non vacuum-packed diapers, but also a "6-Pack" dispenser which, itself, contains six kits each having, inter alia, an individually vacuum-packed diaper;

FIG. 86 is a photographic image of the "6-Pack" dispenser removed from the first package of FIG. 85;

FIG. 87 is a photographic image of a kit (in this embodiment, the container of the kit comprises a box) that is partially removed from the dispenser of FIG. 86;

FIG. 88 is an illustration of three boxes, each of which is used as a container for a kit, with each kit including therein at least a vacuum-packed diaper and wherein each box is removable from the 6-Pack dispenser of FIG. 86, which dispenser also is illustrated in FIG. 88;

FIG. 89 is an illustration of still yet another embodiment of a COMBO PACK that includes of a first package containing the non vacuum-packed diapers and a kit containing, inter alia, a vacuum-packed diaper;

FIG. 90 is an illustration of the kit of FIG. 89 removed from the first package;

FIG. 91 is another view of the kit of FIG. 89 removed from the first package, which view illustrates a panel of the box which hinges;

FIG. 92 is still yet another illustration of the kit of FIG. 89 removed from the first packaged, the image comprising a close-up of the side of the kit shown in FIG. 90 to illustrate a resealable label that permits access to one or more contents of the kit;

FIG. 93 is an illustration of two additional kits that may be used;

FIG. 94 is an illustration of the other side of one of the kits (the larger box) of FIG. 93;

FIG. 95 is an illustration of the other side of the other kit (the smaller box) of FIG. 93;

FIG. 96 is an illustration of still yet another kit that may be used, wherein the container of this illustrated kit comprises a bag made from one or more flexible sheets or films;

FIG. 97 is another view of the kit of FIG. 96;

FIG. 98 is another view of the kit of FIG. 96;

FIG. 99 is another view of the kit of FIG. 96;

FIG. 100 is another view of the kit of FIG. 96 together with a ruler illustrating the length of the kit to be approximately five (5) inches;

FIG. 101 is another view of the kit of FIG. 96 together with a rule illustrating the thickness of the kit to be approximately two (2) inches;

FIG. 102 is an illustration of a preferred arrangement of two 6-Pack dispensers and non-vacuum-packed diapers sandwiched therebetween for disposition in a package to form a COMBO PACK;

FIG. 103 is an illustration of various package form factors that can contain a vacuum-packed diaper for inclusion in a package of diapers;

FIG. 104 is a view of a bulky diaper in the hands of a person;

FIG. 105 is a sketch of a diaper within a jig made for holding and folding said diaper, with a person folding the rough edges inwardly;

FIG. 106 is a view of a diaper with one end being folded inward;

FIG. 107 is a view of a diaper with the other end being folded inward over the first fold;

FIG. 108 shows a hand clamp gripping a folded diaper;

FIG. 109 shows a hand clamp held by a person compressing a folded diaper being inserted into a plastic bag;

FIG. 110 is a perspective view of a folding jig facilitating the hand clamp for inserting a diaper into a plastic bag;

FIG. 111 a folded and compressed diaper within a small plastic bag;

FIG. 112 a folded and compressed diaper within a small plastic bag being positioned within a vacuum sealing machine;

FIG. 113 shows a vacuum sealed diaper within a plastic bag held by a person;

FIG. 114 is an illustration of a bulky diaper in the hands of a person;

FIG. 115 is an illustration of the diaper in a jig made for holding and folding said diaper, with a person folding the rough edges inwardly;

FIG. 116 is an illustration of a first end of the diaper in the jig folded inwardly covering a middle portion of the diaper;

FIG. 117 is an illustration of the other end of the diaper folded in over the first end and middle portion thereby forming a rectangular shape;

FIG. 118 is an illustration of a spring tensioned hand clamp opened with one hand so as to have the upper flat rectangular jaw and lower jaw placed over and under the completely folded diaper;

FIG. 119 is an illustration of the spring tensioned hand clamp and diaper retained therein;

FIG. 120 is an illustration of the spring tensioned hand clamp and diaper retained therein;

FIG. 121 is an illustration of the folded diaper having been compressed being inserted into an open end of an elastic pliable resilient bag using the hand clamp and jig to facilitate insertion;

FIG. 122 is an illustration of the folded diaper having been compressed being inserted into an open end of an elastic pliable resilient bag using the hand clamp and jig to facilitate insertion;

FIG. 123 is an illustration of the folded diaper, compressed by the hand clamp, being directly inserted into the open ended bag by hand;

FIG. 124 is an illustration of the folded diaper, compressed by the hand clamp, being directly inserted into the open ended bag by hand FIG. 125 is an illustration of the folded diaper fully inserted into the bag;

FIG. 126 is an illustration of the folded diaper fully inserted into the bag being placed into a vacuum sealing machine on a deck thereof;

FIG. 127 is an illustration of the folded diaper fully inserted into the bag being placed into a vacuum sealing machine on a deck thereof;

FIG. 128 is an illustration of the folded diaper fully inserted into the bag being placed into a vacuum sealing machine on a deck thereof;

FIG. 129 is an illustration of a "Vac-U-Diaper" product after the vacuum sealing machine vacuum seals and cuts the bag.

V. DETAILED DESCRIPTION

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated therein, which would occur to one skilled in the relevant art and having possession of this disclosure, are to be considered within the scope of the invention.

As illustrated in FIGS. 1A through 2B, an exemplary packaged, disposable, diaper 10 is sized and shaped to consume a considerably smaller volume and be more conveniently shaped than conventional disposable diapers. As illustrated, the packaged diaper 10 begins as a diaper 12 nominally sized and shaped in accordance with conventional diapers. The diaper can be one of a variety of types known to those in the art, and can be formed of a variety of materials. The diaper can be disposable or non-disposable (i.e., reusable).

Figure 1A:
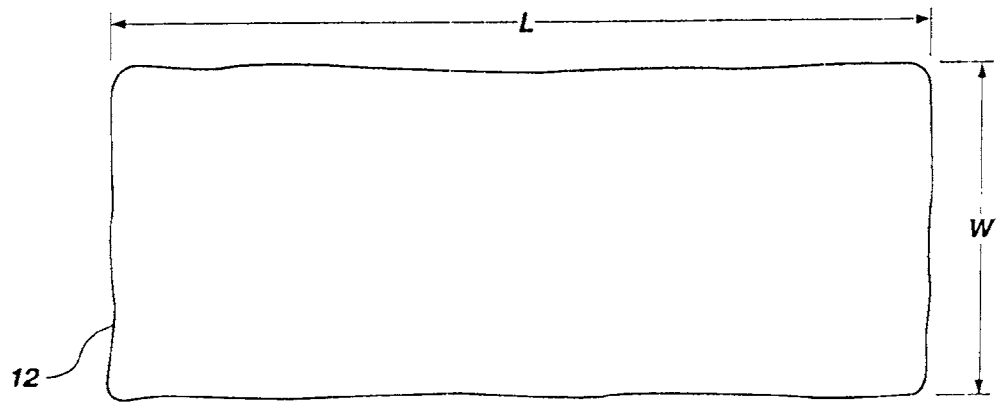
FIG. 1A is a top view of a diaper in a nominal configuration.
Figure 1B:
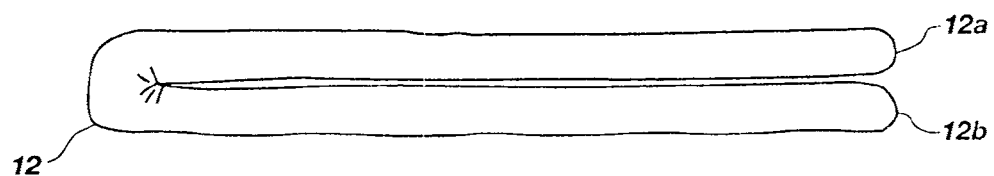
FIG. 1B is a side view of the diaper of FIG. 1A.

As shown in FIG. 1A, the diaper begins with a first, nominal volumetric configuration characterized by a nominal length L and nominal width W of the diaper. As used herein, the term "nominal" is understood to mean to be the normal, post manufacturing state in which it is ready to be unfolded and worn, in reference to the various dimensions of the diaper. Thus, the diaper 12 can have a first size having a height, width and length of nominal size, such as conventionally provided to consumers. While not so required, the diaper 12 can include upper 12a and lower 12b portions, which can correspond to a front and back of the diaper. Many conventional diapers are provided with a front and back portion of different configuration.

Figure 2A:
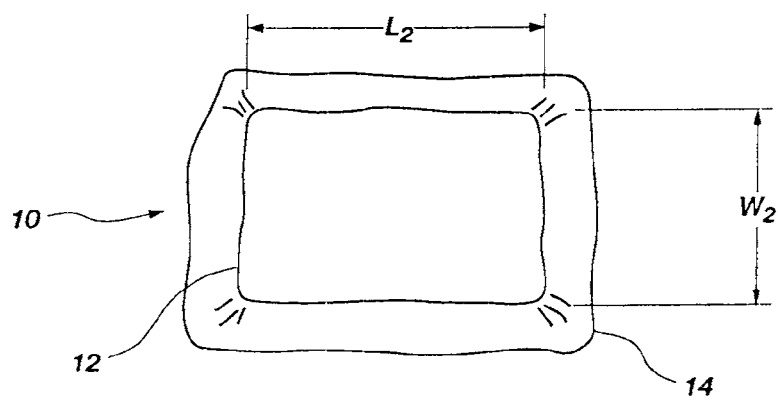
FIG. 2A is a top view of a diaper in a volumetrically reduced configuration.
Figure 2B:
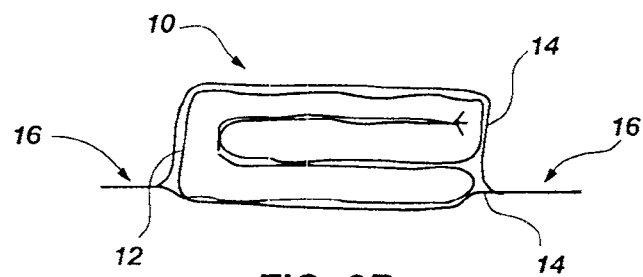
FIG. 2B is a side view of the diaper of FIG. 2A.

As shown in FIGS. 2A and 2B, an example of a packaged diaper 10, after being prepared in accordance with the description to follow below, includes a diaper 12 having a second, reduced volumetric configuration characterized by a reduced length $L_2$ and width $W_2$ of the diaper 12. The reduced volumetric configuration can differ from the nominal volumetric configuration in width, height, thickness, volume and overall size. As will be appreciated from the figures, not only is the volume of the packaged diaper reduced overall, but in the example embodiment at least two of the length, width and height can also be reduced. Thus, the diaper can be reduced in volumetric configuration to consume much less space than the diaper consumes when in the nominal configuration.

As mentioned, the diaper 12 can be disposed in an encasement 14, which can be formed of a substantially air impermeable material. By disposing the diaper in the encasement in the second, reduced volumetric configuration, a packaged diaper is provided that consumes much less space than the when in its nominal configuration. By "substantially air impermeable," what is meant is that the permeability is low enough that the product has a reasonable shelf life without significant expansion.

As an example, it has been found that by drawing a vacuum down to about 5 Mbar at room temperature and pressure at a location about 5,000 feet elevation above mean sea level, the volume of the diaper can be reduced to as little as ⅓ or ¼ that of the nominal volume. Similar results are to be expected at locations of different elevation. However, as is known, at lower elevations a greater vacuum can be drawn to allow for subsequent transportation of the packaged product to higher elevations. For example, vacuum packaging using a vacuum down to 1 or 2 Mbar is common at lower elevations. Thus, in the space required to store one conventional diaper, three, four, or more, diapers packaged can be stored. The reduced volume packaged diapers are not only advantageous in reducing storage space, the space required for packaging, shipping, etc., is also reduced, leading to considerable cost savings in associated processes.

While the reduced volume configuration can be created and maintained in a number of ways, in the embodiment shown in FIGS. 2A and 2B, the packaged diaper 10 includes encasement 14, which can encompass the reduced volume diaper. Once the diaper 12 is disposed within the encasement, the encasement can be at least partially evacuated of air so as to contain the diaper in at least a partial vacuum state. The evacuation of air from within the diaper and encasement can be done in a number of ways, such as by conventional vacuum-packing methods.

For example, according to at least one conventional vacuum-packing method known to those skilled in the relevant art, an article to be vacuum-packed is inserted into an unsealed encasement formed of a substantially air impermeable flexible material. The unsealed encasement with the article therein is then placed onto the deck of a vacuum-sealing machine. The lid of the machine is then lowered establishing a seal with the deck and to define a chamber between the deck and the lid with the unsealed encased article within the chamber. A pumping system then evacuates ambient air from the chamber creating at least a partial vacuum state within the chamber and within the interior space of the unsealed encasement with the article therein. Sealing bars then seal the encasement to maintain at least a partial vacuum state therein. Ambient air pressure is then restored to the chamber effecting a pressure differential across the sealed encasement. Insofar as the article within the sealed flexible encasement is compressible, the pressure differential acts upon the encasement to compress the article and maintains the article in a reduced volume that is less than the volume of the article at the time the encasement was sealed (before ambient air pressure was restored to the chamber). The lid of the machine is then raised and the vacuum-packed article is available for removal from the machine.

Upon evacuation of air from the encasement, the encasement can be sealed, for example at an edge portion 16 to maintain the vacuum within the encasement and diaper 12. In this manner a differential pressure can be created within and without the encasement to maintain the second, reduced volumetric configuration of the diaper. While the encasement is shown in FIG. 2B as sealed at an edge portion 16, it will be understood that the encasement can be sealed conventionally in a variety of ways in a variety of locations.

As the encasement 14 configured to confine the diaper 12 is unsealed, the diaper is able to return to its nominal volumetric configuration. That is, user can cut, tear, remove a portion of the encasement, or otherwise break the airtight seal of the encasement; after which, the diaper 12 will no longer be subject to confining force due to the encasement and/or a pressure differential. Unopposed rebound forces in the materials from which the diaper is made will tend to return it to its nominal configuration. The encasement can include a means to facilitate opening, such as a notch or another intentionally formed discontinuity (not shown) provided in the encasement to aid in opening the encasement. In one embodiment a tear-away band, or the like, provided with a grasping tab (not shown) can be provided to facilitate opening by rupturing the encasement as it is pulled away therefrom. One of many other well known ways to provide a more easily broken-open encasement can be used to facilitate opening the packaging.

As described in further detail below, the reduced volumetric configuration can be achieved in a number of ways, and in the embodiment shown in FIGS. 2A and 2B, the volumetrically reduced configuration is created by foldingly reducing a length and width of the diaper 12; increasing its thickness. The folded diaper is then vacuum-packed to reduce its thickness (as well as its width and length to a lesser extent). As used herein, the term "foldedly reduced" is meant to indicate the case wherein a diaper is folded or rolled over or under itself to thereby reduce a dimension of the diaper. While the final size of the reduced volume diaper can vary, in one embodiment the reduced length and width can each be less than about ½ of the nominal length and width, respectively, of the diaper. In another embodiment, the foldedly reduced length of the diaper can be less than about ⅓ and/or ¼ of the nominal length of the diaper. In this manner, as shown by comparing FIGS. 1A and 1B with FIGS. 2A and 2B, the overall width and length of the diaper can be substantially reduced. While a height dimension, corresponding to thickness, may be increased, it is not increased to exceed the width or the length of the diaper. This results in a more convenient and compact size overall.

The inventor has found that a conventional size 6 diaper can be reduced in size and volume from a nominal size of approximately 9" long by 4.5" wide by ¼" to 1" in height/thickness (depending on expansion after removal from conventional packaging) to a reduced size of approximately 3.5" long by 2.25" wide by 1" in height. In the embodiment shown in FIGS. 2A and 2B, the packaged diaper 10 can include a reduced volumetric shape configuration which comprises a substantially rectangular shape, although other shapes are contemplated as well, as discussed in further detail below. In this manner, the packaged diaper can be easily carried, handled and stored within a purse, pocket, bag or other place or containment for carriage.

The packaged diaper in a densified state can thus be made pocket sized, or pocketable. As used herein that means that it is conveniently sized for carriage, for example about the size of a conventional cigarette package or smaller. One way to characterize this is that two of the three dimensions of height width and length, when added together, are less than 10 cm, and the greatest of the three does not exceed 10 centimeters. That said, all pocket sized items may not strictly fit this definition, but it is a definite guide in understanding what is meant by the term as used herein.

It will be appreciated that in this example a compact, efficiently sized packaged diaper is provided that requires substantially less space than conventionally packaged diapers. The packaged diaper can be advantageously utilized by a variety of persons, including incontinent minors and adults, and caretakers of individuals requiring diapers.

For example, parents of young children will benefit in that one or more diapers 10 can be easily stored in a pocket, or within a purse, briefcase, backpack or other storage bag and consume relatively little space. Similar benefits can be obtained with regard to incontinent adults, as adult diapers are generally even more bulky and difficult to store and carry than are smaller, children's diapers. Also, incontinent adults who may be otherwise embarrassed by having to carry spare clean diapers will likely find the packaged diapers to be much more discreetly transportable, and therefore the carriage of such spare diapers much less noticeable by others.

Additionally, in one aspect pocketable diaper is provided and can include an encasement configured to encase and confine a diaper disposed therein. A diaper can be disposed within the encasement to be confined by the encasement in a size that is volumetrically reduced relative to a nominal size of the diaper. The volumetrically reduced size of the diaper is characterized in that the diaper is pocketable upon a person of an individual. As used herein, the term "pocketable" is to be understood to indicate a configuration of the diaper in which the diaper can be easily placed within and removed from a pocket of an item of clothing or accessories worn or carried by individuals. For example, the pocketable diaper can be held within a shirt, jacket or pants pocket or stored or carried in a handbag, purse or briefcase, etc., and can be substantially undetectable by other individuals. In this manner, an incontinent adult can carry the pocketable diaper without worrying that others will be aware that the diaper is being carried. Also, an adult caretaker of an infant can carry a diaper for the infant in a manner that does not detract from a physical appearance of the adult and does not require additional baggage.

In several embodiments, a reduced diaper is provided. The reduced diaper is densified by volumetric reduction from a first greater volume and lesser nominal density to a second reduced volume and increased density. An encasement can also be included and the diaper can be disposed in the encasement in the second reduced volume. The encasement can thereby confine the reduced diaper so that the diaper is retained in the reduced volume by the encasement. The volumetric reduction can entail dimensional reductions in width, thickness, length, and diameter. In this manner, a volumetrically reduced, space-efficient densified diaper is provided that can be easily stored and carried by an individual in a discreet manner. Upon release of the reduced diaper from the encasement, the diaper can be volumetrically expanded and used in the same manner as conventionally packaged diapers.

As used herein, the term "encasement" is to be understood to encompass a broad range of materials and configurations for containing or restraining or enclosing a volumetrically reduced diaper. For example, the encasement may completely encompass a diaper and hold the diaper under a vacuum seal or other pressure differential. In addition, the encasement may only partially encompass the diaper to maintain the compressed state of the diaper. Moreover, it is intended to be understood herein to be synonymous with restraint (as discussed below) or enclosure, or containment, in this context. The salient point being that it constrains, by some means, the densified diaper from expanding. Other encasements besides the examples shown can also be utilized, as would occur to one skilled in the art.

Figure 3D:
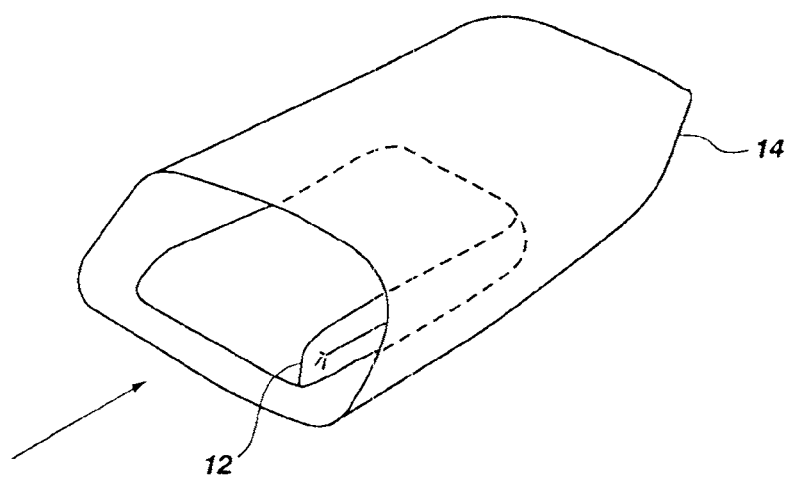
FIG. 3D is a perspective view of the diaper of FIG. 3C being disposed within an encasement.
Figure 3E:
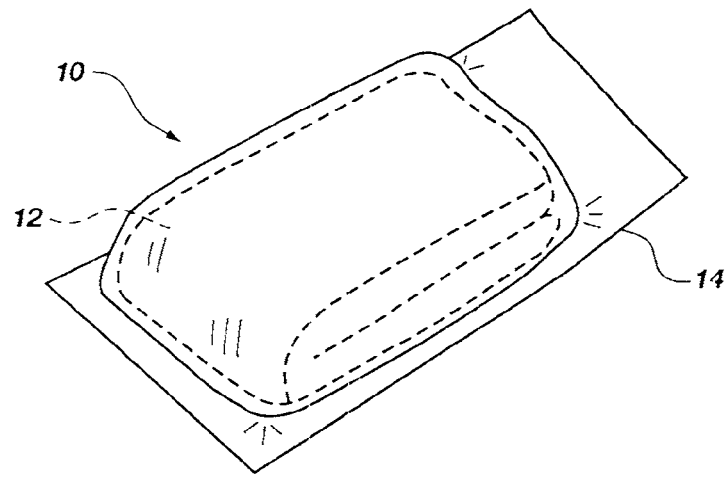
FIG. 3E is a perspective view of the diaper of FIG. 3D held under vacuum within the encasement of FIG. 3D.

Shown in series in FIGS. 3A through 3E is an aspect in which a diaper is reduced from its nominal volume or size to a reduced volume or size. Diaper 12 begins with a nominal volumetric configuration, sized and shaped as may be conventionally provided by a manufacturer of the diaper. In this embodiment, the diaper is reduced in volume by fold 17 along a lengthwise aspect of the diaper, shown at line 18. In FIG. 3C, the diaper 12 is folded at 19 along a crosswise aspect of the diaper, shown at line 20. Progressing to FIG. 3D, once the diaper has been folded a desired number of times; the folded diaper is disposed within encasement 14, which is formed of a substantially air impermeable material. Encasement 14 can then be evacuated to form a relative vacuum within the encasement, after which the encasement can be sealed to maintain the vacuum in the diaper and the encasement.

It will be understood by those skilled in the art that the process of forming a vacuum within the diaper and the encasement will extract at least a portion of air contained within the diaper. By removing a majority of excess air from the diaper, the diaper can be compressed upon itself by atmospheric pressure and consume a reduced amount of space corresponding to the amount and volume of air removed from the diaper.

In addition to the process illustrated in FIGS. 3A through 3E, in another aspect, a method of packaging a diaper is provided and includes the steps of volumetrically reducing a size of the diaper to a size convenient for carriage and storage of the diaper. The volumetrically reduced diaper can then be disposed within an encasement. The volumetrically reduced, convenient size of the diaper can be maintained by a pressure differential acting upon the encasement. As used herein, the term "convenient size" is understood to refer to a size and configuration of a diaper that can be easily and conveniently stored in a pocket, handbag, purse, etc., and consume very little space within the pocket, handbag, etc. Such a size will be appreciated to be essentially a "pelletized" or "capsulated" or "pocket sized" or "pocketable" (as defined above) version of the diaper, having bulk due to air spaces removed, and will be generally cylindrical, rectangular, etc, and can have rounded or square corners. Generally, the largest dimension will be about four inches or less. However, for certain specialized applications such as kits contained in a feeding bottle, a longer, more "sticklike" shape may be used in one embodiment. But likewise a cylindrical or square configuration having height, width, and length dimensions of roughly equal magnitude can also be advantageous in such a kit in another embodiment. The salient point is that the size is convenient to carry and conceal.

The size of the diaper can be volumetrically reduced in a number of manners, including pressing the diaper into a mold or other cavity. In this example, the encasement in which the diaper is disposed can be sized and shaped to correspond closely to the volumetrically reduced size of the diaper. Once disposed within the encasement, the force applied to compress the diaper into the mold can be released, after which the diaper will tend to return to its nominal size and shape, but will be restrained by the encasement. The pressure differential acting upon the easement will thus be the result of the diaper tending to expand into its nominal configuration. An equilibrium will be reached between a) the restoring force tending to expand the diaper; and b) a combination of the hoop strength (resistance to expansion of the encasement via deformation of the encasement) and the pressure differential tending to compress the diaper. Depending on the material from which the encasement is made, this can be made to be predominantly hoop strength or predominantly air pressure differential.

Figure 4:
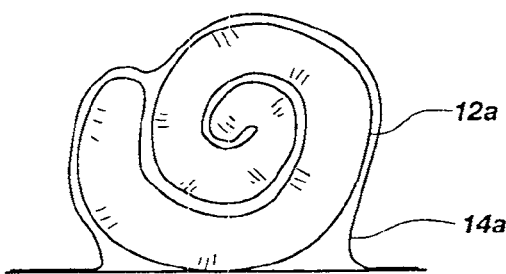
FIG. 4 is an end view of a packaged diaper having a reduced volume in a substantially cylindrical shape.

While the example packaged diaper shown in many of the figures of this disclosure includes a generally rectangular shape, it is contemplated that the volumetrically reduced diaper can be of a variety of sizes and shapes. For instance, as shown in FIG. 4, volumetrically reduced diaper 12a can have a substantially cylindrical shape. This embodiment may be beneficial, for example, in applications in which the diaper is to be stored in rounded or cylindrical receptacles, such as cans or tubes. As will be appreciated, by forming encasement 14a from a flexible, substantially air impermeable material, a vacuum formed within the encasement will force the encasement to conform to the general shape of the reduced volume diaper. In this manner, the diaper can be formed in a variety of reduced volume shapes for a variety of applications.

In another example embodiment the encasement shape can control the shape of the packaged diaper. For example, a diaper can be compressed into an encasement within a mold cavity which encasement has a shape which essentially follows the shape of the mold. Thereafter the encasement maintains that shape, though the diaper may expand slightly against the hoop strength, air pressure differential, or combination thereof.

Figure 5:
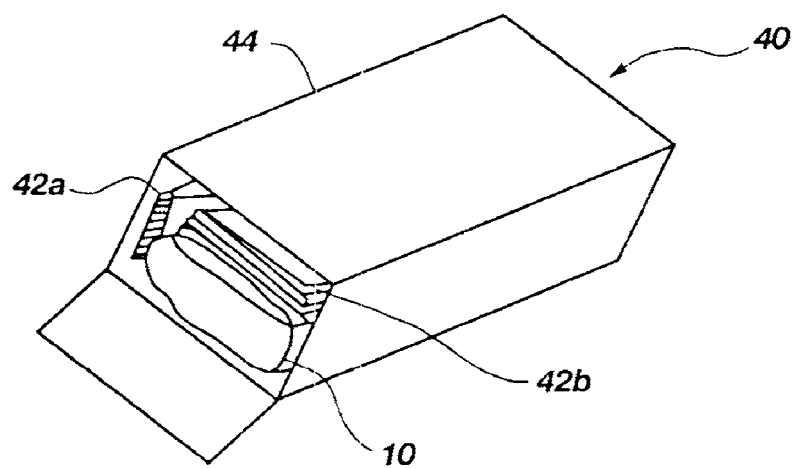
FIG. 5 is a perspective view of a diaper kit.

As illustrated in FIG. 5, in another aspect a diaper kit 40 is provided. The kit can include a packaged diaper 10 in accordance with the embodiments discussed above and at least one diaper accessory 42. A container 44 is also provided, in which each of the packaged diaper and the diaper accessory are disposed. The diaper accessory can be a variety of items, including, but not limited to, a diaper rash ointment or other medicament, talcum powder/baby powder, a lotion, moist or dry wipes, cotton swabs, dirty diaper disposal bag, etc., as may be needed in caring for an infant or incontinent person, as will be known to one skilled in the art of providing products for care of such persons. In the example embodiment shown, a packet of ointment 42A is included in the kit, as are moist wipes 42B.

Thus, in one example, substantially all of the materials necessary for changing a soiled diaper are provided in a small, space optimized kit that can be easily carried or stored by a caretaker of an individual requiring diapers. The kit can be advantageously used as a daily staple of caretakers, or may be used in specialized circumstances such as outdoor activities, travel, or business or recreational events away from home, or other situations in which space and convenience of carriage may be of a premium. In such circumstances the caretaker may wish to minimize the number of articles needing carriage, and can advantageously carry one or two kits, as may be needed, and dispense with the conventional diaper bag that would otherwise have to be carried during the event or activity. Also, the reduced size of the present diaper kit can allow one or more kits to be stored in an out-of-the-way location, such as a glove box of a car, and retrieved in "emergency" situations in which spare diapers were forgotten or consumed.

In another embodiment, the kit can be configured for use by an incontinent adolescent or adult. The kit can further include supplies to touchup stains on clothing. It can contain a small container of perfume or cologne, a small container of odor reducing spray, or other items which an incontinent adult may find needful and reassuring to carry, in addition to supplies which customarily may be needed to change a diaper, including a clean diaper, wipes, and lotion, ointment or other medicament, to name some examples.

Figure 6A:
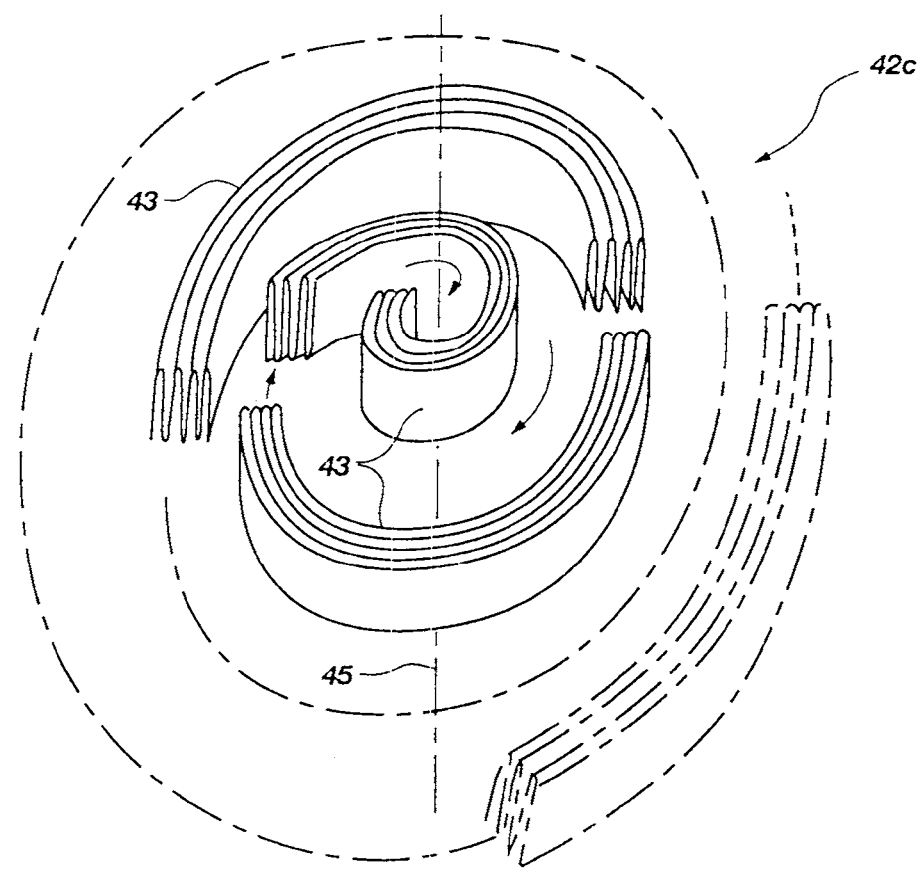
FIG. 6A is a perspective view of a diaper wipe configuration usable with the kit of FIG. 6 in one example.

As shown in FIG. 5, the diaper kit 40 can include a container 44 that is substantially rectangular in shape. Such kits can be easily stacked and stored and will fit neatly into a pocket, purse or other baggage. In another embodiment, as shown in FIG. 6, the container 46 can be substantially cylindrical in shape. In this embodiment, the diaper 12b can be formed in a cylindrical shape, or other shape to facilitate maximum use of available space within the cylindrical container. Also included in the illustrated example shown in FIG. 6 are moist wipes 42C which can be arranged in a disk-like or toroidal configuration for disposal within the cylindrical container. With reference to FIG. 6A, the individual wipes 43 are accordion folded, then rolled about an axis 45 transverse to the folds. A surprisingly large number of wipes thus configured can be fit into a surprisingly small space. In this manner, 6 or 7 wipes or another selected number of wipes can be stored within the container 46 to ensure ample supply.

Figure 7:
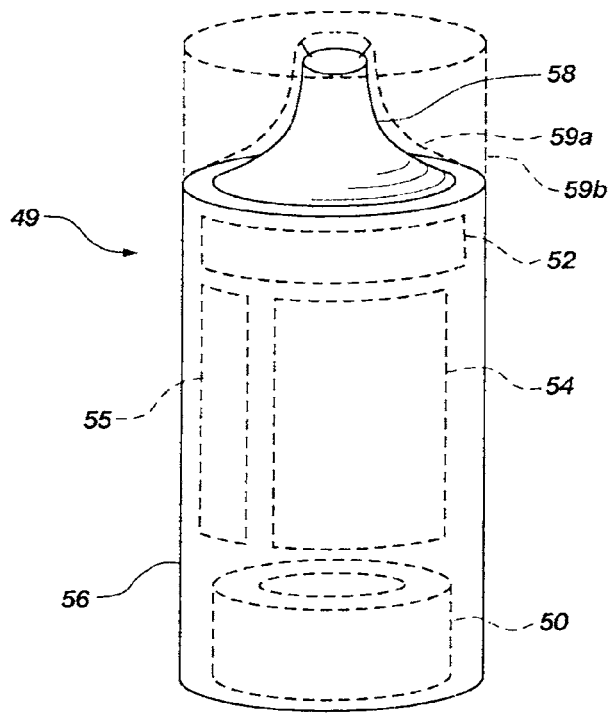
FIG. 7 is a perspective view of an infant care kit.

In another aspect, illustrated by example in FIG. 7, an infant care kit 49 can be provided which includes a diaper 50, one or more diaper accessories 52 and a portion of infant food 54. An infant feeding bottle assembly is also provided having a hollow body 56 and a nipple food delivery portion 58 of the device couplable thereto. A cover 59a or 59b can be provided, which keeps the feeder portion sanitary. This can be a throw-away tear-off film cover (e.g. 59b) or a more conventional replaceable cap (e.g. 59a). The feeding apparatus can be single use (i.e., disposable) or reusable. As shown, the diaper, diaper accessory, and portion of infant food can be disposed within the infant feeding assembly for convenient carriage. The infant feeding assembly can thus be configured to: i) contain each of the diaper, diaper accessory and portion of infant food; and ii) upon removal of the diaper and diaper accessory, receive the portion of infant food (and water, if applicable) within the hollow body and thereby enable delivery of the infant food to an infant via a food delivery device erstwhile acting as a container for the kit. In one embodiment the nipple portion can be configured for delivery of baby formula, and in another embodiment it can be configured for delivery of a flowable baby food such as a formula/cereal mixture, creamed vegetables or fruit, or the like. In one embodiment the baby food can be in powder form, reconstituted by addition of water. A chemical warming pack (similar to or the same as a conventional hand warming pack) can be provided for use in warming the baby formula or other baby food.

In this example implementation, substantially all of the materials necessary to feed and change a diaper of an infant are provided in a compact, easily carried kit. A caretaker of the infant can use the kit to store the provided items, and when desiring to feed the infant, can prepare the portion of infant food and feed the infant with the infant feeding assembly, shown in this embodiment as similar to a conventional baby bottle, but provided with a detachable bottom.

As shown in the illustrated example, the hollow body 56 of the feeding assembly 49 can be substantially cylindrical in shape, although other shapes are also contemplated, such as squared, triangular, and other polyhedral cross-sectional shapes. The portion of infant food can include a variety of foods suitable for consumption by infants, including powdered baby formula and condensed baby formula, freeze dried, powdered, concentrated creamed vegetables and fruits and other baby foods, as well as cereal mixes, etc. A caretaker can easily remove all items from the feeding assembly, configure it for feeding, and returning the portion of infant food (with water, as mentioned, if necessary, or other fluid which can be added to the infant food) and the food can be fed to the infant via a food delivery device 58, a conventional baby bottle nipple in the illustrated embodiment.

In one embodiment, the feeding apparatus can include a double wall configuration to provide increased insulation so as to keep formula or other baby food at a desired temperature for a longer period of time. To facilitate this, or, to provide initial warming when hot potable water is unavailable, a heat source 55, as mentioned, can also be disposed within the feeding assembly. The heat source can be configured to provide heat for warming the portion of infant food, as well as any fluid having been added to the infant food. In situations where it may be necessary to add cold fluid such as milk or water to the infant food, the fluid and food can be warmed to a temperature well tolerated and more acceptable to an infant. As mentioned, the heat source can be a conventional chemical heating apparatus, such as those producing an exothermic reaction when two or more separate materials are mixed, or are exposed to air. These can be packets of reactants in granular form, chemically activated gel heating sources, etc. The feeding apparatus can be configured to cooperate with the heat source to heat the baby formula or other food. In one embodiment, the kit can include an outer container (not shown) which is the outer wall of the double wall configuration mentioned. This can be a continuous wall, or can comprise vents (e.g. to expose air to air-reactant heating pads). A mesh or other textile can be used as the material forming the outer containment in which the infant feeding assembly is disposed. The outer container can be configured to receive and protect the feeding assembly and can also encompass the heating source to maintain close contact between the heating source and the hollow body 56.

In another embodiment, the heat source can be some other means of providing heat, for example provision of a metal outer sleeve, annular space for water, and inner container for formula or food enabling use of a cigarette lighter, a solar reflector or magnifier, or some other higher temperature heat source to heat the outer sleeve and still enable more gentle warming of the contents of the inner sleeve. Such an arrangement would also facilitate rapid cooling of the outer sleeve after removing the high temperature heat source so that it can be safely handled, enabling removal of the inner sleeve for feeding for example.

Figure 8:
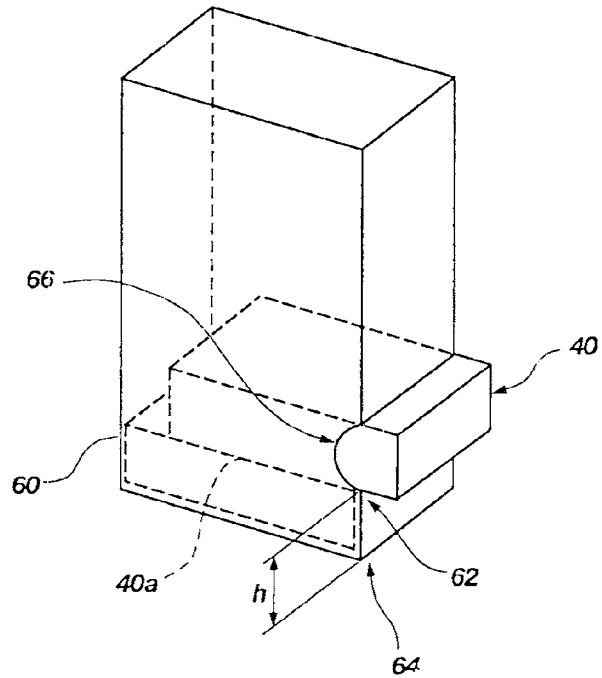
FIG. 8 is a perspective view of a master container.

In another exemplary embodiment, shown in FIG. 8, a plurality of single use packaged diapers (not shown), or diaper kits 40, 40A can be provided packaged together, each stacked vertically in a master container 60. The master container 60 can include a removable access panel (previously removed in FIG. 8) through which one 40 of the plurality of containers can be accessed. Providing for the removable access panel can be in one of a variety of ways known to those in the art, including a perforated removable panel or hinged panel. A bottom 62 of the access panel can be disposed in the master container 60 in a location vertically displaced from a bottom 64 of the master container by a distance substantially equal to a height "h" of the container. It has been found that having the last container to be used positioned below the access panel helps keep the shape of the master container and improves appearance over the dispensing life of the product.

In this manner, as a kit is removed from the master container, the kit immediately above the removed kit will fall into place to be easily removable from the master container. Notches 66 can be provided adjacent the removable panel to enable easy withdrawal of kits through the panel. The master container 60 can be used to package and ship a number of kits 40, and advantageously also used to dispense the kits at a retail center or other point of sale. While the master container shown in FIG. 7 is configured to store and dispense 6 diaper kits, master containers configured to store and dispense fewer or more kits can also be provided, and include two or more access panels disposed and oriented in a variety of locations on the master container.

Figure 9A:
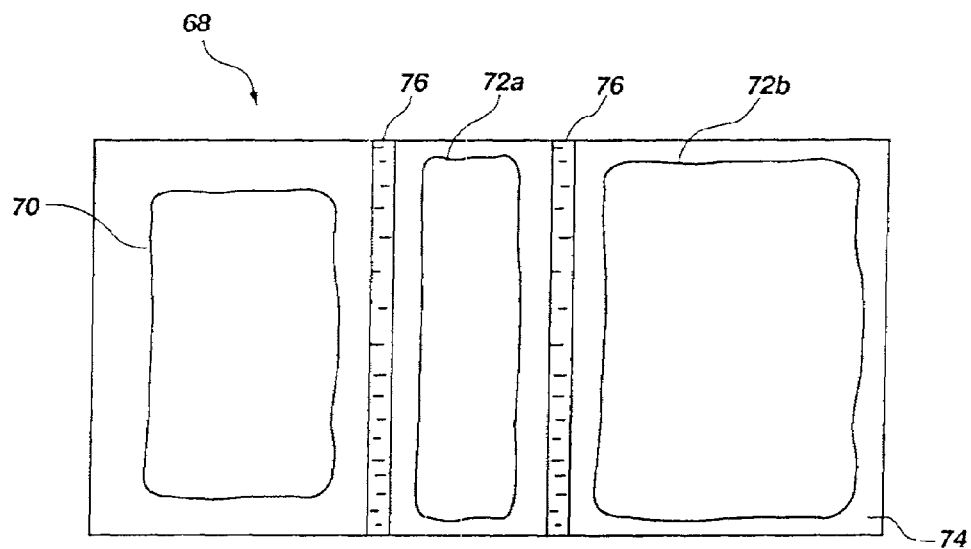
FIG. 9A is a top view of another diaper kit.
Figure 9B:
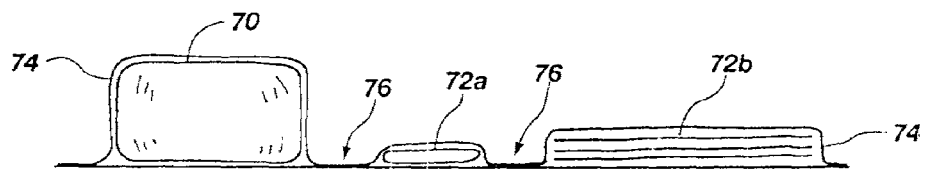
FIG. 9B is a side view of the diaper kit of FIG. 9A.

Illustrated in FIGS. 9A and 9B is a diaper kit 68 in accordance with another example implementation. In this embodiment, a diaper 70 and various diaper accessories 72 are contained within an encasement 74. The accessories can include baby ointment, baby wipes, powder, etc. as discussed above. In this example the accessories include baby ointment 72A and wipes 72B. Other accessories can be substituted or additionally included. Shown at 76 are seams formed in the encasement defining adjacent compartments that can each hold a different product. The seams can separate products to enable differing treatment of the products in relation to the encasement. For instance, diaper 70 can be disposed in the encasement in a reduced volumetric configuration, as discussed above, and the encasement can be evacuated and vacuum-sealed about the diaper. However, the baby ointment 72A can be vacuum sealed (if already packaged in an impermeable containment without excess air) but need not be vacuum sealed (indeed it may be difficult to do so if not already packaged) in its corresponding compartment. Likewise the wipes 72b are not vacuum packed, but could be if previously enclosed in an impermeable containment without excess air.

While it may be desirable to vacuum-pack the diaper 70, and it is possible to do so with some accessories, it may be the case that certain accessories are not well suited to such an arrangement. For instance, with regard to the previously mentioned examples of ointment 72a and wipes 72 not pre-packaged, baby wipes are often saturated or at least moisture-laden with a liquid cleaning compound similar in appearance to soapy water, to aid in the cleaning process associated with changing diapers. When subjected to a vacuum, the moisture may be withdrawn from the wipes, leading to poor performance of the wipes. In addition, if undue moisture is removed during the vacuum process, the moisture may interfere with sealing the encasement once vacuum has been drawn, leading to premature breach of the encasement. The same applies to the ointment, it would be likewise problematic to vacuum pack it, even more so. Thus, for some products a vacuum seal may not be desirable or necessary, and those products can be sealed in the encasement without being placed under vacuum.

To address these issues, the invention in one embodiment advantageously provides a diaper kit that can include differently and variably treated compartments. In the example shown, the compartment containing the diaper 70 can be treated with a vacuum to aid in maintaining the volumetrically reduced configuration of the diaper. The compartment holding the ointment 72A may or may not be vacuum treated, as the situation dictates. The compartment holding the wipes 72B can be simply sealed to retain the moisture in the wipes without drawing any moisture out with a vacuum process. Other compartments (not shown) can be treated according to the product stored in each one.

Figure 9C:
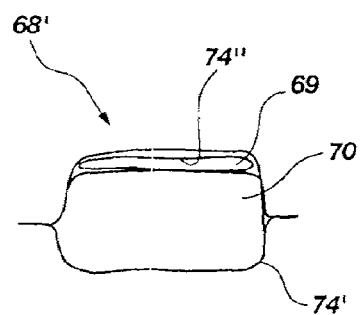
FIG. 9C is a side view of another example diaper kit.

In addition to the compartmentalized encasement shown in FIGS. 9A and 9B, it is contemplated that in another exemplary embodiment of the invention, shown in FIG. 9C, one can provide a diaper kit 68' in which all of the components of the kit are contained in an encasement 74' and sealed under vacuum. For example, the diaper wipes 69 and/or other accessories can be pre-packaged in one or more casings 74" with liquid and wipe material therein. In this way, both a diaper and one or more accessories, together forming a single use kit, can be integrally packaged in one encasement 71', and can all be accessed once the encasement has been breached.

Figure 10A:
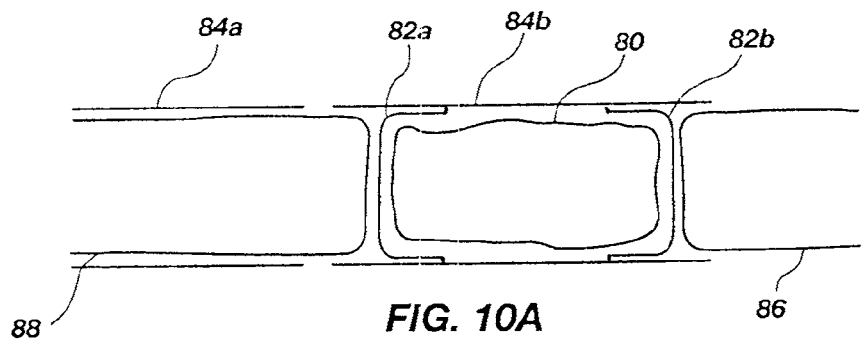
FIG. 10A is a schematic view of one step of a process of packaging a diaper.
Figure 10B:
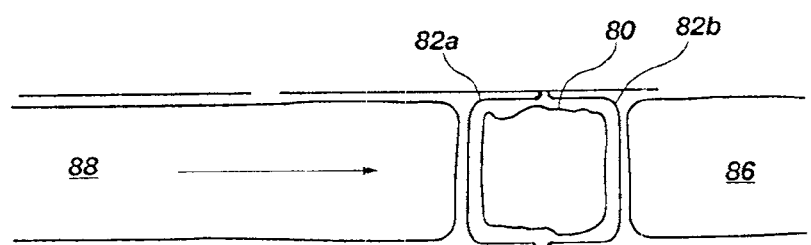
FIG. 10B is a schematic view of another step of the process of FIG. 10A.
Figure 10C:
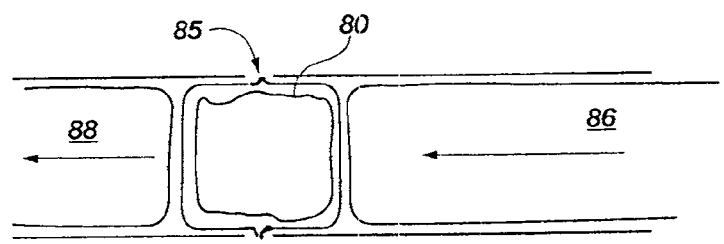
FIG. 10C is a schematic view of another step of the process of FIG. 10A.
Figure 10D:
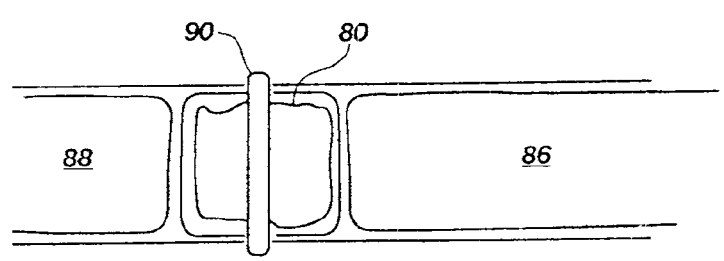
FIG. 10D is a schematic view of another step of the process of FIG. 10A.

With reference to FIGS. 10A through 10E, in one embodiment of the invention the encasement in which the volumetrically reduced diaper is disposed can contain the diaper without any substantial pressure differential acting upon the encasement. One illustrative process in which this can be achieved is illustrated in FIGS. 10A through 10E. In this embodiment, a "loose" diaper 80 is placed within a chamber 84B with a pair of encasement shells 82 disposed adjacent ends of the diaper. Rams 86 and 88 can be activated to compress the diaper into a volumetrically reduced configuration, as illustrated in FIG. 10B. Once optimal reduced volume is achieved, the diaper/shell assembly can be moved adjacent a channel 85 defined between the chambers 84A and 84B, as illustrated in FIG. 10C.

Figure 10E:
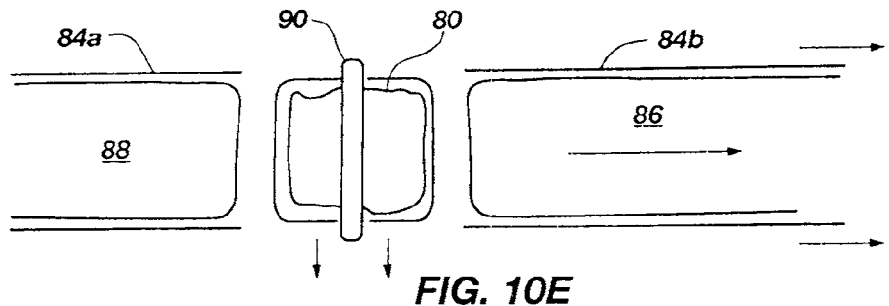
FIG. 10E is a schematic view of another step of the process of FIG. 10A.

Channel 85 can provide access to the diaper/shell assembly to enable attachment of a clamping strap 90 to the shells 82. The strap can aid in maintaining relative position of the shells 82 after the pressure applied to reduce the volume of the diaper is released. Thus, as shown in FIG. 10E, the rams 86, 88 and chambers 84 can be removed from contact with the diaper, and the encasement maintains the diaper/shell assembly in the volumetrically reduced configuration. In this manner, it is not necessary to apply a vacuum to the encasement to create and maintain the volumetrically reduced size of the diaper. In another embodiment, the encasement can be made air tight by application of the clamping strap, and thus a combination of differential pressure and hoop strength of the encasement can contain the diaper after the encasement expands to an equilibrium state.

Figure 11A:
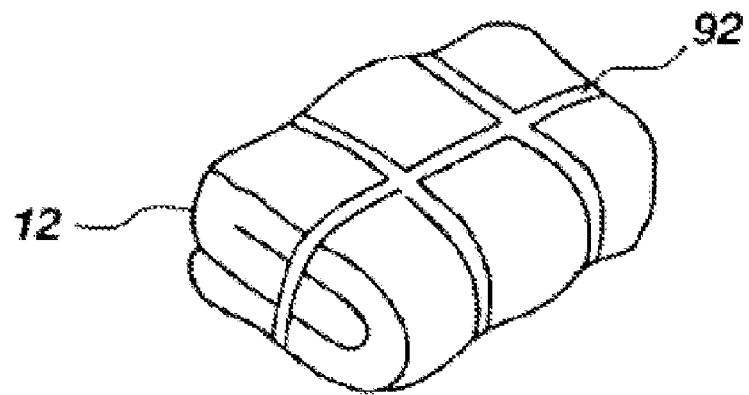
FIG. 11A is a perspective view of a diaper held by a restraint.
Figure 11B:
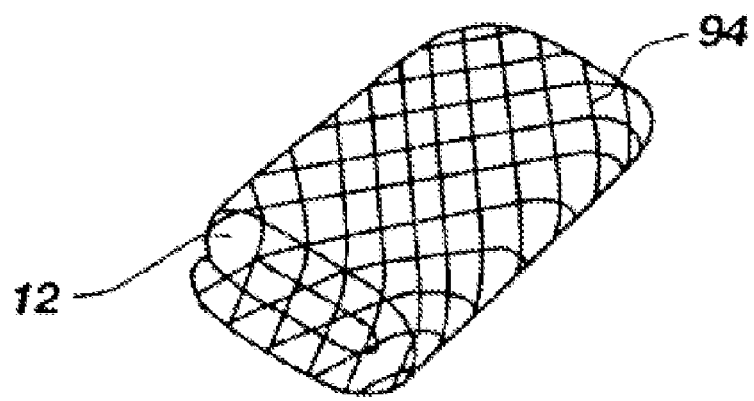
FIG. 11B is a perspective view of a diaper held by another restraint.

As shown in FIGS. 11A and 11B, in one aspect of the invention, a restraint 92 can be provided in which the diaper 12 can be disposed a second, reduced size, relative to a first, nominal size. The restraint 92 can confine the diaper so that the diaper is retained in its reduced size by the restraint and so that the diaper is returned to its nominal size upon opening of the restraint. The restraint can be a strap or a series of independent or interconnected straps, or, as shown in FIG. 11B, the restraint 94 can include a webbed material. The restraint can be formed of a material having sufficient strength to retain the diaper 12 in the reduced size, but can be removed by a consumer to release the diaper into the first, nominal size, for example by exploiting an engineered weakness, as is conventionally provided in "tear-away" packaging closures.

Figure 12:
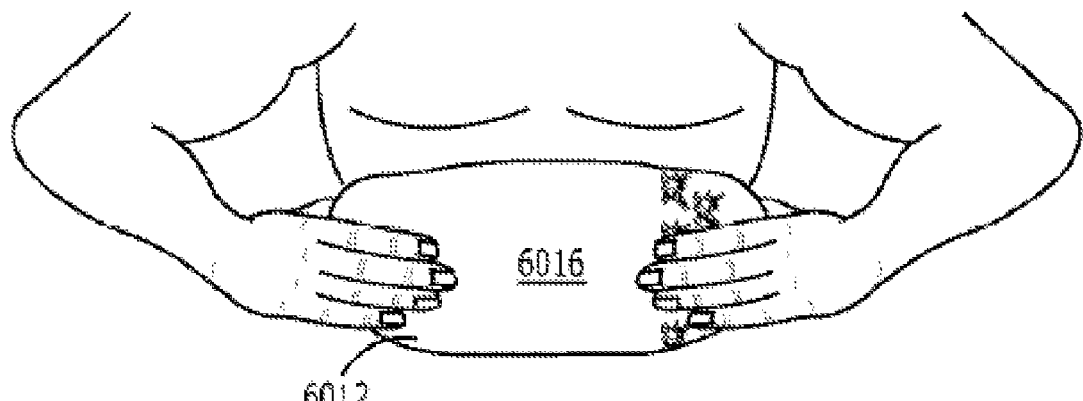
FIG. 12 is a view of a bulky diaper in the hands of a person.
Figure 13:
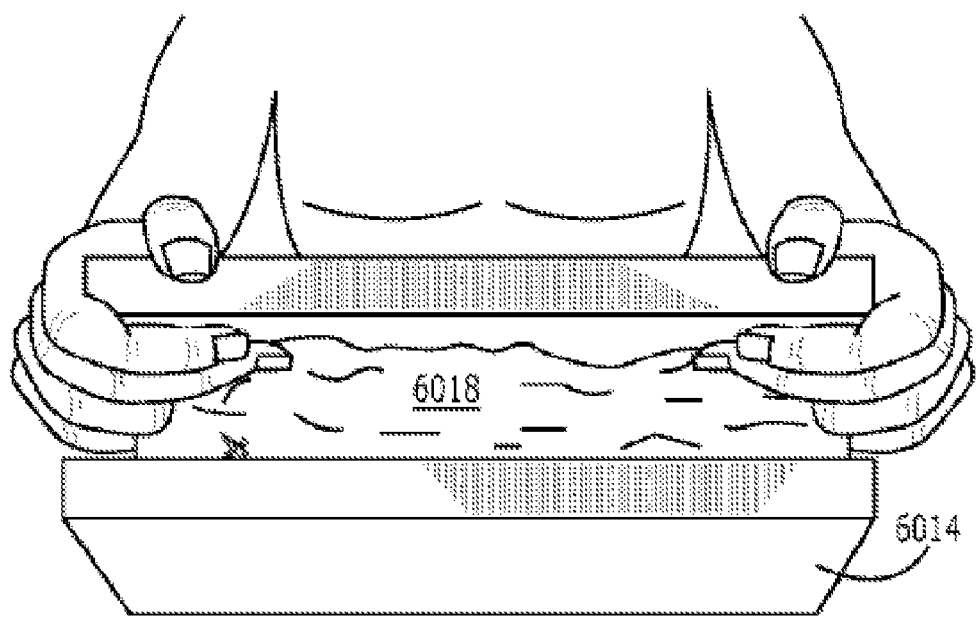
FIG. 13 is a sketch of a diaper within a jig made for holding and folding said diaper, with a person tucking the rough edges inwardly.

An embodiment of a method for packaging a diaper very compactly by folding and vacuum-sealing is shown in FIGS. 12-19. First, a bulky diaper 6012 as shown in FIG. 12 is inserted into a U-shaped elongated open-ended forming jig 6014 as shown in FIG. 13 with the outside 6016 of diaper facing down into the jig and the inside 6018 of the diaper facing up and out of the jig. The ragged elastic banded edges of the diaper are tucked inward so as to obtain a smooth clean line exterior.

Figure 14:
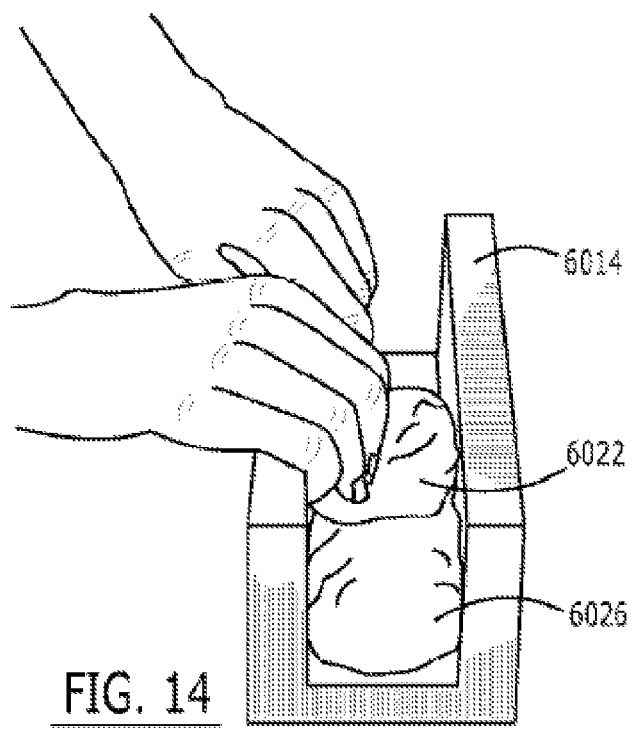
FIG. 14 is a view of a diaper with one end being folded inward.
Figure 15:
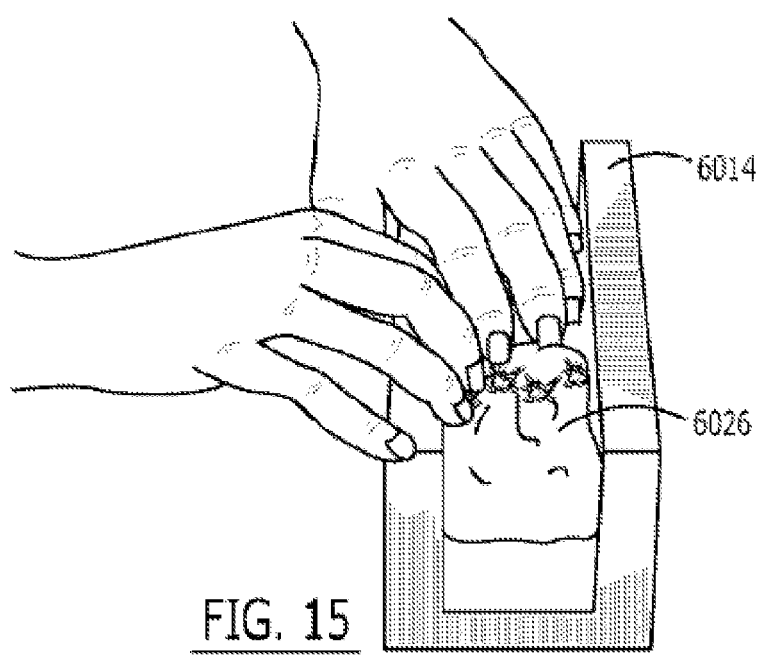
FIG. 15 is a view of a diaper with the other end being folded inward over the first fold.

Thereafter, as shown in FIG. 14, a first end, such as end 6022, then is folded inwardly covering a middle portion of the diaper, and then the other end 6026 is folded in over the first end 6022 and middle portion to form a rectangular shape of the diaper as shown in FIG. 15.

Figure 16:
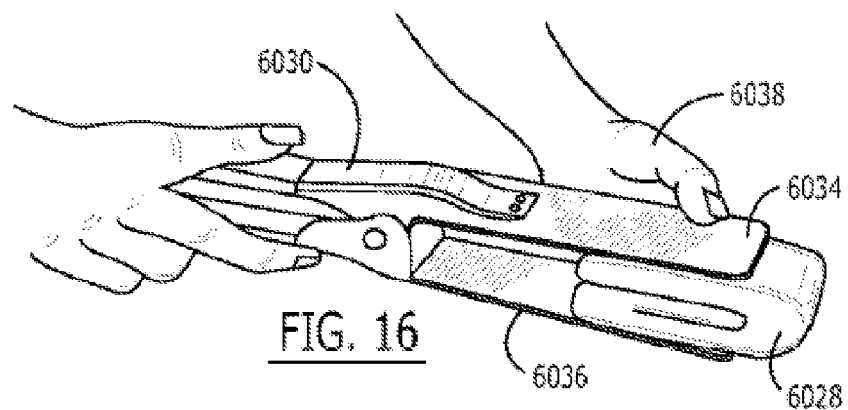
FIG. 16 shows a hand clamp gripping a folded diaper.

A spring-tensioned hand-clamp 6030 then is opened to receive the completely folded diaper between an upper flat rectangular jaw 6034 and a lower jaw 6036, as shown in FIG. 16. Furthermore, the clamp 6030 and a hand 6038 each compress the diaper 6028 as shown in FIG. 16.

Figure 17:
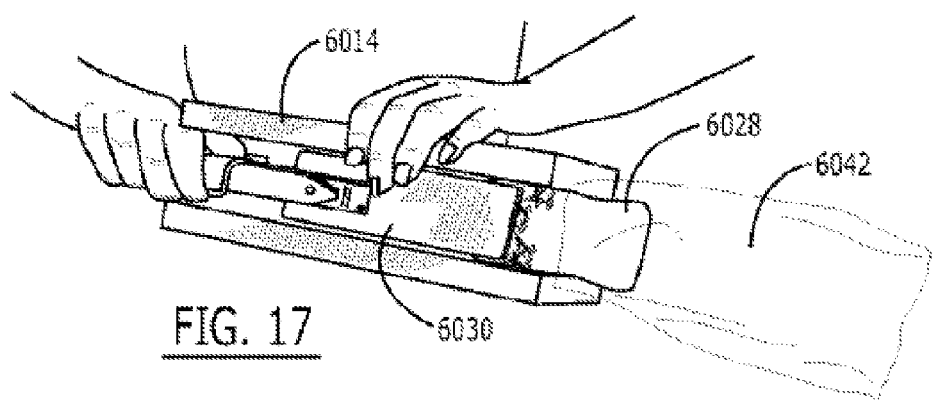
FIG. 17 is a perspective view of a folding jig facilitating the hand clamp for inserting a diaper into a plastic bag.
Figure 18:
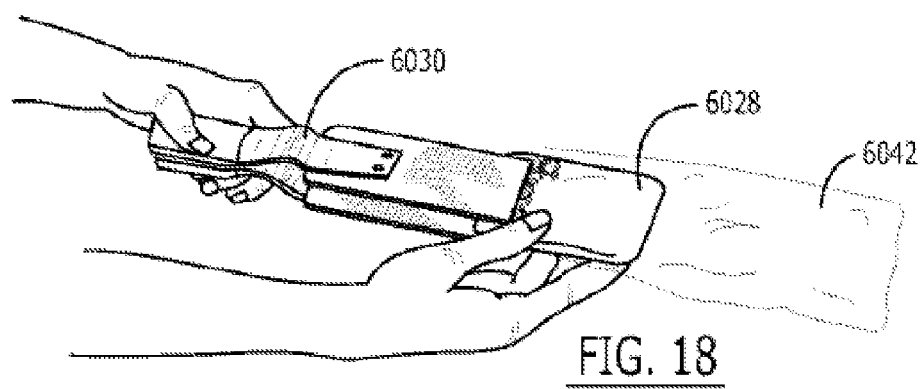
FIG. 18 shows a hand clamp held by a person compressing a folded diaper being inserted into a plastic bag.
Figure 19:
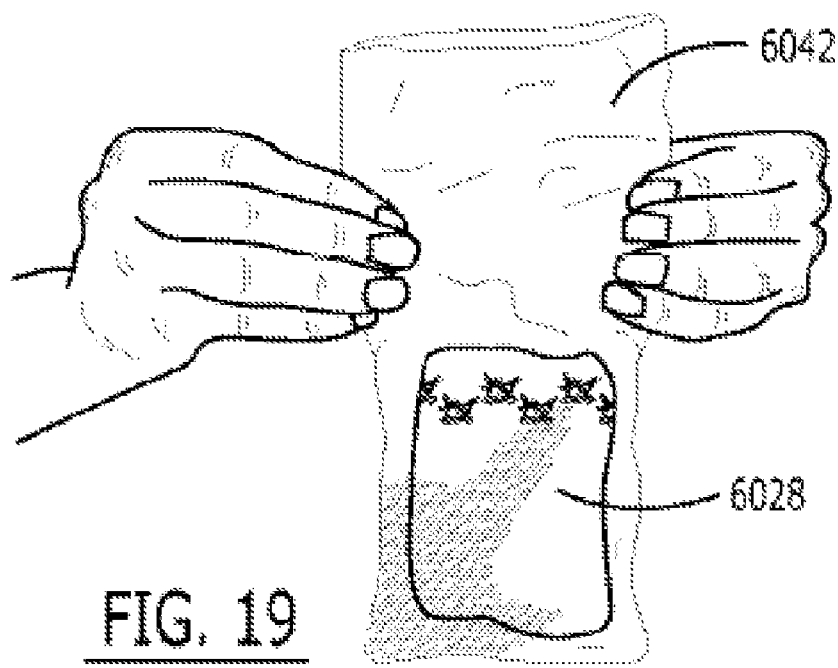
FIG. 19 shows a folded and compressed diaper within a small plastic bag.

The compressed, folded diaper 6028 then is inserted into an open end of a pliable, resilient bag 6042. The diaper is inserted into the bag using the hand clamp 6030 and jig 6014 to facilitate the insertion as shown in FIG. 17, or, alternatively, as shown in FIG. 18, the compressed, folded diaper 6028 is directly inserted into the open-ended bag 6042 without the jig.

The folded diaper 6028, fully inserted into the bag 6042 (FIG. 19), is then placed onto the deck of a conventional vacuum-sealing machine, such as a vacuum sealing-machine sold under the trademark SUPERVAC. The lid of the machine is fastened down and the vacuum-sealing machine vacuum-seals and cuts the bag to form a finished product as shown in FIG. 20.

The finished product is very firm and dense, looks like a taffy candy bar, and is comparable in size to a candy bar. In one embodiment, the finished product, i.e., a vacuum-sealed diaper package, measures approximately 1 inch by 2 inches by 1½ inches, and fits into a box for convenient carrying within a purse.

Figure 20:
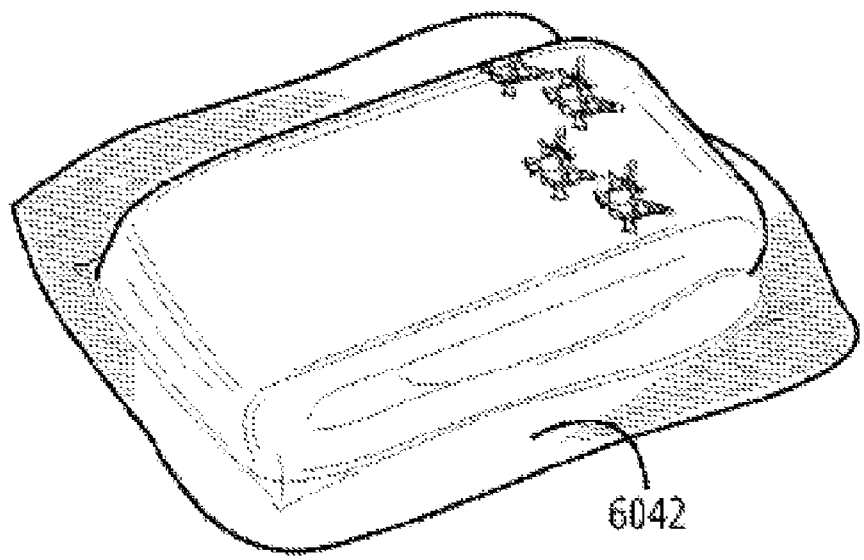
FIG. 20 shows a folded, compressed, and vacuum-packed diaper within the plastic bag of FIG. 19 after vacuum-sealing.

Additionally, printing on the outside of the diaper is visible through the bag 6042 as shown, for example, in FIG. 20. Alternatively, the printing on the outside of the diaper may be disposed within the folded diaper by first folding end 6026 inwardly covering a middle portion of the diaper and then folding the end 6022 in over the end 6026 and middle portion to form the rectangular shape of the diaper.

Figure 21A:
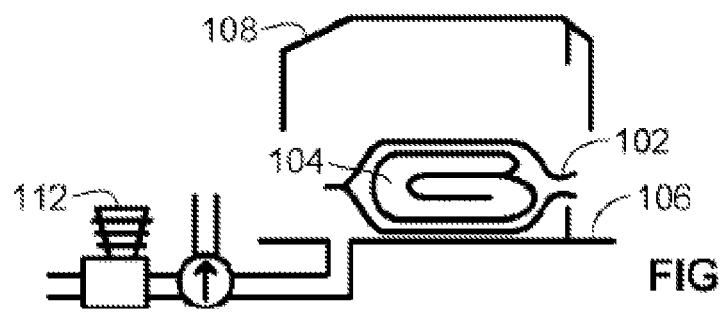
FIG. 21A is a schematic view of one step of a method of packaging a diaper.
Figure 21B:
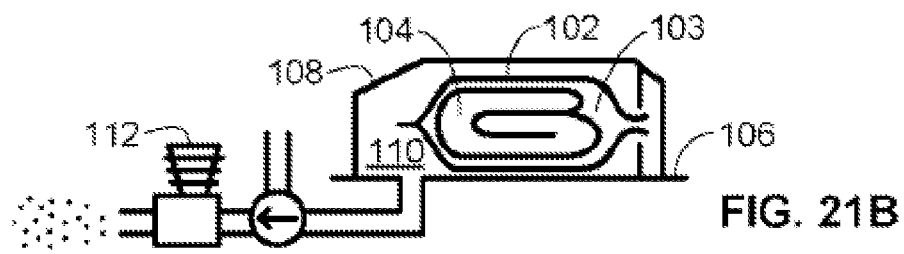
FIG. 21B is a schematic view of another step of the method of FIG. 21A.
Figure 21C:
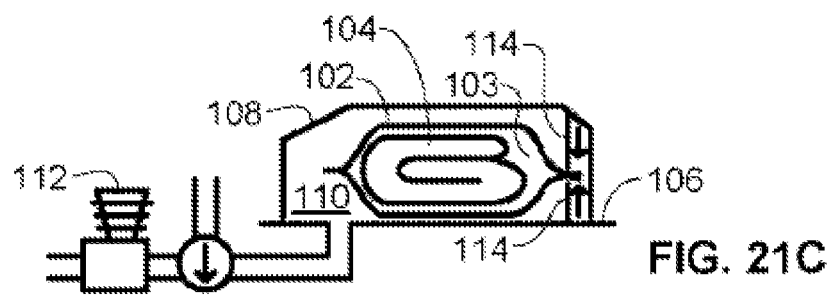
FIG. 21C is a schematic view of another step of the method of FIG. 21A.
Figure 21D:
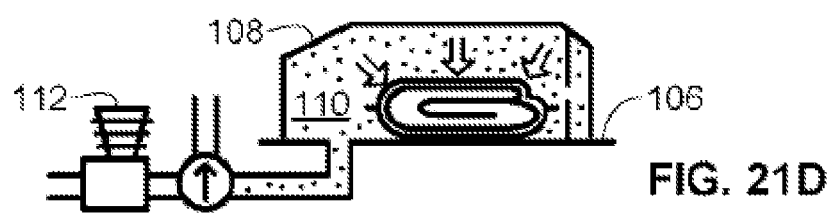
FIG. 21D is a schematic view of another step of the method of FIG. 21A.
Figure 21E:
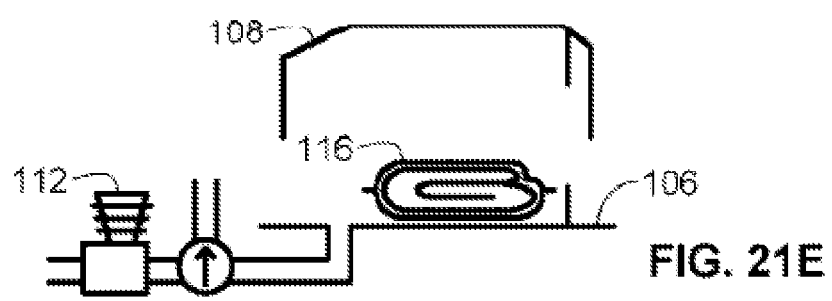
FIG. 21E is a schematic view of another step of the method of FIG. 21A.

One or more embodiments of the invention relate to a method of packaging a diaper using a conventional vacuum-sealing machine. As shown in FIG. 21A, a compressible absorbent diaper 104 is disposed within a flexible substantially air impermeable encasement 102 and the unsealed encasement 102 with the diaper 104 therein is then placed onto the deck 106 of the vacuum-sealing machine. The lid 108 of the machine is then lowered as shown in FIG. 21B establishing a seal with the deck to define a chamber 110 with the unsealed encased diaper within the chamber. A pumping system 112 then evacuates ambient air from the chamber 110 creating a vacuum state within the chamber and within the interior space 103 defined by the encasement with the diaper 104 therein. Sealing bars 114 then seal the encasement as shown in FIG. 21C such that the interior space of the substantially air impermeable encasement 102 is completely sealed and such that the compressible absorbent diaper 104 is completely enclosed within the sealed interior space 103. As shown in FIG. 21D, ambient air pressure is then restored to the chamber effecting a pressure differential across the sealed encasement that acts upon the encasement to compress the compressible absorbent diaper 104 and maintains the diaper in a reduced volume (FIG. 21D) that is less than the volume of the diaper at the time the encasement was sealed (FIG. 21C, before ambient air pressure was restored to the chamber). As shown in FIG. 21E, the lid 108 is then raised and the vacuum-packed diaper 116 is available for removal from the machine.

In addition to all of the foregoing, various preferred methods of vacuum-packing a diaper also may include pressing at least a portion of a vacuum-packed diaper and/or its encasement with a smooth surface in order to achieve a smooth planar for aesthetic appeal. Indeed, as will now be appreciated by the Ordinary Artisan in view of the foregoing disclosure, a compressible article such as a diaper that is vacuum-packed will exhibit wrinkling and bunching. Furthermore, an air impermeable encasement enclosing such an article will conform to any such bunching and wrinkling of the contained diaper as well as will be prone to forming its own undesirable wrinkles, puckers, and other undesirable flaws during vacuum-packing. One or more preferred embodiments address this aesthetic concern by pressing at least a portion of the diaper and/or encasement in order to flattening a face of the diaper and/or encasement. The pressing may occur before vacuum-packing, after vacuum-packing, during vacuum-packing, or any combination thereof.

For example, in FIGS. 13-15, portions of the outside of the diaper are pressed by the floor of the U-shaped jig as the diaper is foldedly reduced in the jig. For further example, as shown in FIG. 16, prior to being disposed within an encasement, the diaper is pressed within the clamp 6030 between the flat jaws thereof that comprise essentially planar surfaces. As further shown in FIG. 18, the clamp can be used to press at least a portion of the diaper while the diaper is being inserted into and/or is otherwise disposed within an encasement.

Figure 22:
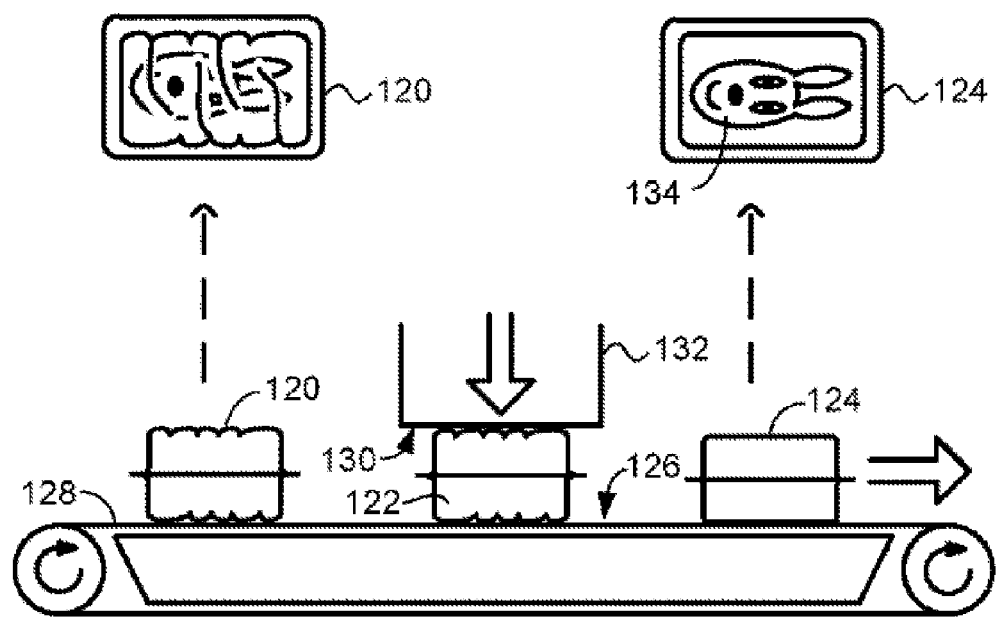
FIG. 22 is an illustration of a method for pressing a vacuum-packed diaper.

In another example, as shown in FIG. 22, a vacuum-packed diaper 122 is pressed between the essentially planar surface 126 of a conveyor belt 128 and the essentially planar surface 130 of a press 132. A vacuum-packed diaper 120 prior to pressing appears wrinkled with creases in the transparent material of the encasement that tend to distort or block view of the diaper within, as shown in FIG. 22. In contrast thereto, a vacuum-packed diaper 124 after pressing exhibits an aesthetically pleasing appearance with indicia 134 printed on the diaper being visible through a substantially smooth planar face of the transparent material of the encasement. Note that in this example, the encasement of the vacuum-packed diaper is pressed by the conveyor belt and the press providing a generally smooth planar face in the top as well as the bottom of the encasement. Note furthermore that the encasement is formed of a material that is at least somewhat flexible, whereby the diaper within the encasement is pressed by the conveyor belt and press, too, resulting in generally smooth planar faces in the top and bottom of the diaper.

Figure 23:
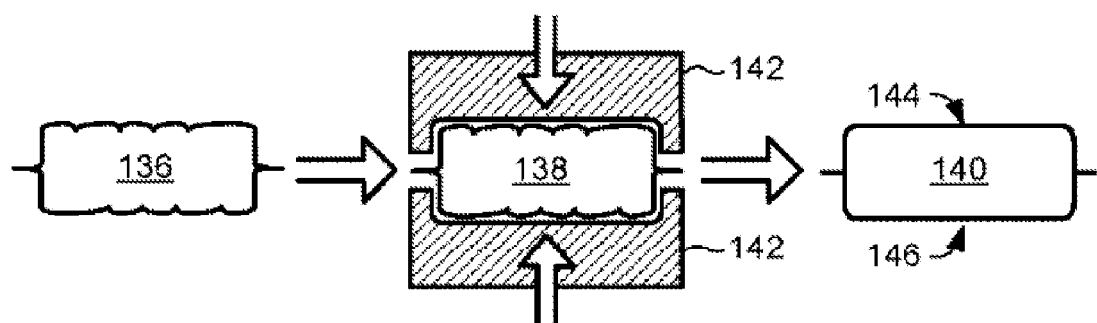
FIG. 23 is an illustration of another method for pressing a vacuum-packed diaper.

Another example of pressing is shown in FIG. 23, wherein a vacuum-packed diaper 138 is pressed between the essentially planar surfaces of a pair of presses 142. A vacuum-packed diaper 136 prior to pressing appears with wrinkles and creases whereas a vacuum-packed diaper 140 after pressing assumes a generally smooth planar appearance believed to be aesthetically pleasing. As in the previous example, the vacuum-packed diaper 140 is substantially flattened and the encasement includes generally smooth oppositely facing planar faces 144,146.

Figure 24:
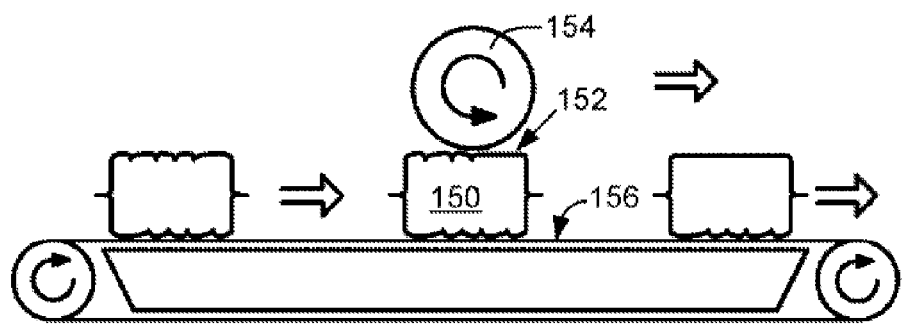
FIG. 24 is an illustration of another method for pressing a vacuum-packed diaper.
Figure 25:
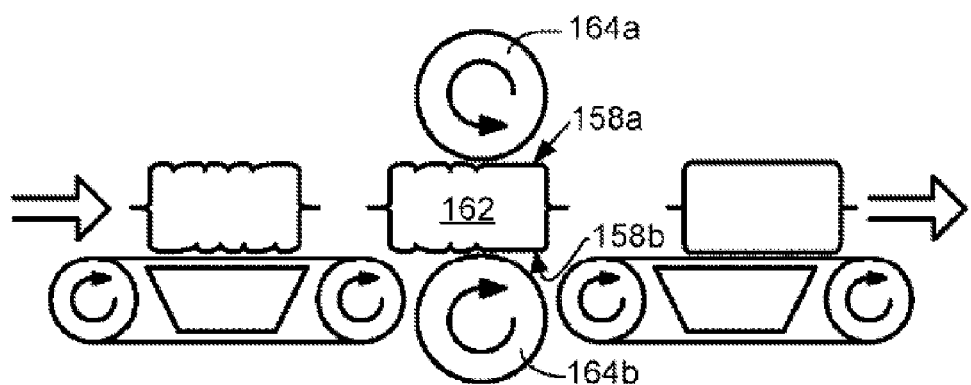
FIG. 25 is an illustration of another method for pressing a vacuum-packed diaper.
Figure 26:
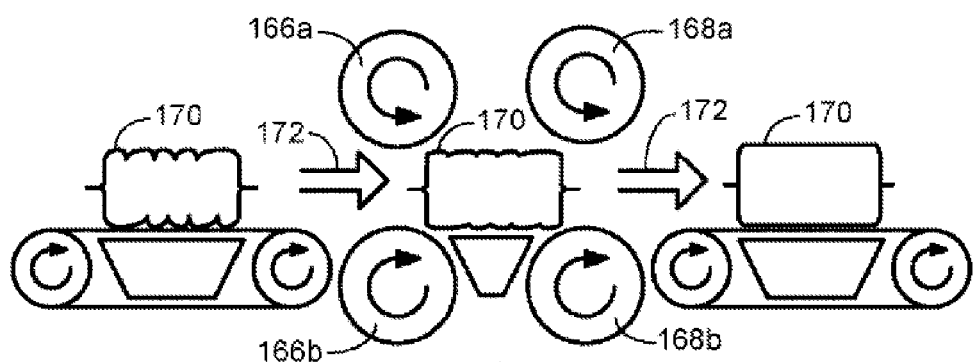
FIG. 26 is an illustration of another method for pressing a vacuum-packed diaper.

In yet other examples of pressing shown in FIGS. 24-26, vacuum-packed diapers are pressed with the generally smooth circular surfaces of rollers. In particular, in FIG. 24, an upper surface 152 of vacuum-packed diaper 150 is pressed by a roller 154 as the diaper progresses along a conveyor belt 156. In FIG. 25, respective upper and lower surfaces 158*a* and 158*b* of a vacuum-packed diaper 162 are pressed by respective opposing rollers 164*a* and 164*b*. In FIG. 26, a first pair of opposing rollers 166*a*,166*b* is sequentially arranged with a second pair of opposing rollers 168*a*,168*b* such that vacuum-packed diapers 170 are progressively smoothed in passing sequentially through the roller pairs. Moreover, the rotational speed of opposing rollers 168*a*,168*b* may be greater than the rotational speed of opposing rollers 166*a*,166*b* such that the encasement and/or diaper therein are subjected to slight horizontal forces in the direction 172 of travel of the conveyor belt, thereby further removing or pulling out wrinkles in the encasement and/or diaper.

Also in addition to all of the foregoing, various preferred embodiments may include a compressible absorbent diaper that is configured and disposed within an encasement, a portion of which is transparent such that indicia on the diaper may be viewable there through.

The indicia on the diaper may be printed and, as shown in FIGS. 27-37, the indicia may include animal characters for amusement of a child. The indicia also may be associated with a particular manufacturer or distributor of diapers and, thus, constitute a trademark. In other exemplary instances, the indicia may include brand identifiers, sizing information, or any other information that characterizes or identifies the diaper to a consumer. Indeed, the indicia may provide recognition of the article that is vacuum-sealed within the encasement, which can be especially helpful in determining the size of the diaper, since the actual size of the diaper will be difficult to judge based on the size of the vacuum-packed diaper itself.

In yet other examples, especially with regard to adult diapers, indicia of the diaper may comprise or contribute to a disguise of the diaper, thereby reducing the ability of another party to readily identify the diaper upon a glancing view or casual viewing.

Figure 29A:
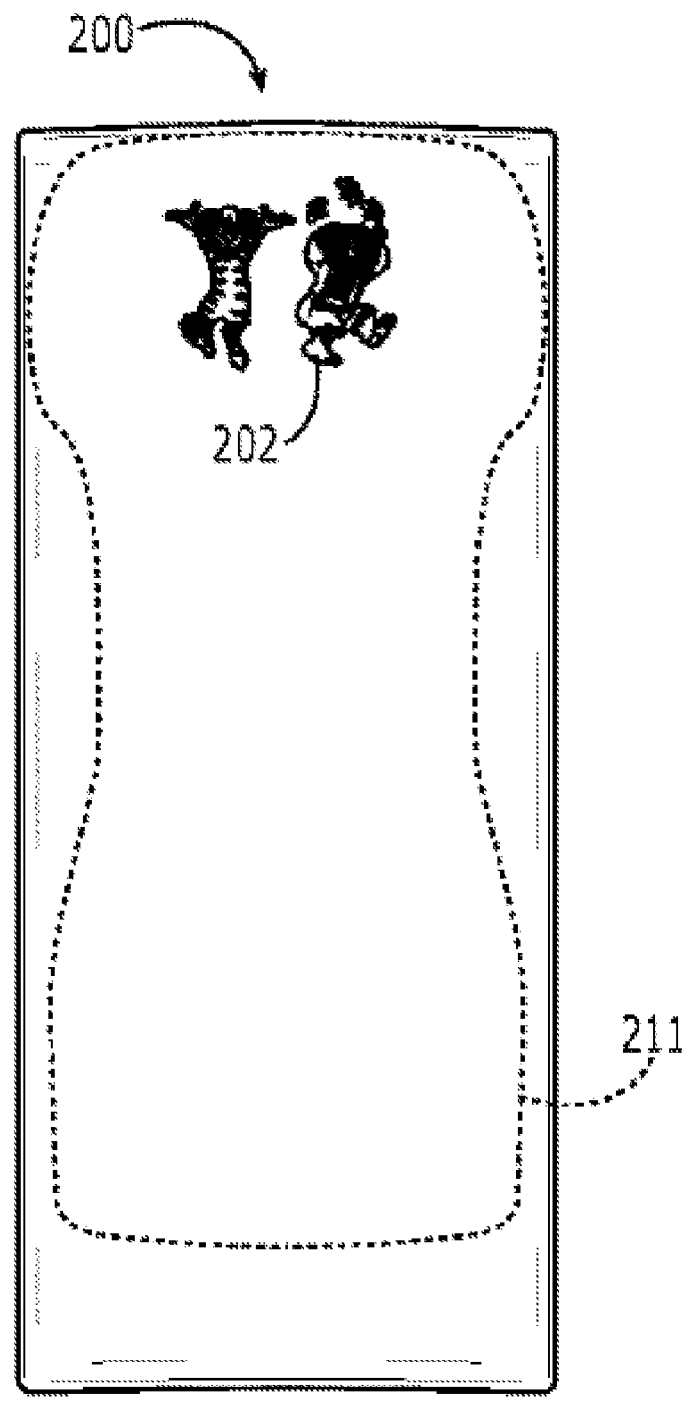
FIG. 29A and FIG. 29B are views of the diaper of FIG. 28 with tucked side margins.
Figure 29B:
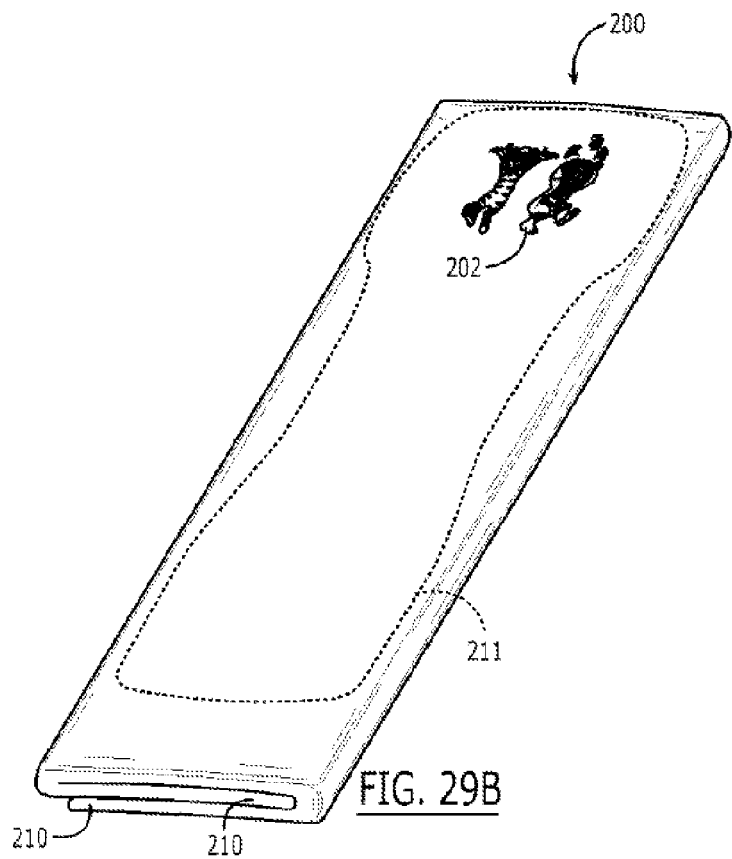

In accordance with various preferred embodiments of the invention, configuring a diaper for viewing of indicia disposed thereon may entail tucking and/or folding of the diaper for disposition within an encasement. As used herein, "tucking" refers to the tucking in of top, bottom, and/or side margins of a diaper, which margins typically constitute an elastic band, tabs, and the like. Tucking of the fully extended diaper shown in FIG. 27, for example, can result in an unfolded rectangular configuration of the diaper as shown in FIGS. 29A and 29B.

A preferred method of tucking and folding a diaper will now be described with reference to FIGS. 27-30.

Figure 27:
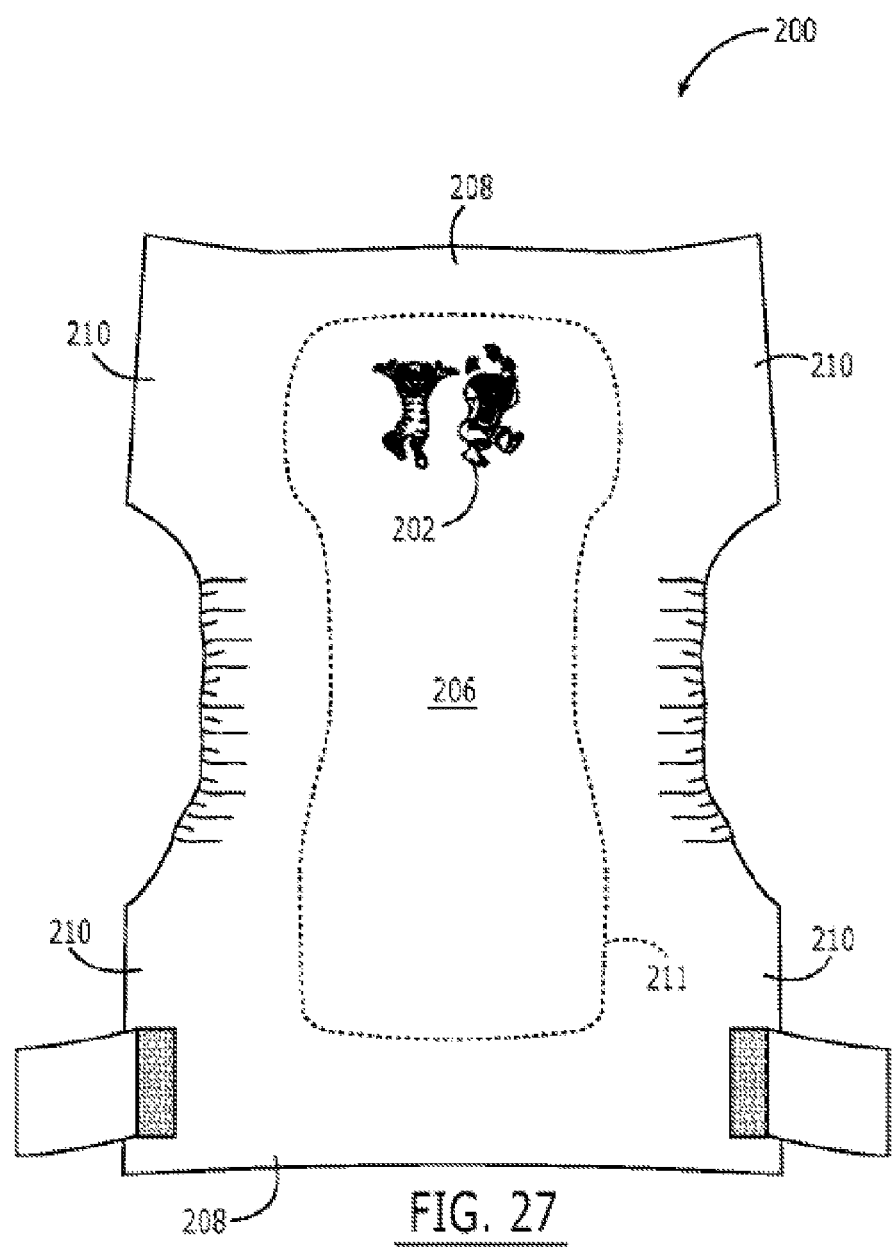
FIG. 27 is a view of a fully extended diaper having indicia thereon.

Turning to FIG. 27, a fully extended diaper 200 includes indicia 202 printed on the front portion of an outer surface 206 of the diaper. Thus, when the diaper of FIG. 27 is worn, the indicia 202 is situated proximal the groin area and navel of the wearer.

Figure 28:
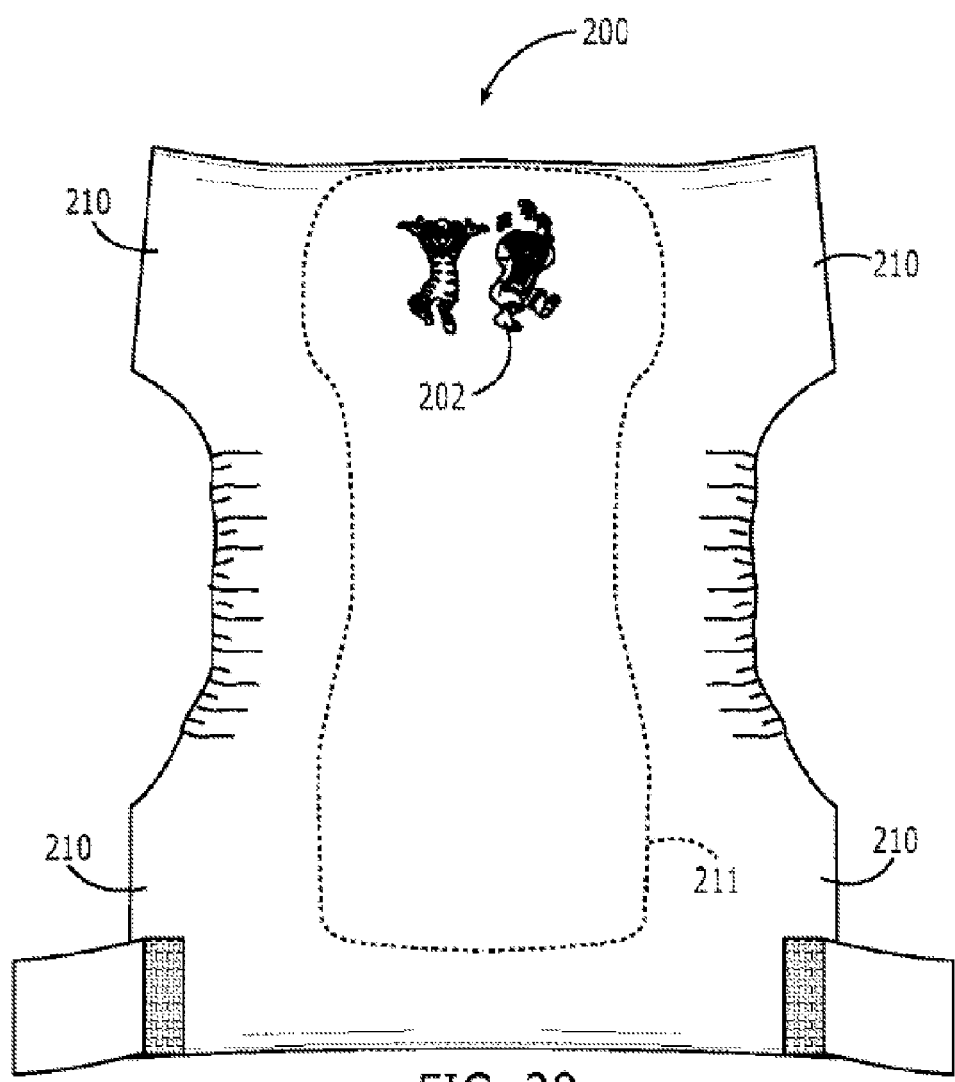
FIG. 28 is a view of the diaper of FIG. 27 with tucked end margins.

In accordance with the described preferred embodiment, end margins 208 of the diaper 200 that are visible in FIG. 27 are tucked along crosswise aspects of the diaper, whereby the end margins are disposed underneath the diaper as shown in FIG. 28. Side margins 210 that are visible in FIG. 28 also are tucked along a lengthwise aspects of the diaper, whereby the side margins are disposed underneath the diaper as shown in FIGS. 29A-29B. By tucking the side and end margins, an unfolded, generally rectangular configuration of the diaper is obtained as shown in FIG. 29A-29B. It should be noted that the tucking of end margins and/or side margins is optional in obtaining a generally rectangular configuration but is preferred due to the benefit of aesthetic presentation of the indicia. Furthermore, it should be appreciated by the Ordinary Artisan that, as shown, the tucking of end margins and side margins to obtain the unfolded rectangular configuration shown in FIGS. 29A-29B does not include folding of the absorbent area or core 211 of the diaper, which comprises the portion of the diaper that is intended to perform the absorbing function.

Figure 30:
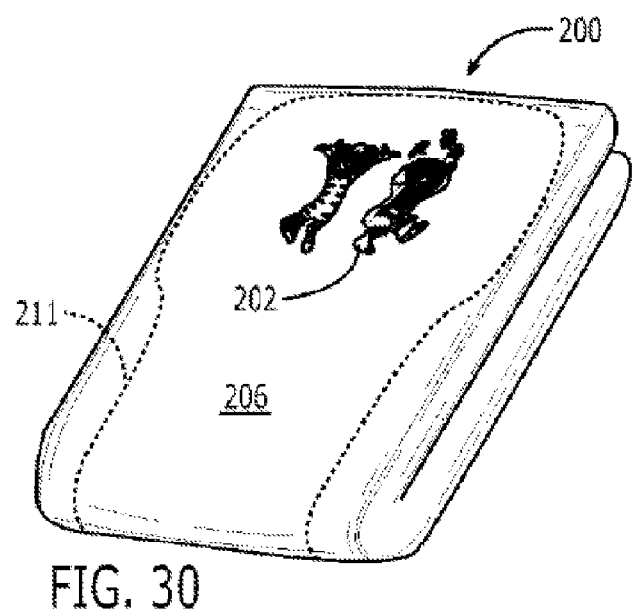
FIG. 30 is a view of the diaper of FIGS. 29A and 29B with a crosswise fold.

From the rectangular configuration shown in FIGS. 29A-29B, the diaper is folded along a centered, crosswise aspect to obtain a folded rectangular configuration in which the indicia 202 printed on the diaper is more prominently displayed, such as shown in FIG. 30. Furthermore, it will be appreciated that, in folding the diaper to arrive at the configuration shown in FIG. 30, a fold line necessarily will extend through the absorbent core 211 of the diaper.

Figure 31A:
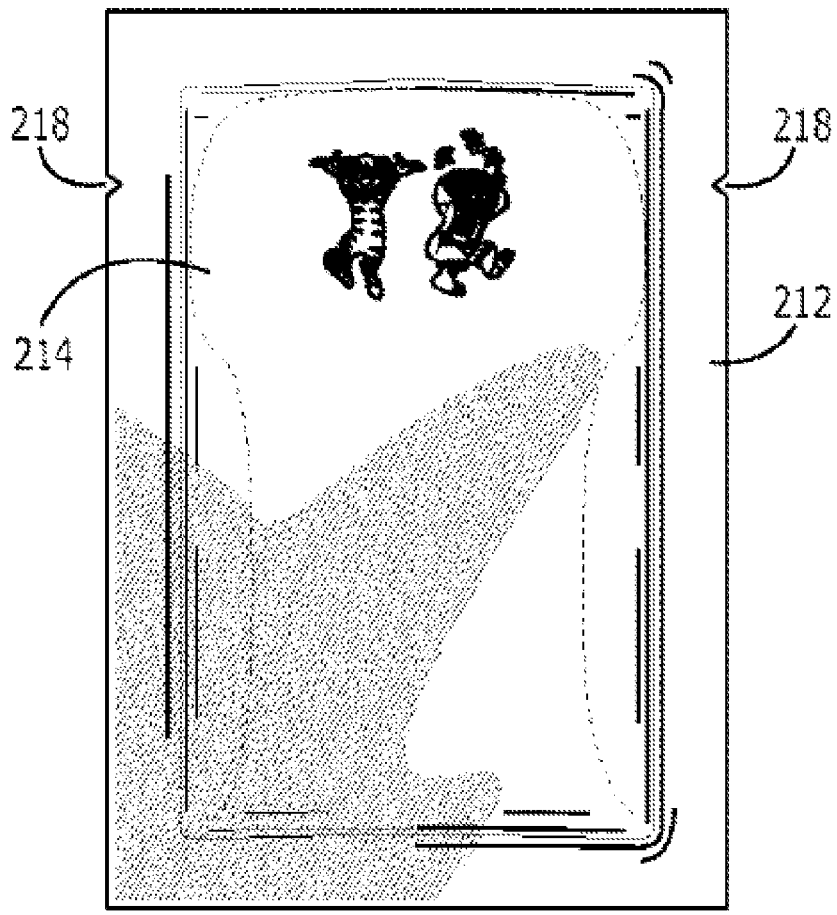
FIG. 31A and FIG. 31B are views of the diaper of FIG. 30 after vacuum-packing.
Figure 31B:
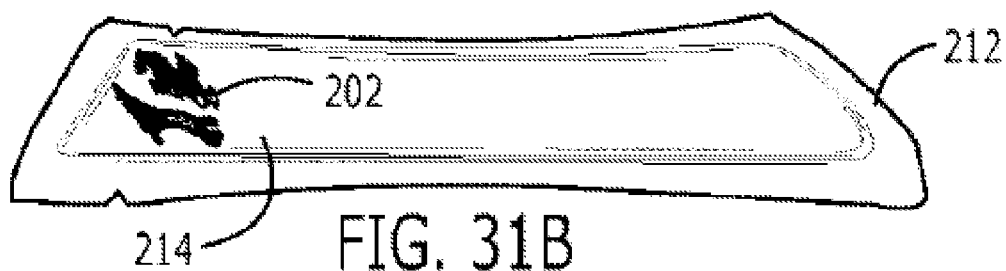

The diaper next is disposed within an air and moisture impermeable encasement and vacuum-sealed in accordance with one or more methods of the foregoing disclosure for vacuum-packing diapers. The resulting vacuum-packed diaper is illustrated in FIGS. 31A-31B, wherein the diaper of FIG. 30 has been sealed within encasement 212 having at least a portion 214 thereof that is transparent. The diaper, tucked and folded as here described, is viewable through the transparent portion 214 of the encasement and, particularly, the indicia 202 printed on the outer surface of the diaper is readily viewable through the transparent portion of the encasement. Additionally, notches 218 are formed along outer edges of the encasement 212 to aid in opening the encasement.

Figure 32:
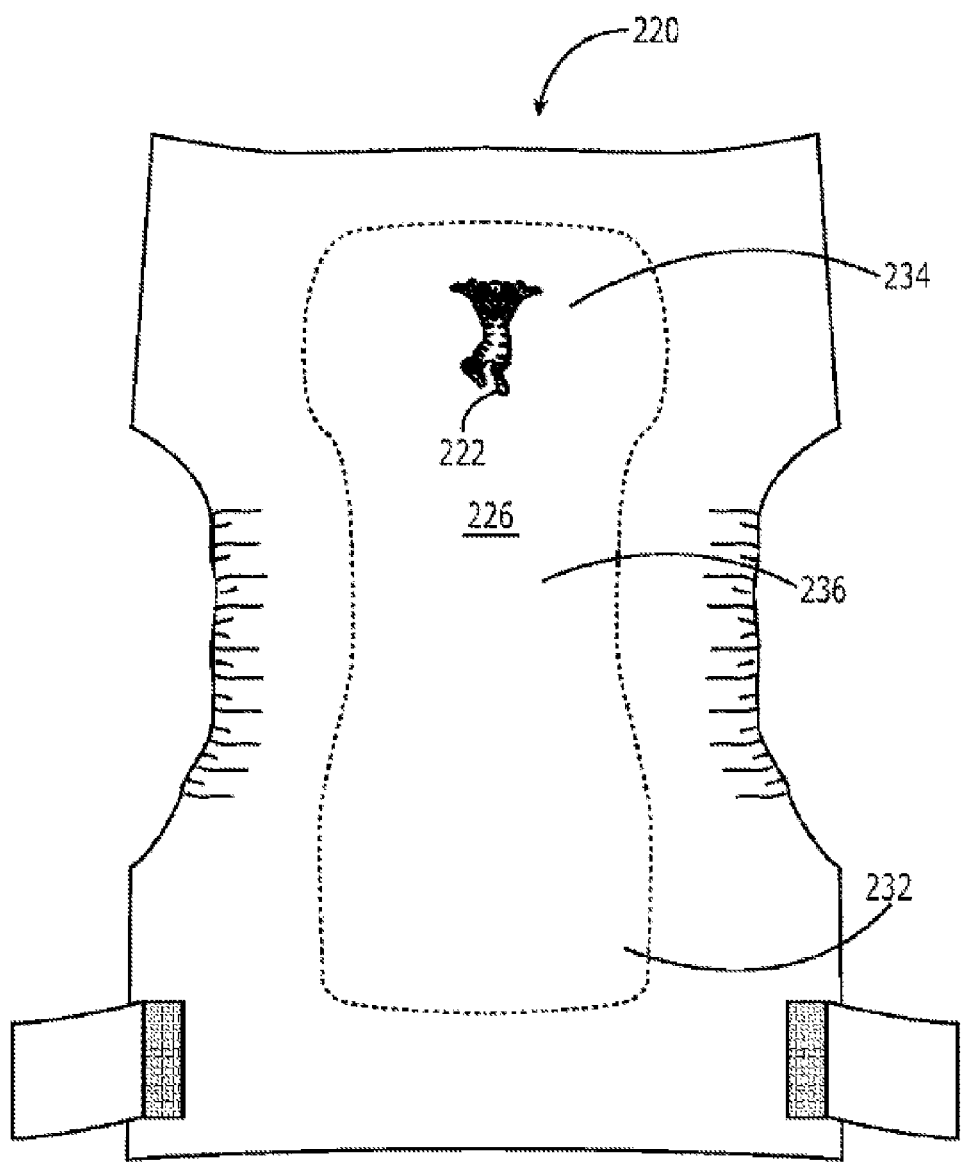
FIG. 32 is a view of another fully extended diaper having indicia thereon.
Figure 33A:
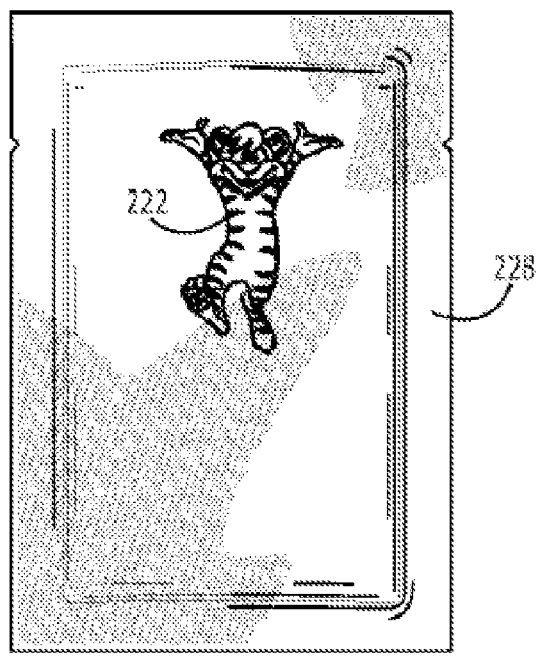
FIG. 33A and FIG. 33B are views of the diaper of FIG. 32 after tucking/folding and vacuum-packing.
Figure 33B:
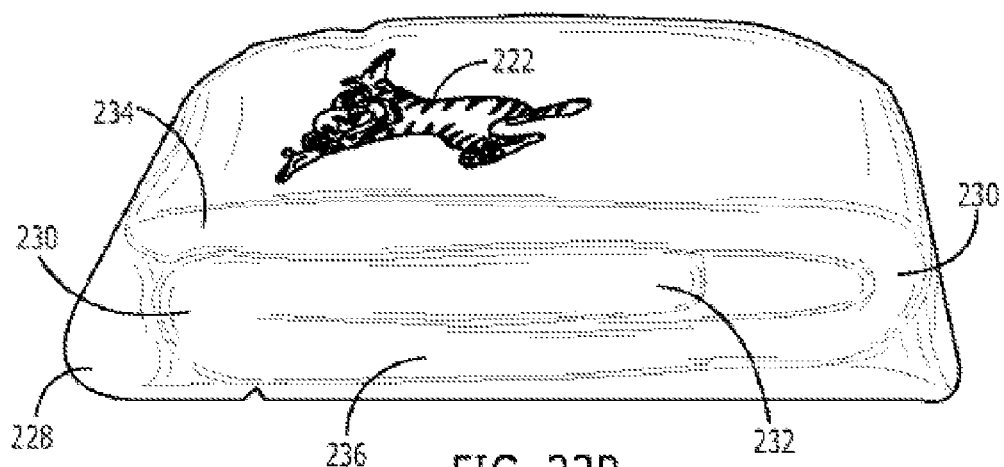

Another exemplary preferred embodiment is illustrated in FIGS. 32-33. In this case, a fully extended diaper 220 is shown in FIG. 32 with indicia 222 printed on the front outer surface 226 of the diaper. After obtaining an unfolded rectangular configuration similar to that of FIGS. 29A-29B by tucking end and side margins, the diaper 220 is twice folded along crosswise aspects (as illustrated in FIGS. 14-15) to obtain a folded rectangular configuration, and then the folded diaper is disposed and vacuum-sealed within a transparent encasement 228 resulting in the vacuum-packed diaper of FIGS. 33A-33B.

As shown in FIG. 33B, the crosswise folds 230 define a first end portion 232 of the diaper folded within the configuration, a second end portion 234 folded over the first end portion 232, and a medial portion 236 joining the first and second end portions. The first end portion 232 folded within the configuration is disposed between the second end portion 234 and the medial portion 236. The diaper, tucked and folded as here described and shown in FIGS. 33A-33B, is viewable through the encasement and, particularly, the indicia 222 printed on the outer surface of the diaper along the second end portion 234 is readily viewable through the transparent encasement and enjoys a prominent area of the viewable top surface of the diaper.

Figure 34:
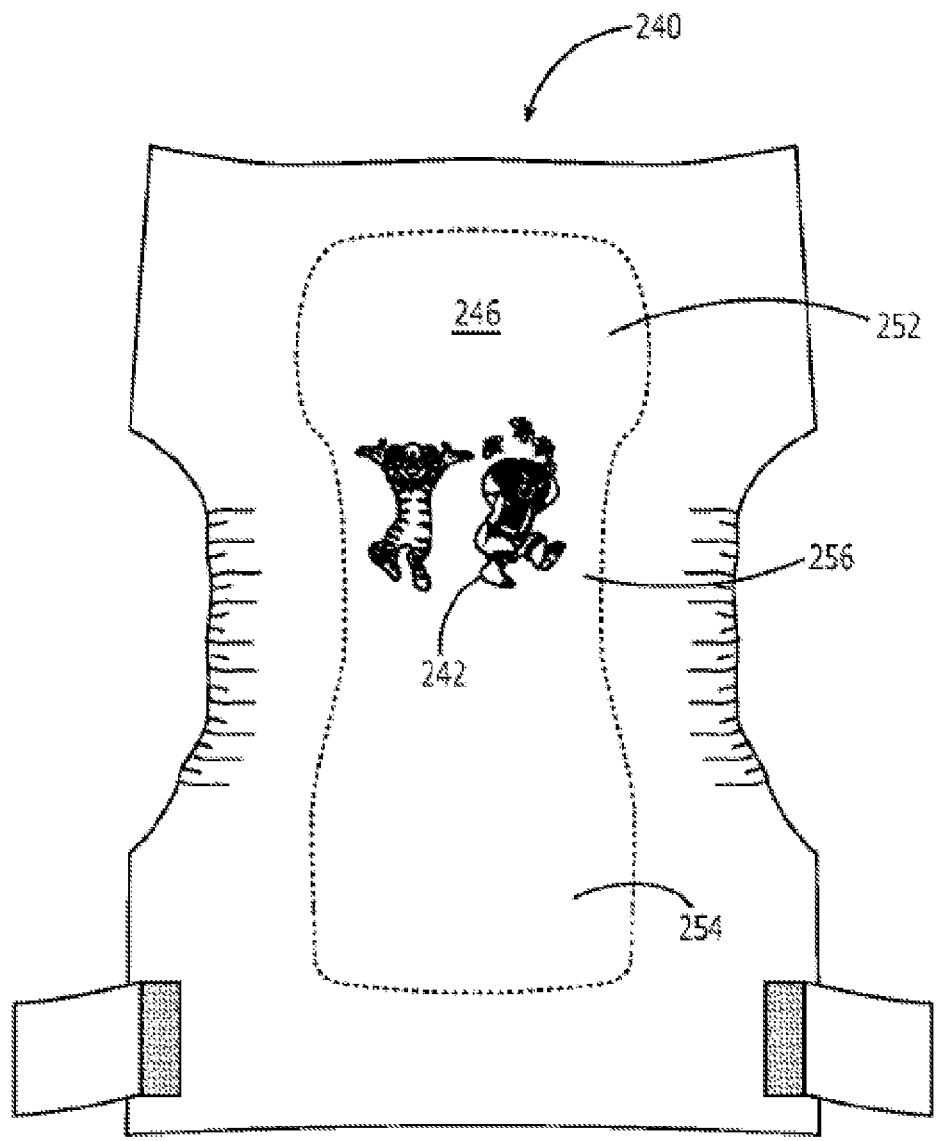
FIG. 34 is a view of another fully extended diaper having indicia thereon.

Another exemplary preferred embodiment is illustrated with reference to FIGS. 34-35. In FIG. 34, a fully extended diaper 240 is shown with indicia 242 printed on the outer surface 246 of the diaper. In this example, after obtaining an unfolded rectangular configuration similar to that of FIGS. 29A-29B through tucking end and side margins, the diaper 240 is twice folded along crosswise aspects to obtain a folded rectangular configuration, and then the diaper is disposed and vacuum-sealed within a transparent encasement 248 resulting in the vacuum-packed diaper of FIGS. 35A-35B. As shown in FIG. 35B, the crosswise folds 250 define a first end portion 252 of the diaper, a second end portion 254 folded over the first end portion 252, and a medial portion 256 joining the first and second end portions. The diaper, tucked and folded as here described and shown in FIGS. 35A-35B, is viewable through the encasement 248 and, particularly, the indicia 242 printed on the outer surface of the diaper along the medial portion 256 is viewable through the transparent vacuum-sealed encasement 248.

Figure 35A:
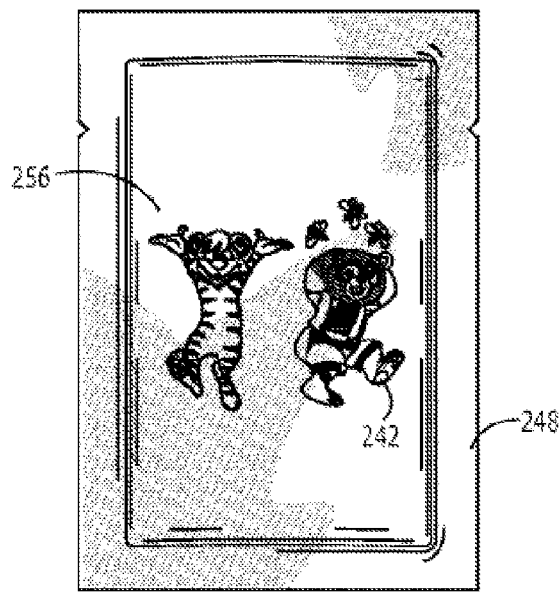
FIG. 35A and FIG. 35B are views of the diaper of FIG. 34 after tucking/folding and vacuum-packing.
Figure 35B:
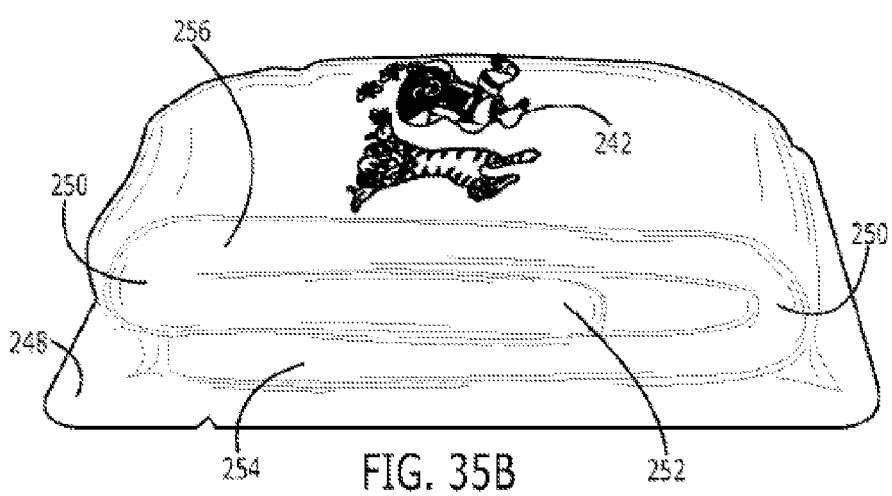

Unlike the exemplary preferred embodiment of a vacuum-packed diaper illustrated in FIGS. 33A-33B, the indicia of the vacuum-packed diaper illustrated in FIGS. 35A-35B is intended primarily for viewing in the vacuum-packed configuration as opposed to viewing when the diaper is worn, as the indicia when worn generally will face the feet of the wearer. The indicia of the vacuum-packed diaper illustrated in FIGS. 35A-35B is readily visible in the vacuum-packed configuration as well as when the diaper is worn.

In yet another example, a diaper 260 and diaper-changing accessories such as wipes 270 are disposed within a transparent encasement 268. The wipes 270 preferably are, themselves, prepackaged within a moisture impermeable encasement to avoid moisture from the wipes 270 from being absorbed by the diaper 260.

In this example, wherein the diaper 260 is tucked and folded in similar manner to that of the diaper of FIG. 33B, the wipes 270 are disposed below the medial portion 266 of the diaper within the encasement. The diaper 260, tucked, folded and disposed within the encasement 268 with the wipes 270 as shown in FIGS. 36A, 36B, and 37, is at least partially viewable through the encasement and, particularly, the indicia 262 printed on the outer surface of the diaper along the end portion 264 is viewable through the encasement 268. The wipes 270 are arranged within the encasement so as not to obstruct the view through the encasement of the indicia printed on the diaper.

In addition to the arrangement of the diaper 260 and wipes 270 within the encasement 268, it should also be noted that notches 272 also are formed along outer edges of the encasement 268 as shown in FIGS. 36A, 36B, and 37 to aid in opening the encasement. Furthermore, a weakened line 274 in the encasement 268 is formed in the material of the encasement as an engineered weakness to further aid in opening the encasement by providing a "tear-away" portion 276 of the encasement.

While many embodiments of the invention relate generally to volumetrically reducing absorbent articles, especially by vacuum-packing, for convenience in carrying and storing of the absorbent articles by consumers, such absorbent articles can be conveniently, comfortably, and discreetly concealed, carried and stored. This is especially beneficial to adult consumers in the incontinent adult market, who may want to avoid public knowledge of their use of certain absorbent articles. Such absorbent articles for incontinent adults comprise, for example, diapers, underpants, pant liners, feminine pads, and male pouches.

Unfortunately, simply concealing and carrying of a volumetrically reduced absorbent article does not preclude revelation of the article upon casual observance such as, for example, when the article is accidentally spilled from a purse or bag along with other contents, or when the article falls from a pocket during physical activity. Such times can be embarrassing for adult consumers.

To address such embarrassing incidents particular embodiments of the invention relate to disguisedly packaged absorbent articles. According to such particular embodiments, discretion and concealment is attained by way of a disguisedly packaged absorbent article having an outward appearance capable of deceiving a casual observer. In this regard, a disguisedly packaged absorbent article may be casually observed without being correctly identified. That is, a disguisedly packaged absorbent article preferably hides in plain sight.

Turning to the drawings, an exemplary package 300 comprising a disguisedly packaged diaper that has been volumetrically reduced is shown in FIGS. 38-39. Preferably, the diaper is disposed within encasement 304 in the exemplary configuration 306 shown in FIG. 40, which comprises at least two folds that enable the diaper to obtain an outward shape similar to that of a filled candy bar like a "Snickers" (™) candy bar. Furthermore, the encasement 304 preferably has disguising indicia 302 printed thereon that facilitates the deception of an unknowing observer with regard to the actual contents of the package 300. In this respect, the package 300 preferably visually resembles a wrapped candy bar in size, shape, and/or indicia thereon. The printed indicia illustrated ("CANDY BAR") is intended to represent any indicia that may suggest that the package is a wrapped candy bar.

In this exemplary package 300, the absorbent article preferably comprise a diaper that is vacuum-sealed within the encasement 304 in accordance with preferred embodiments discussed above.

Another exemplary package 320 comprising a disguisedly packaged diaper that has been volumetrically reduced is shown in FIG. 41. In this example, the diaper 326 is disposed within a first encasement 324 in a volumetrically reduced configuration as shown in FIG. 42. The volumetrically reduced configuration of the diaper 326 preferably comprises at least one crosswise fold obtaining an outward shape like that of a planar (non filled) candy bar like a "Mr. Goodbar" (™) candy bar. A secondary encasement 328 (FIG. 41) is wrapped and folded about the first encasement 324 and has disguising indicia 322 printed thereon that facilitates the deception of an unknowing observer with regard to the actual contents of the package 320. In this respect, the package 320 preferably visually resembles a wrapped candy bar in size, shape, and/or indicia thereon. The printed indicia illustrated ("CANDY BAR") is intended to represent any indicia that may suggest that the package is a wrapped candy bar.

In this exemplary package 320, the diaper preferably comprise a diaper that is vacuum-sealed within the encasement 324.

Yet a third exemplary package comprising a disguisedly packaged diaper that has been volumetrically reduced is shown in FIGS. 43-44. In this example, the volumetrically reduced diaper 342 is disposed within a primary encasement 346. The primary encasement 346 then is disposed within a secondary encasement forming the package 340. Furthermore, the secondary encasement includes disguising indicia that facilitates the deception of an unknowing observer with regard to the actual contents of the package 340. In this respect, the package 340 preferably visually resembles a pack of cigarettes in size, shape, and/or indicia thereon. The printed indicia illustrated ("CIGARETTES") is intended to represent any indicia that may suggest that the package 340 is a pack of cigarettes.

In this exemplary package 340, the diaper preferably comprise a diaper that is vacuum-sealed together with accessories 344, such as wipes, within the encasement 324.

Still yet another exemplary package comprising a disguisedly packaged diaper that has been volumetrically reduced is illustrated by FIGS. 45-49. In this example, a volumetrically reduced diaper 422 is disposed within an encasement 424. The encasement 424 comprises a pair of opposing shells 426,428 and a clamping band 430. As illustrated by FIGS. 48-49, the clamping band 430 aids in maintaining the relative positions of the shells and keeping the volumetrically reduced diaper 422 contained between the shells. In particular, respective extensions 432,434 of the shells 426,428 are received within channels (not shown) of the clamping band 430 such that the clamping band 430 slides over the extensions 432,434 for retention therein.

The diaper 422 is disposed within the encasement 424 in a volumetrically reduced configuration by way of, for example, the process illustrated in FIGS. 10A-10E discussed above, and may or may not include vacuum-packing of the absorbent article. The diaper 422 is removed from the encasement 424 by removing the clamping band 430 from and separation of the shells 426,428.

The encasement and, in particular, the shells 426,428 include an outward appearance similar to that of a mobile telephone in size, shape, and/or indicia thereon. For example, indicia 438 on shell 428 resembles the keys of a keypad. The area of shell 428 comprising the buttons further may be raised or may comprise components of a different material in order to give a convincing appearance of a keypad. A screen further may be imitated by the shape and/or indicia of the shell 426. Additionally, the shell 426 includes a protuberance resembling an antennae.

Another exemplary package comprising a disguisedly packaged diaper that has been volumetrically reduced is shown in FIGS. 50-52. In this example, the diaper 458 (FIG. 52) is disposed within an encasement 452. The encasement 452 comprises a pair of separable opposing shells 454,456. As illustrated by FIG. 52, the shells keep the volumetrically reduced diaper 458 contained therebetween and are separable for removing of the diaper 458 from the package. Preferably, the shells 454,456 snap into interlocking engagement with one another and can be separated by selectively applied force at the areas of the interlocking engagement. Moreover, such type of engagement is conventional and therefore is not further discussed herein.

The diaper 458 is disposed within the encasement 452 in a volumetrically reduced configuration by way of, for example, the process illustrated in FIGS. 10A-10E discussed above, and may or may not include vacuum-packing.

The encasement 452 and, in particular, the shells 454,456 include an outward appearance similar to that of a personal pager in size, shape, and/or indicia thereon. For example, indicia on and or the shape of shell 456 exhibits the resemblance of keys and a screen of a pager. Additionally, the shell 454 includes a belt clip 462 that resembles the belt clip of a pager.

While many embodiments relate generally to volumetrically reduced absorbent articles that can be conveniently carried and stored, particular embodiments relate to volumetrically reduced diapers for children wherein a diaper is contained within a child's toy. In this respect, the toy comprises a container for the diaper. By packaging a diaper within a toy, a toy is conveniently on hand at the time of a diaper changing for amusement of the child before, during, and/or after the diaper changing.

An exemplary embodiment of a toy container in accordance with this aspect of the invention is illustrated by FIGS. 53-54 and comprises a doll 500 resembling a kangaroo in which a volumetrically reduced diaper 502 is disposed. Each of rigid upper and lower body portions 506,508 of the doll 500 defines an internal compartment 504 for receiving respective portions of the diaper 502. The upper portion 506 and lower portion 508 are separable for removal of the diaper 502.

In this exemplary embodiment, the volumetrically reduced diaper 502 is disposed within the doll 500 in a rolled, cylindrical configuration that corresponds to and fits within the cylindrical compartments 504 of the upper and lower portions 506,508. In some embodiments, the diaper 500 is vacuum-sealed within an encasement and then disposed within the doll 500; in other embodiments, the diaper 500 disposed within the doll 502 is not vacuum-sealed. A diaper also may be disposed within dolls in other configurations, especially if the compartments within the other dolls have other than cylindrical configurations. Thus, for example, a volumetrically reduced diaper may include a rectangular configuration for disposition within a rectangular compartment of a doll. Another exemplary embodiment comprising a doll 520 that also resembles a kangaroo is illustrated by FIGS. 55-56. In this example, a volumetrically reduced diaper 522 is disposed within a cylindrical compartment 524 defined by a semi-soft, integral body portion 526 of the doll 520. The compartment 524 is accessible through an opening located underneath the body portion 526 of the doll 520. The opening is closed to contain the diaper 522 within the doll 520 using closure element 528, which closure element may comprise, for example, a friction-fit plug, a threaded screw cap, or a lid that snaps into place. As with the doll 500, the diaper 522 in doll 520 is vacuum-sealed in certain embodiments and is not vacuum-sealed in other embodiments, as desired.

Another exemplary embodiment of a toy in which a volumetrically reduced diaper is disposed comprises a toy ball 540 as illustrated by FIGS. 57-60. In this embodiment, the ball 540 includes a rigid top portion 546 that is connected to a rigid bottom portion 548 by a hinging member 544 such that the top portion 546 moves about the hinging member 544 relative to the bottom portion 548. Thus, the top and bottom portions 546,548 are movable between a closed position, as shown in FIG. 58, and an open position, as shown in FIG. 59. When the ball 540 is in the closed position, closure tab 550 keeps the top portion 546 engaged with bottom portion 548 for containment of the diaper 542. The ball 540 is opened by applying inward pressure adjacent the closure tab 550 for release of the top portion 546 from the bottom portion 548. The diaper 542 is freely removable from the ball 540 when in the open position, and the diaper 542 is shown in FIG. 60.

In this exemplary embodiment, the volumetrically reduced diaper 542 is disposed within the ball 540 in a rolled, cylindrical configuration that corresponds to and fits within internal compartments of the top and bottom portions 546,548 of the ball 540. In some embodiments, the diaper 542 is vacuum-sealed within an encasement and then disposed within the ball 540; in other embodiments, the diaper 542 disposed within the ball 540 is not vacuum-sealed. A diaper also may be disposed within toy balls in other configurations, especially if the compartments within the other balls have other than cylindrical configurations. Thus, for example, a volumetrically reduced diaper may include a rectangular configuration for disposition within a rectangular compartment of a toy ball.

Yet another exemplary embodiment of a toy in which a volumetrically reduced diaper is contained comprises a toy rocket 570 as illustrated by FIGS. 61-62. The toy rocket 570 includes a cylindrical sleeve 574 that defines a compartment in which a volumetrically reduced diaper 572 is contained, as shown in FIG. 62. Furthermore, the toy rocket 570 includes a removable cap 576 that serves as the nose of the toy rocket 570 for full enclosure and containment of the diaper 572 within the sleeve 574. The volumetrically reduced diaper 572 is shown in FIG. 63 in the cylindrical configuration in which it is disposed within the sleeve 574 of the toy rocket 570. The cylindrical sleeve 574 may be flexible or, alternatively, the sleeve 574 may be flexible with the volumetrically reduced diaper 572 disposed therein providing a degree of rigidity to the sleeve 574 and overall toy rocket 570.

Still yet another exemplary embodiment of a toy in which a volumetrically reduced diaper 582 is disposed comprises a toy car 580 as illustrated by FIGS. 64-66. Like the toy ball 540 illustrated by FIGS. 57-60, the toy car 580 includes a rigid top portion 586 that is connected to a rigid bottom portion 588 by a hinging member 584 such that the top portion 586 moves about the hinging member 584 relative to the bottom portion 588. Thus, the top and bottom portions 586,588 are movable between a closed position, as shown in FIGS. 64-65, and an open position, as shown in FIG. 66. When the toy car 580 is in the closed position, closure tab 590 keeps the top portion 586 engaged with bottom portion 588 for containment of the diaper 582. The toy car 580 is opened by applying inward pressure adjacent the closure tab 590 for release of the top portion 586 from the bottom portion 588. The diaper 582 is freely removable from the toy car 580 when in the open position.

In this exemplary embodiment, the volumetrically reduced diaper 582 is disposed within the toy car 580 in a configuration that corresponds to and fits within internal compartments of the top and bottom portions 586,588 of the toy car 580. The particular configuration of the volumetrically reduced diaper is illustrated in FIGS. 67-68 and, as will be apparent, resembles the shape of the top and bottom portion 586,588 of the toy car 580. In some embodiments, the diaper 582 is vacuum-sealed within an encasement such as a flexible bag and then disposed within the toy car 580; in other embodiments, the diaper 582 disposed within the toy car 580 is not vacuum-sealed. A diaper also may be disposed within toy cars in other configurations, especially if the compartments within the other toy cars have other than cylindrical configurations. Thus, for example, a volumetrically reduced diaper may include a cylindrical or rectangular configuration for respective disposition within a cylindrical or rectangular compartment of a toy car.

Additionally, an exemplary method of making the volumetrically reduced diaper 582 of the exemplary embodiment of FIGS. 67-68 is illustrated in FIG. 69. In this regard, a mold 592 having a configuration matching that of the compartment of the top portion 586 of the toy car 580 is forcibly pressed onto the top of diaper 594 resulting in diaper 582. Furthermore, diaper 594 preferably is vacuum-sealed within an air impermeable encasement (not illustrated) during the pressing process, such that diaper 582 retains its molded configuration for later disposition within the toy car 580. This preferably is accomplished by carrying out the pressing of the mold 592 onto the diaper 594 within a vacuum chamber (represented by the rectangular box in FIG. 69). Alternatively, for example, a diaper first may be vacuum-packed and then forcibly configured into the desired configuration for disposition within a toy.

Any of the foregoing toy containers may be packaged for individual sale to consumers or packaged together for sale to consumers; however, in accordance with an aspect of the invention, such toy containers further may be sold in conjunction with packages of conventional diapers arranged together in their nominal configuration, with one or more toy containers being disposed in such packages as "prizes" similar in marketing theory to those prizes found in "Crackerjack"(™) boxes or provided in kids meals at fast food restaurants.

Still yet another aspect of the invention relates to refills for such toy containers. In this respect, once a volumetrically reduced diaper has been removed from its toy container and used, a consumer may prefer to reinsert another volumetrically reduced diaper into the toy container at a later time. Accordingly, in this aspect of the invention, packages of individual, volumetrically reduced diapers are sold as refills for such toy containers.

In addition to the above disclosure, another aspect of the invention relates to vending and, in particular, to vending systems and machines for dispensing volumetrically reduced absorbent articles such as vacuum-packed diapers. Indeed, it may be particularly beneficial to include such a vending machine in conjunction with each courtesy baby changing station commonly found in public restrooms of commercial establishments.

An exemplary vending machine 700 is shown in FIGS. 70-71. Vending machine 700 includes a structural housing 702 and multiple, slotted, currency-receiving slides 704 extending from an anterior vending face 706 of the vending machine 700. The vending machine 700 further includes viewing windows 705 for presentation of selectable products that are respectively dispensed upon actuation of the currency-receiving slides 704. Each product is dispensed for a predetermined currency amount that is optionally indicated in the respective viewing window 705 or on the respective currency-receiving slide 704.

As shown in FIG. 71, the exemplary vending machine 700 contains, in association with each currency-receiving slide, a vertical stack 708 of products 710. In selecting and purchasing a product, a consumer places currency 712 into a particular currency-receiving slide 704, actuates the slide by pressing the slide inwardly in the direction of arrow 714, and receives 716 one of the selected products 718 associated with the particular currency-receiving slide 704 through dispensing slot 712 (FIG. 70).

As further shown in FIG. 71, the exemplary vending machine 700 preferably comprises posterior access panels for secure access by a vendor or operator of the vending machine 700. In this respect, the vending machine 700 extends through a wall 720 (FIG. 71) in which it is mounted. Consequently, a vendor may securely restock (726) the vertical stack 708 with additional products 728 through a product access panel 730. Furthermore, a vendor may securely collect (732) deposited currency 734 through a currency access panel 736.

In accordance with this aspect, the products 708 dispensed by the vending machine 700 include individually packaged volumetrically reduced absorbent articles, such as diapers. The products 708 additionally may include multi-packs of volumetrically reduced absorbent articles such as diapers; kits including volumetrically reduced absorbent articles such as diapers, toys containing volumetrically reduced absorbent articles such as diapers, and disguisedly packaged absorbent articles. Moreover, products 708 that do contain volumetrically reduced diapers each preferably contains one of the many embodiments of an individually vacuum-packed diaper as previously disclosed herein.

It is to be understood that the above referenced arrangements are illustrative. It will be apparent to those of ordinary skill in the art that numerous modifications can be made without departing from the principles and concepts of the invention.

Turning now to FIGS. 72-103, a combination package for retail sale (hereinafter "COMBO PACK") includes reduced and non-reduced articles and, in particular, reduced diapers and non-reduced diapers. Reduced diapers are provided within restraining encasements for convenient carrying. A reduced diaper, once removed from the restraining encasement, is capable of being expanded to a non-reduced configuration for use. Each diaper preferably is reduced by being vacuum-packed. A COMBO PACK may include any number of vacuum-packed and non vacuum-packed diapers. The foregoing will be more readily understood upon consideration of the drawings and the following detailed description.

An embodiment of a COMBO PACK of absorbent articles comprising diapers is show in FIG. 72. The COMBO PACK includes a first package and a second package removably attached together by an adhesive or other attachment. The first package contains non vacuum-packed diapers, and the second package contains one or more individually vacuum-packed diapers. In FIG. 73, a vacuum-packed diaper is visible through a tear-away portion of the second package. In FIG. 74, the vacuum-packed diaper is shown removed from the second package.

The vacuum-packed diaper in FIGS. 73 and 74 is contained in a transparent restraining encasement. The vacuum-packed diaper is folded within the restraining encasement such that graphical indicia of the article are visible through the encasement. Thus, the graphical characters printed on the diapers are prominently displayed through the transparent encasement in which the diaper is vacuum packed. Preferably, the diaper is specifically configured during vacuum-packing for such prominent display.

The encasement restrains the vacuum-packed diaper in a configuration that is reduced in area and volume. In the example shown in FIGS. 73 and 74, the reduced diaper is folded and contained in an encasement that is vacuum-sealed. In other examples (not shown), diapers are retained in reduced configurations that are folded, compressed, and folded and compressed, all with and without vacuum-sealing. Diapers that are reduced and restrained in encasements with and without vacuum-sealing are described above in connection with FIGS. 1-71 and below in connection with FIGS. 104-129.

In FIG. 75, another embodiment of a COMBO PACK includes a first package and a transparent restraining encasement that contains a vacuum-packed diaper. The encasement is attached to the first package by an adhesive or other similar attachment means.

In FIGS. 76-77, yet another embodiment of a COMBO PACK includes a vacuum-packed diaper and a number of non vacuum-packed diapers all contained within a first package. The vacuum-packed diaper is contained within a restraining encasement that is placed within the first package together with the non vacuum-packed diapers. In FIG. 78, the vacuum-packed diaper within its restraining encasement is shown removed from the first package and placed alongside a non vacuum-packed diaper that also has been removed from the first package. The vacuum-packed diaper, once removed from the restraining encasement, is capable of being expanded to a non-reduced configuration for use similar to the configuration of the non vacuum-packed diaper shown in FIG. 78.

In FIG. 79, yet another embodiment of a COMBO PACK includes a number of non vacuum-packed diapers and a "bi-pack" or "twin pack" of vacuum-packed diapers within a first package. The bi-pack consists of two diapers that have been vacuum packed together within the same encasement. Each of the vacuum-packed diapers includes a "C" shaped folded configuration.

In FIG. 80 an opened first package containing a number of non vacuum-packed diapers is shown with several examples of a vacuum-packed diaper within a restraining encasement. A COMBO PACK according to the invention may include any number of vacuum-packed diapers and any number of non vacuum-packed diapers. In some embodiments, a COMBO PACK according to the invention includes more non vacuum-packed diapers than vacuum-packed diapers.

Thus, for example, in a particular embodiment, a COMBO PACK includes several dozen non vacuum-packed diapers and one vacuum-packed diaper. In another particular embodiment, a COMBO PACK includes several dozen non vacuum-packed diapers and two vacuum-packed diapers in the same encasement. In yet another particular embodiment, a COMBO PACK includes several dozen non vacuum-packed diapers and six individually vacuum-packed diapers. In yet other particular embodiments (shown in subsequent figures), vacuum-packed diapers are provided in containers that further include such items as diaper-changing accessories, baby feeding supplies, and disposal bags, thereby forming kits.

In FIG. 81, an embodiment of a COMBO PACK includes, within a first package, a number of non vacuum-packed diapers and a second package. One or more individually vacuum-packed diapers are contained within the second package.

In FIGS. 82 and 83, an embodiment of a COMBO PACK includes first package that contains a number of non vacuum-packed diapers and a vacuum-packed diaper contained within a restraining encasement that is removably attached to the first package by a peel-away film.

In FIG. 84, a COMBO PACK is shown that includes a vacuum-packed diaper and a number of non vacuum-packed diapers within a first package. The vacuum-packed diaper is contained within a restraining encasement that is placed within the first package.

In FIG. 85, a COMBO PACK is shown that includes a number of individually vacuum-packed diapers disposed within a dispenser that, together with a number of non vacuum-packed diapers, is disposed within a first package. In FIGS. 86-87 the dispenser is shown removed from the first package. In this embodiment, the dispenser contains six individually vacuum-packed diapers and is referred to as a "6-Pack". An opening is defined in the dispenser for convenient removal of the individually vacuum-packed diapers within the dispenser, as shown in FIG. 87. Furthermore, each vacuum-packed diaper is disposed within an individual box that itself is removable from the dispenser, as shown in FIG. 88. The dispenser provides convenience to the consumer in that the first package contains non vacuum-packed diapers and vacuum-packed diapers with the vacuum-packed diapers being conveniently grouped together within the dispenser for wholesale removal from the first package. The dispenser then can be placed wherever a supply of individually vacuum-packed diapers is preferred by the consumer, such as in a vehicle or travel bag. According to various embodiments, a first package can contain any number of non vacuum-packed diapers and any number of dispensers of individually vacuum-packed diapers, and each dispenser can contain any number of vacuum-packed diapers.

Furthermore, as shown in FIGS. 86-88, each box containing a vacuum-packed diaper further comprises a kit, in that the box also contains one or more accessories for changing of a diaper. The kit contains a reduced diaper and, optionally, any or all of, for example, an ointment, a soft tipped swab for cleaning or application, a comforting powder, cleaning articles, and a disposal container. More particularly, as shown in FIG. 92 by way of a descriptive label printed on the box, the kit may contain a reduced diaper, Desitin®, one or more Q-Tip™ swabs, baby powder, disposable wipes, and a sealable disposal bag. Other kits may contain other items useful to the consumer, such as odor control articles like solutions or sprays. Yet other kits may include feeding-related items, such as infant formula, a feeding bottle and nipple, baby food, a utensil such as a feeding spoon, and a heat source for warming the baby food or formula.

Rather than being disposed within a dispense, a kit itself may be disposed with non vacuum-packed diapers in the first package, as shown in FIGS. 89-91.

Other examples of a kit including a box having a vacuum-packed diaper and one or more accessories are shown in FIGS. 93-95. Examples of a kit including a flexible bag having a vacuum-packed diaper and one or more accessories is shown in FIGS. 96-101. One or more of any of these kits may be combined with a first package of non vacuum-packed diapers.

FIG. 102 illustrates a preferred arrangement for disposing two 6-Pack dispensers in a package with non-vacuum-packed diapers. In this regard, a 6-Pack dispense is shown on either end of, and sandwiching therebetween, a row or column of non vacuum-packed diapers. This arrangement may be disposed within a first package to form a COMBO PACK. A dispenser as shown located at either end of the package will provide a degree of structural rigidity at the ends of the COMBO PACK, especially at the corners.

Finally, FIG. 103 illustrates a COMBO PACK at the center (identified by the trademark "PAMPERS") in which one or more vacuum-packed diapers are disposed in conjunction with non vacuum-packed diapers. Furthermore, one or more of the vacuum-packed diapers preferably is contained within a secondary packaging or container having a form factor represented by any one of the various possibilities shown in FIG. 103, which include: a plastic toy car; a stuffed animal such as a kangaroo ("Joey"); a cylindrical container or tube; a baby bottle; and a hard case clam-shell container. Moreover, the secondary packaging or container having the vacuum-packed diaper may include one or more additional accessories thereby to form a kit as shown.

In addition to the foregoing detailed description, a method for miniaturizing a diaper by folding and vacuum sealing and the resulting diaper is now described with reference to FIGS. 104-129. The miniaturizing of a diaper is accomplished by performing steps comprising: folding and compressing a diaper within a jig; clamping and transferring the folded compressed diaper from the jig to and inserting it into a pliable bag; and further miniaturizing the diaper within the plastic bag by vacuum sealing. The miniature size of the finished product fits into a convenient size box and avoids carrying bulky diapers within a purse or other carrying cases. The finished product is condensed down to a firm and hard exterior surface, and is disguised in appearance to look like a candy bar instead of a baby or an adult diaper. The process can be readily adapted to mechanical application for automatic manufacturing assembly line runs. The following is an exemplary method for miniaturizing a diaper very compactly by folding and vacuum sealing.

FIG. 104 is a view of a bulky diaper in the hands of a person (for reference, see Picture #1 of FIG. 114). In step 1 a bulky diaper 12 is inserted into a U-shaped elongated opened ended u-shaped forming jig 14. The diaper is laid in the jig such that the outside of the diaper 16 faces downwardly with the inside of the diaper 18 facing upward.

In step 2, the ragged elastic banded edges 20 of the diaper 12 are then folded, i.e., tucked inwardly (for reference, see Picture #2 of FIG. 115) so as to obtain a smooth clean line exterior. FIG. 105 is a sketch of a diaper within a jig made for holding and folding said diaper, with a person folding the rough edges inwardly.

In step 3, (for reference, see Picture #3 of FIG. 116), a first end 22 of the diaper is folded inwardly covering a middle portion 24 of the diaper and the other end 26 of the diaper is then folded in over the first end 22 and middle portion 24, thereby forming a rectangular shape 28 (for reference, see Picture #4 of FIG. 117). FIG. 106 is a view of a diaper with one end being folded inward. FIG. 107 is a view of a diaper with the other end being folded inward over the first fold.

In step 5, a spring tensioned hand clamp 30 is opened with one hand 32 so as to have the upper flat rectangular jaw 34 and lower jaw 36 placed over and under the completely folded diaper 28, respectively (for reference, see Pictures #5 & #6 of FIGS. 118-119). FIG. 108 shows a hand clamp gripping a folded diaper.

One hand holds the hand clamp and another hand 38 compresses the diaper 28 (for reference, see Picture #5 of FIG. 118). Having the folded diaper 28 compressed, folded diaper 28 is inserted into an open end 40 of an elastic pliable resilient bag 42 (for reference, see Picture #8 & #9 of FIGS. 121-122), using the hand clamp 30 and jig 14 to facilitate the insertion. FIG. 109 shows a hand clamp held by a person compressing a folded diaper being inserted into a plastic bag, and FIG. 110 is a perspective view of a folding jig facilitating the hand clamp for inserting a diaper into a plastic bag. FIG. 111 a folded and compressed diaper within a small plastic bag. The folded diaper 28 compressed by hand clamp 30 is directly inserted into the open ended bag 42 by hand 32 (for reference, see Picture #10 & #11 of FIGS. 123-124).

In step 6, folded diaper 28, now fully inserted into the bag 42 (for reference, see Picture #12 of FIG. 125), is then placed into a vacuum sealing machine 44 on deck 46 (for reference, see Picture #13, #14 & #15 of FIGS. 126-128). FIG. 112 a folded and compressed diaper within a small plastic bag being positioned within a vacuum sealing machine. The lid 48 of the vacuum sealing machine (for reference, see Picture #15 of FIG. 128) is fastened down and the vacuum sealing machine 44 vacuum seals and cuts the bag 42 as a finished product 50 (for reference, see Picture #1 of FIG. 129). The finished product 50 is very firm and dense, looks like a taffy candy bar and is as small as one.

In step 7, one or more of the finished products 50 (sometimes referred to as "Vac-U-Diaper" Product) are inserted into a box 52 for convenient carrying within a purse 54. Each Vac-U-Diaper Product measures 1 inch by 2 inches by 1½ inches. FIG. 113 shows a vacuum sealed diaper within a plastic bag held by a person.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A diaper kit for a changing of a single disposable diaper, comprising:

(a) a packaged single-use disposable diaper comprising,
   (i) a sealed substantially air impermeable encasement completely enclosing an interior space and having at least one airtight seal, and
   (ii) a single compressed single-use disposable diaper vacuum-sealed within said interior space of said sealed substantially air impermeable encasement,
   (iii) wherein said interior space has at least a partial vacuum whereby a pressure differential acts upon said encasement and said diaper to maintain said diaper in said compressed state;
(b) at least one diaper accessory for use in the diaper changing; and
(c) a container in which said packaged single-use disposable diaper and said diaper accessory are located, said diaper accessory being disposed outside of said interior space of said encasement;
(d) wherein,
   (i) none of a length, a width, and a height of said compressed diaper is greater than four inches, and
   (ii) said container is dimensioned to fit within a pocket of an article of clothing for carriage on one's person.

2. The diaper kit of claim 1, wherein said compressed diaper is folded into a substantially rectangular shape.

3. The diaper kit of claim 1, wherein said encasement, within which said diaper is disposed, has three dimensions comprising a width, a length, and a height, and the sum of two of said three dimensions is less than 10 cm with no single dimension of said three dimensions exceeding 10 cm.

4. The diaper kit of claim 1, wherein said interior space has a pressure within said interior space of said sealed substantially air impermeable encasement that is on the order of magnitude of a millibar(mbar).

5. The diaper kit of claim 4, wherein said pressure is between about 5 millibars and about 1 millibar.

6. The diaper kit of claim 1, wherein said vacuum-sealed diaper is sized to fit an adult.

7. The diaper kit of claim 1, wherein said encasement, within which said compressed diaper is vacuum-sealed, has a size and shape that closely corresponds to a size and shape of said compressed diaper.

8. The diaper kit of claim 7, wherein said pressure differential—as opposed to a hoop strength of said encasement—predominantly maintains said diaper in said compressed state.

9. The diaper kit of claim 8, wherein said encasement comprises a flexible material, and wherein said pressure differential causes said flexible material to conform to the general shape of said compressed diaper.

10. The diaper kit of claim 1, wherein said container is substantially rectangular in shape.

11. The diaper kit of claim 1, wherein said container comprises a box.

12. The diaper kit of claim 1, wherein said container is substantially cylindrical in shape.

13. A diaper kit for a changing of a single disposable diaper, comprising:
(a) a packaged single-use disposable diaper comprising,
   (i) a sealed substantially air impermeable encasement completely enclosing an interior space and having at least one airtight seal, and
   (ii) a single compressed single-use disposable diaper vacuum-sealed within said interior space of said sealed substantially air impermeable encasement,
   (iii) wherein said interior space has at least a partial vacuum whereby a pressure differential acts upon said encasement and said diaper to maintain said diaper in said compressed state;
(b) at least one diaper accessory for use in the diaper changing; and
(c) a container in which said packaged single-use disposable diaper and said diaper accessory are located, said diaper accessory being disposed outside of said interior space of said encasement;
(d) wherein said container is dimensioned to fit within a pocket of an article of clothing for carriage on one's person
(e) wherein said single compressed single-use disposable diaper vacuum-sealed within said interior space is folded at least once along a crosswise aspect of the diaper.

14. The diaper kit of claim 13, wherein said compressed diaper is folded into a substantially rectangular shape.

15. The diaper kit of claim 13, wherein said encasement, within which said diaper is disposed, has three dimensions comprising a width, a length, and a height, and the sum of two of said three dimensions is less than 10 cm with no single dimension of said three dimensions exceeding 10 cm.

16. The diaper kit of claim 13, wherein said interior space has a pressure within said interior space of said sealed substantially air impermeable encasement that is on the order of magnitude of a millibar(mbar).

17. The diaper kit of claim 13, wherein said pressure is between about 5 millibars and about 1 millibar.

18. The diaper kit of claim 13, wherein said vacuum-sealed diaper is sized to fit an adult.

19. The diaper kit of claim 13, wherein said encasement, within which said compressed diaper is vacuum-sealed, has a size and shape that closely corresponds to a size and shape of said compressed diaper.

20. A diaper kit for a changing of a single disposable diaper, comprising:
(a) a packaged single-use disposable diaper comprising,
   (i) a sealed substantially air impermeable encasement completely enclosing an interior space and having at least one airtight seal, and
   (ii) a single compressed single-use disposable diaper vacuum-sealed within said interior space of said sealed substantially air impermeable encasement,
   (iii) wherein said interior space has at least a partial vacuum whereby a pressure differential acts upon said encasement and said diaper to maintain said diaper in said compressed state, and
   (iv) wherein said sealed substantially air impermeable encasement is completely sealed, and
   (v) wherein said pressure differential—as opposed to a hoop strength of said encasement—predominantly maintains said diaper in said compressed state; and
(b) a container in which said packaged single-use disposable diaper and a diaper accessory are located, said diaper accessory being disposed outside of said interior space of said encasement;
(c) wherein,
   (i) none of a length, a width, and a height of said compressed diaper is greater than four inches, and
   (ii) said container is dimensioned to fit within a pocket of an article of clothing for carriage on one's person.

* * * * *